(12) United States Patent
Chicca et al.

(10) Patent No.: US 7,223,727 B2
(45) Date of Patent: May 29, 2007

(54) GSSP4 POLYNUCLEOTIDES AND POLYPEPTIDES AND USES THEREOF

(75) Inventors: Barbara Chicca, San Diego, CA (US); John Chicca, San Diego, CA (US); Blake Denison, Dublin, CA (US); Frances Yen-Potin, Vandoeuvre-les-Nancy (FR); Bernard Bihain, Cancale (FR); Stephane Bejanin, Paris (FR); Hiroaki Tanaka, Antony (FR); Severin Jobert, Praha (FR); Jean-Yves Giordano, Paris (FR); Jean-Baptiste Dumas Milne Edwards, Paris (FR)

(73) Assignee: Serono Genetics Institute S.A., Evry (FR)

( * ) Notice: Subject to any disclaimer, the term of this patent is extended or adjusted under 35 U.S.C. 154(b) by 43 days.

(21) Appl. No.: 10/467,554

(22) PCT Filed: Feb. 7, 2002 (Under 37 CFR 1.47)

(86) PCT No.: PCT/IB02/01514

§ 371 (c)(1), (2), (4) Date: Sep. 16, 2004

(87) PCT Pub. No.: WO02/069689

PCT Pub. Date: Sep. 12, 2002

(65) Prior Publication Data

US 2005/0075285 A1    Apr. 7, 2005

Related U.S. Application Data

(63) Continuation-in-part of application No. PCT/IB01/00914, filed on Apr. 18, 2001, application No. 10/467,554, and a continuation-in-part of application No. 09/876,997, filed on Jun. 8, 2001, now Pat. No. 7,060,479, which is a continuation-in-part of application No. 09/731,872, filed on Dec. 7, 2000, now abandoned, application No. 10/467,554, and a continuation-in-part of application No. 09/513,999, filed on Feb. 24, 2000, now Pat. No. 6,783,961, application No. 10/467,554, which is a continuation-in-part of application No. 09/621,976, filed on Jul. 21, 2000, now Pat. No. 6,639,063, application No. 10/467,554, which is a continuation-in-part of application No. 09/471,276, filed on Dec. 21, 1999, now Pat. No. 6,822,072, which is a continuation-in-part of application No. PCT/IB99/00712, filed on Apr. 9, 1999, which is a continuation-in-part of application No. 09/057,719, filed on Apr. 9, 1998, now abandoned, and a continuation-in-part of application No. 09/069,047, filed on Apr. 28, 1998, now abandoned.

(60) Provisional application No. 60/295,722, filed on Jun. 4, 2001, provisional application No. 60/267,624, filed on Feb. 9, 2001, provisional application No. 60/187,470, filed on Mar. 6, 2000, provisional application No. 60/169,629, filed on Dec. 8, 1999, provisional application No. 60/147,499, filed on Aug. 5, 1999, provisional application No. 60/122,487, filed on Feb. 26, 1999.

(51) Int. Cl.
*A61K 38/00* (2006.01)

(52) U.S. Cl. .......................... 514/2; 514/12; 514/909; 530/300

(58) Field of Classification Search .................... None
See application file for complete search history.

(56) References Cited

U.S. PATENT DOCUMENTS

| | | | |
|---|---|---|---|
| 4,914,025 A | 4/1990 | Manoil et al. | |
| 5,019,369 A | 5/1991 | Presant et al. | |
| 5,376,533 A | 12/1994 | Maclaren et al. | |
| 5,536,637 A | 7/1996 | Jacobs | |
| 5,872,141 A | 2/1999 | Umbreit et al. | |
| 6,034,062 A | 3/2000 | Thies et al. | |
| 6,110,490 A | 8/2000 | Thierry | |
| 6,204,060 B1 | 3/2001 | Mehtali et al. | |
| 6,242,179 B1 | 6/2001 | Shah et al. | |
| 6,485,938 B1 * | 11/2002 | Sheppard et al. | .......... 435/69.1 |

(Continued)

FOREIGN PATENT DOCUMENTS

EP        625 562 A1     11/1994

(Continued)

OTHER PUBLICATIONS

Ranneries et al, Am. J. Physiology 274: E155-E161, 1998.*

(Continued)

*Primary Examiner*—Gary Nickol
*Assistant Examiner*—Gyan Chandra
(74) *Attorney, Agent, or Firm*—Saliwanchik, Lloyd & Saliwanchik

(57) ABSTRACT

The present invention relates to the field of metabolic research. Metabolic disorders, such as obesity, are a public health problem that is serious and widespread. GSSP4 polypeptides have been identified that are believed to be beneficial in the treatment of metabolic disorders. These compounds should be effective for reducing cholesterol levels, body mass, body fat, and for treating metabolic-related diseases and disorders. The metabolic-related diseases or disorders include, but are not limited to, obesity, hyperlipidemia, hypercholesterolemia, atherosclerosis, diabetes, glucose intolerance, insulin resistance and hypertension.

6 Claims, No Drawings

U.S. PATENT DOCUMENTS

| | | | |
|---|---|---|---|
| 6,913,919 B2 * | 7/2005 | Botstein et al. | 435/252.3 |
| 2003/0059856 A1 * | 3/2003 | Ames et al. | 435/7.21 |
| 2004/0077535 A1 * | 4/2004 | Ohtaki et al. | 514/12 |
| 2005/0065079 A1 | 3/2005 | Soalia et al. | |

FOREIGN PATENT DOCUMENTS

| | | |
|---|---|---|
| EP | 1130094 A2 | 7/2000 |
| WO | WO 97/18826 A2 | 7/1995 |
| WO | WO 96/34981 A2 | 11/1996 |
| WO | WO 97/04097 A2 | 2/1997 |
| WO | WO 97/07198 A2 | 2/1997 |
| WO | WO 97/38003 A1 | 10/1997 |
| WO | WO 98/07830 A2 | 2/1998 |
| WO | WO 98/20895 | 5/1998 |
| WO | WO 98/45437 A2 | 10/1998 |
| WO | WO 98/55614 A2 | 12/1998 |
| WO | WO 99/47540 | 9/1999 |
| WO | WO 99/53051 | 10/1999 |
| WO | WO 00/52022 | 9/2000 |
| WO | WO 00/75327 | 12/2000 |

OTHER PUBLICATIONS

Heffernan et al., Am. J. Phys. End. Metab. 279: E501-E507, 2000.*

Wells, Biochemistry 29:8509-8517, 1990.*

Ngo et al., The protein Folding Problem and Tertiary Structure Prediction, 491-495, 1994.*

Abraham, E., et al., "Phosphatidic Acid Signaling Mediates Lung Cytokine Expression and Lung Inflammatory Injury After Hemorrhage in Mice", *J. Exp. Med.*, 1995, pp. 569-575, vol. 181.

Brindley, D. and Waggoner, D. "Phosphatidate phosphohydrolase and signal transduction", *Chem. Phys. Lipids*, 1996, pp. 45-57, vol. 80.

Bursten, S., et al., "Potential Role for Phosphatidic Acid in Mediating the Inflammatory Responses to TNFα and IL-1β", *Circ. Shock*, 1994, pp. 14-29, vol. 44.

English, D., "Phosphatidic Acid: A Lipid Messenger Involved in Intracellular and Extracellular Signalling", *Cell. Signal.*, 1996, pp. 341-347, vol. 8, No. 5.

English, D., et al., "Messenger functions of phosphatidic acid", *Chem. Phys. Lipids*, 1996, pp. 117-132, vol. 80.

Kent, C. "Eukaryotic Phospholipid Biosynthesis", *Ann. Rev. Biochem.*, 1995, pp. 315-343, vol. 64.

Leung, D., et al., "CT-2576, an inhibitor of phospholipids signaling, suppresses constitutive and induced expression of human immunodeficiency virus", *Proc. Natl. Acad. Sci. USA*, 1995, pp. 4813-4817, vol. 92.

Rice, G., et al., "Protection from endotoxic shock in mice by pharmacologic inhibition of phosphatidic acid", *Proc. Natl. Acad. Sci. USA*, 1994, 3857-3861, vol. 91.

Roberts, R. and Morris, A. "Role of phosphatidic acid phosphatase 2a in uptake of extracellular lipid phosphate mediators", *Biochimica et Biophysica Acta*, 2000, pp. 33-49, vol. 1487.

Salvador, G.A., et al., "Differential modulation of phospholipase D and phosphatidate phosphohydrolase during aging in rat cerebral cortex synaptosomes", *Exp. Gerontology*, 2002, pp. 543-552, vol. 37.

Stukey, J. and Carman, G. "Identification of a novel phosphatase sequence motif", *Protein Science*, 1997, pp. 469-472, vol. 6.

Database GENBANK, Accession NP_003702; Pandey, A.V., et al., "Protein phosphatase 2A and phosphoprotein SET regulate androgen production by p450c17", *J. Biol. Chem.*, 2003, pp. 2837-2844, vol. 278, Issue 5.

Database GENBANK, Accession No. NP_795714; Pandey, A.V., et al., "Protein phosphatase 2A and phosphoprotein SET regulate androgen production by p450c17", *J. Biol. Chem.*, 2003, pp. 2837-2844, vol. 278, Issue 5.

Database GENBANK, Accession No. NP_803133; Ishikawa, T., et al., "Cell surface activities of the human type 2b phosphatidic acid phosphatase", *J. Biochem.*, 2000, pp. 645-651, vol. 127, Issue 4.

Database GENBANK, Accession No. NP_808211; Zhang, N., et al., "Mice mutant for Ppap2c, a homolog of the germ cell migration regulator wunen, are viable and fertile", *Genesis*, 2000, pp. 137-140, vol. 27, Issue 4.

Accession No. AAB70690, Human hDPP protein sequence SEQ ID No. 7, May 17, 2001.

Jacobs, K. et al. "A Novel Method for Isolating Eukaryotic cDNA Clones Encoding Secreted Proteins", *Dendritic Cells: Antigen Presenting Cells of T and B Lymphocytes*, Mar. 10-16, 1995, p. C1-207.

Bougueleret, L. et al., "Extended cDNAs useful for expressing secreted proteins and to obtain specific antibodies", 2000, pp. 203-204, Accession No. AAY59685.

Cameron, C. et al., "Function and Protective Capacity of *Treponema pallidum* subsp. *pallidum* Glycerophosphodiester Phosphodiesterase", *Infection and Immunity* (1998), pp. 5763-5770, vol. 66, No. 12, American Society for Microbiology.

Downes, G. et al., "Structure and Mapping of the G Protein γ3 Subunit Gene and a Divergently Transcribed Novel Gene, Gng3lg", *Genomics* (1998), pp. 220-230, vol. 53, Academic Press.

Inoue, S. et al., "Growth Suppression of *Escherichia coli* by Induction of Expression of Mammalian Genes with Transmembrane of ATPase Domains", *Biochem. Biophys. Reas. Comm.* (2000), pp. 553-561, vol. 268, Academic Press.

Janson, H., et al., "Protein D, the Glycerophosphodiester Phosphodiesterase from *Haemophilus influenzae* with Affinity for Human Immunoglobulin D, Influences Virulence in a Rat Otitis Model", *Infection and Immunity*, 1994, pp. 4848-4854, vol. 62, No. 11, American Society for Microbiology.

Larson, T., et al., "Periplasmic Glycerophosphodiester Phosphodiesterase of *Escherichia coli*, a New Enzyme of the *glp* Regulon", *J. Biol. Chem.*, 1983, pp. 5428-5432, vol. 258, No. 9.

Magré, J. et al., "Identification of the gene altered in Berardinelli-Seip congenital lipodystrophy on chromosome 11q13", *Nature Genetics* (2001), pp. 365-370, vol. 28.

Meldrum, Brian, "Glutamate as a Neurotransmitter in the Brain: Review of Physiology and Pathology", *The Journal of Nutrition—Supplement* (presented at the International Symposium on Glutamate, 1998), 2000, pp. 1007S-1015S, Pub: American Society for Nutritional Sciences.

Munson, R. et al., "Protein D, a Putative Immunoglobulin D-Binding Protein Produced by *Haemophilus influenzae*, Is Glycerophosphodiester Phosphodiesterase", *J. Bacteriology*, 1993, pp. 4569-4571, vol. 175, No. 14.

Neer, Eva, "Heterotrimeric G Proteins: Organizers of Transmembrane Signals", *Cell*, 1995, pp. 249-257, vol. 80, Cell Press.

Schoepp, D. et al., "Metabotropic glutamate receptors in brain function and pathology", *TiPS*, 1993, pp. 13-20, vol. 14, Elsevier Science Publishers, Ltd., UK.

Zheng, B. et al., MIR16, a putative membrane glycerophosphodiester phosphodiesterase, interacts with RGS16, *PNAS*, 2000, pp. 3999-4004, vol. 97, No. 8.

Zheng, B. et al., MIR16, a putative membrane glycerophosphodiester phosphodiesterase, interacts with RGS16, *Proc. Natl. Acad. Sci. U.S.A.* (2000), pp. 3999-4004, vol. 97, No. 8, Accession No. AAF65234 (bases 1 to 331).

Zheng, B. et al., MIR16, a putative membrane glycerophosphodiester phosphodiesterase, interacts with RGS16, *Proc. Natl. Acad. Sci. U.S.A.* (2000), pp. 3999-4004, vol. 97, No. 8, Accession No. AF212862 (bases 1 to 1200).

Glycerophosphoryl Diester Phosphodiesterase *Escherichia coli* (1989), NiceProt View of SWISS-PROT:P10908.

Glycerophosphoryl Diester Phosphodiesterase, periplasmic [Precursor] *Escherichia coli* (1991), NiceProt View of SWISS-PROT:P09394.

Glycerophosphoryl Diester Phosphodiesterase [Precursor] *Haemophilus influenzae* (1995), NiceProt View of SWISS-PROT:Q06282.

Similar to G Protein Gamma 3 Linked Gene *Homo sapiens* (2001), NiceProt View of SWISS-PROT:Q9BSQ0.

Hypothetical 43.1 kDa protein *Mus musculus* (2000), NiceProt View of SWISS-PROT: Q9JMF1.

Jacobs, K. A. et al., "A genetic selection for isolating cDNAs encoding secreted proteins" *Gene* Oct. 1, 1987, pp. 289-296, vol. 198.

Tashiro, K. et al. "Signal Sequence Trap: A Cloning Strategy for Secreted Proteins and Type I Membrane Proteins" *Science*, Jul. 30, 1993, pp. 600-603, vol. 261.

Lim, E. M. et al. Identification of Mycobacterium tuberculosis DNA Sequences Encoding Exported Proteins by Using phoA Gene Fusions *Journal of Bacteriology*, Jan. 1995, pp. 59-65, vol. 177, No. 1.

Miyake et al. "RP105, a Novel B Cell Surface Molecule Implicated in B Cell Activation, is a Member of the Leucine-Rich Repeat Protein Family" *The Journal of Immunology*, pp. 3333-3340, The American Association of Immunologist: 0022-1767/95.

Fijiwara, T. et al. "HUM309B01B Clontech human aorta polyA+ mRNA (#6572) *Homo sapiens* cDNA clone GEN-309B015', mRNA sequence" Accession No. D62634, XP002032351.

Marra, M. et al., Accession No. W08383, "The WashU-HHMI Mouse EST Project", XP002032348.

Marra, M. et al., Accession No. W11170, "The WashU-HHMI Mouse EST Project", XP002032350.

Marra, M. et al., Accession No. W17930, "The WashU-HHMI Mouse EST Project", XP002032349.

Marra, M. et al., Accession No. W67046, "The WashU-HHMI Mouse EST Project", XP002032347.

Watson et al. "Recombinant DNA", second edition, Scientific American Books, 1994.

Greenwood et al. "Cloning of the Gene Encoding Human Somatostatin Receptor 2: Sequence Analysis of the 5'-Flanking Promoter Region" *Gene*, 1995, pp. 291-292.

Hillier et al. "Generation and Analysis of 280,000 Human Expressed Sequence Tags" *Genome Research*, 1996, pp. 807-828, vol. 6.

Lockhart et al. "Expression Monitoring by Hybridization to High-Density Oligonucleotide Arrays" *Research*, Oct. 7, 1996, pp. 1675-1680.

Von Heijne, G. et al. "A New Method for Predicting Signal Sequence Cleavage Sites" *Nucleic Acids Research*, 1986, vol. 14, No. 11.

Adams et al. "Initial Assessment of Human Gene Diversity and Expression Patterns Based Upon 83 Million Nucleotides of cDNA Sequence" *Nature*, Sep. 28, 1995, pp. 3-17, vol. 377.

Adams, M. D. et al. "3,400 New Expressed Sequence Tags Identify Diversity of Transcripts in Human Brain" *Nature*, Jul. 4, 1993, pp. 256-267, vol. 4.

Adams, M. D. et al. "Rapid CDNA Sequencing (Expressed Sequence Tags) From a Directionally Cloned Human Infant Brain CDNA Library" *Nature Genetics*, Aug. 1, 1993, pp. 373-380, vol. 4.

Kato, S. et al. "Construction of a Human Full-Length CDNA Bank" *Gene*, 1994, pp. 243-250, vol. 150.

Carninci, P. et al. "High-Efficiency Full-Length cDNA Cloning by Biotinylated Cap Trapper" *Genomics*, Nov. 1, 1996, pp. 327-336, vol. 37, No. 3.

Nomura et al. "Prediction of the Coding Sequences of Unidentified Human Genes. I. The Coding Sequences of 40 New Genes (KIAA0001-KIAA0040) Deduced by Analysis of Randomly Sampled cDNA Clones from Human Immature Myeloid Cell Line KG-1" *DNA Research*, 1994, pp. 27-35, vol. 1.

Ruben, S.M. et al. "Human secreted protein encoded by gene 21" Database GENESEQ [Online] AC No. Y76144, Mar. 23, 2000, XP002163702.

Ruben, S.M. et al. "Human secreted protein encoded by gene 21" Database GENESEQ [Online] AC No. Z65270, Mar. 23, 2000, XP002163703.

"ty73d05.x1 NCI_CGAP_Kid11 *Homo sapiens* cDNA clone Image:2284713" Database EMBL [Online] AC No. AI911546, *Natl. Cancer Inst.*, Jul. 30, 1999, XP002163704.

"qy42e02.x1 NCI_CGAP_Brn23 *Homo sapiens* cDNA clone Image:2014682" Database EMBL [Online] AC No. AI361251, *Natl. Cancer Inst.*, Jan. 7, 1999, XP002163705.

Database sequence Geneseq acc. #AAV88297, Feb. 12, 1999, see sequence alignment.

Genbank Accession No. U52112, date May 9, 1996.

Genbank Accession No. P14314, date Jan. 1, 1990.

Genbank Accession No. J03075, date Feb. 1, 1990.

Genbank Accession No. AC0044085, date Feb. 3, 1998.

Genbank Accession No. AA306438, date Apr. 18, 1997.

Genbank Accession No. AA215334, date Feb. 5, 1997.

Genbank Accession No. AA352450, date Apr. 18, 1997.

* cited by examiner

```
                          SEQUENCE LISTING

<160> NUMBER OF SEQ ID NOS: 18

<210> SEQ ID NO 1
<211> LENGTH: 6954
<212> TYPE: DNA
<213> ORGANISM: Homo sapiens
<220> FEATURE:
<221> NAME/KEY: misc_feature
<222> LOCATION: 1..1237
<223> OTHER INFORMATION: 5'regulatory region
<220> FEATURE:
<221> NAME/KEY: exon
<222> LOCATION: 1238..1377
<223> OTHER INFORMATION: exon 1
<220> FEATURE:
<221> NAME/KEY: exon
<222> LOCATION: 4050..4175
<223> OTHER INFORMATION: exon 2
<220> FEATURE:
<221> NAME/KEY: exon
<222> LOCATION: 6322..6702
<223> OTHER INFORMATION: exon 3
<220> FEATURE:
<221> NAME/KEY: misc_feature
<222> LOCATION: 6703..6954
<223> OTHER INFORMATION: 3'regulatory region
<220> FEATURE:
<221> NAME/KEY: allele
<222> LOCATION: 148
<223> OTHER INFORMATION: VLP-148_A_G    : polymorphic base A or G
<220> FEATURE:
<221> NAME/KEY: allele
<222> LOCATION: 816
<223> OTHER INFORMATION: VLP-816_G_A    : polymorphic base G or A
<220> FEATURE:
<221> NAME/KEY: allele
<222> LOCATION: 924
<223> OTHER INFORMATION: VLP-924_G_A    : polymorphic base G or A
<220> FEATURE:
<221> NAME/KEY: allele
<222> LOCATION: 1206
<223> OTHER INFORMATION: VLP-1206_C_A   : polymorphic base C or A
<220> FEATURE:
<221> NAME/KEY: allele
<222> LOCATION: 1851
<223> OTHER INFORMATION: VLP-1851_T_C   : polymorphic base T or C
<220> FEATURE:
<221> NAME/KEY: allele
<222> LOCATION: 2551
<223> OTHER INFORMATION: VLP-2551_G_A   : polymorphic base G or A
<220> FEATURE:
<221> NAME/KEY: allele
<222> LOCATION: 3124
```

```
<223> OTHER INFORMATION: VLP-3124_C_T    : polymorphic base C or T
<220> FEATURE:
<221> NAME/KEY: allele
<222> LOCATION: 3563
<223> OTHER INFORMATION: VLP-3563_G_A    : polymorphic base G or A
<220> FEATURE:
<221> NAME/KEY: allele
<222> LOCATION: 3792
<223> OTHER INFORMATION: VLP-3792_G_A    : polymorphic base G or A
<220> FEATURE:
<221> NAME/KEY: allele
<222> LOCATION: 4417
<223> OTHER INFORMATION: VLP-4417_A_C    : polymorphic base A or C
<220> FEATURE:
<221> NAME/KEY: allele
<222> LOCATION: 5757
<223> OTHER INFORMATION: VLP-5757_T_C    : polymorphic base T or C
<220> FEATURE:
<221> NAME/KEY: allele
<222> LOCATION: 6322
<223> OTHER INFORMATION: VLP-6322_A_G    : polymorphic base A or G
<220> FEATURE:
<221> NAME/KEY: primer_bind
<222> LOCATION: 82..103
<223> OTHER INFORMATION: VLP_82_103F
<220> FEATURE:
<221> NAME/KEY: primer_bind
<222> LOCATION: 522..542
<223> OTHER INFORMATION: VLP_522_542F
<220> FEATURE:
<221> NAME/KEY: primer_bind
<222> LOCATION: 1004..1024
<223> OTHER INFORMATION: VLP_1004_1024R complement
<220> FEATURE:
<221> NAME/KEY: primer_bind
<222> LOCATION: 999..1020
<223> OTHER INFORMATION: VLP_999_1021F
<220> FEATURE:
<221> NAME/KEY: primer_bind
<222> LOCATION: 1381..1402
<223> OTHER INFORMATION: VLP_1381_1402F
<220> FEATURE:
<221> NAME/KEY: primer_bind
<222> LOCATION: 1479..1500
<223> OTHER INFORMATION: VLP_1479_1500R complement
<220> FEATURE:
<221> NAME/KEY: primer_bind
<222> LOCATION: 1892..1914
<223> OTHER INFORMATION: VLP_1892_1914F
<220> FEATURE:
<221> NAME/KEY: primer_bind
<222> LOCATION: 1922..1943
<223> OTHER INFORMATION: VLP_1922_1944R complement
<220> FEATURE:
<221> NAME/KEY: primer_bind
<222> LOCATION: 2689..2711
<223> OTHER INFORMATION: VLP_2689_2711R complement
<220> FEATURE:
<221> NAME/KEY: primer_bind
<222> LOCATION: 2937..2958
<223> OTHER INFORMATION: VLP_2937_2958F
<220> FEATURE:
<221> NAME/KEY: primer_bind
<222> LOCATION: 3260..3281
<223> OTHER INFORMATION: VLP_3260_3281R complement
<220> FEATURE:
<221> NAME/KEY: primer_bind
<222> LOCATION: 3475..3497
<223> OTHER INFORMATION: VLP_3475_3498F
<220> FEATURE:
<221> NAME/KEY: primer_bind
<222> LOCATION: 3934..3956
<223> OTHER INFORMATION: VLP_3934_3956R complement
<220> FEATURE:
<221> NAME/KEY: primer_bind
<222> LOCATION: 4565..4587
<223> OTHER INFORMATION: VLP_4565_4587R complement
<220> FEATURE:
<221> NAME/KEY: primer_bind
```

```
<222> LOCATION: 5536..5557
<223> OTHER INFORMATION: VLP_5536_5557F
<220> FEATURE:
<221> NAME/KEY: primer_bind
<222> LOCATION: 6133..6154
<223> OTHER INFORMATION: VLP_6133_6154F
<220> FEATURE:
<221> NAME/KEY: primer_bind
<222> LOCATION: 6647..6667
<223> OTHER INFORMATION: VLP_6647_6667R complement
<220> FEATURE:
<221> NAME/KEY: primer_bind
<222> LOCATION: 6808..6829
<223> OTHER INFORMATION: VLP_6808_6829R complement
<220> FEATURE:
<221> NAME/KEY: primer_bind
<222> LOCATION: 128..147
<223> OTHER INFORMATION: VLP_128_148A_F
<220> FEATURE:
<221> NAME/KEY: primer_bind
<222> LOCATION: 128..148
<223> OTHER INFORMATION: VLP_128_148G_F
<220> FEATURE:
<221> NAME/KEY: primer_bind
<222> LOCATION: 240..261
<223> OTHER INFORMATION: VLP_240_261R complement
<220> FEATURE:
<221> NAME/KEY: primer_bind
<222> LOCATION: 2534..2550
<223> OTHER INFORMATION: VLP_2534_2551A_F
<220> FEATURE:
<221> NAME/KEY: primer_bind
<222> LOCATION: 2745..2765
<223> OTHER INFORMATION: VLP_2745_2765R complement
<220> FEATURE:
<221> NAME/KEY: primer_bind
<222> LOCATION: 3346..3356
<223> OTHER INFORMATION: VLP_240_261R complement
<220> FEATURE:
<221> NAME/KEY: primer_bind
<222> LOCATION: 4401..4416
<223> OTHER INFORMATION: VLP_4401_4417A_F
<220> FEATURE:
<221> NAME/KEY: primer_bind
<222> LOCATION: 4620..4640
<223> OTHER INFORMATION: VLP_4620_4640R complement
<220> FEATURE:
<221> NAME/KEY: primer_bind
<222> LOCATION: 6298..6321
<223> OTHER INFORMATION: VLP_6298_6322G_F
<220> FEATURE:
<221> NAME/KEY: primer_bind
<222> LOCATION: 6298..6322
<223> OTHER INFORMATION: VLP_6298_6322A_F
<220> FEATURE:
<221> NAME/KEY: primer_bind
<222> LOCATION: 6478..6499
<223> OTHER INFORMATION: VLP_6478_6499R complement

<400> SEQUENCE: 1
tcaatgtgga aaccctagac ccctgtgaca tttgataaga aaggttttgt ggatgaatct      60
gcttgtgaaa tactacaaac tgcatttccc acttggtgtt tcaaacactt attagcatat    120
gaaaggccct gaaaagttct gcaaaaarca agccggtttg tgtttcccaa attttttgact  180 gtagaagtct tttatttgtt tatttgtgta ttaacatatt gcaacacata ccttgggaaa    240
tgttggcttt tattactgtg gagagaaggc agatcatctg acaaagcact gggagctctc    300
tctgggtcgt atgacacaga gagggctggg gtcaggggct tccctcacag gcggaggggc    360
catcccgaaa gtcaacttcc caccagactg gcatctgaga ccaccgtgtt tatacactca    420
cggataaggc cactctcatg ctcacccctg aaactggaag gccagtggtg tggctctggt   480
acctttcagc cacagcccat accagctcgg ctctgcaggg tactgagaga gtgtgtgccc   540
```

```
tgtatgtttg ctggctttct gcccttgggt cattgtacca agggacacttt gctggtgttc      600 atcctgagcc catgagagag caaatccttta tgtgtgtgtc acttaggaac atcagcccca      660
caagtctggt cttttttttcc tcactgtctt atggctcctc actataattt taaccttttta    720 gagaaataag gataccacct caccctcttc tgtcttctca gctacctctg tgttgagccc       780
atggtaaatg cctagataag tcttggtgtg agtgaragg aaccaataat cttgtatgtt        840
gcatagtttg gtgcagggaa gcataaatgg tgatgttgca aatcccttaa ttcattacca      900
gaggctttcc tctgcccccaa gtargataga aggatacccca gaggcagaaa agaacattga   960
gtgaaatata cataactgtc tgaatcactg cgttcttggg agagttagag caaccgtcaa      1020 agcccccaa gtatccattt ttattggttt tgatgttgat ttgatgttgt tagagattca       1080
ggtctcatct tcgcttctga gatcatctga gtaacatcgg tgttggagaa gggaagagca     1140
gagatgaggc atccacaggc agccctggat cctgagtgta acatctggg aggaggcggg       1200 ggatgmagga gagcctggcc tccccagctt gccaggcaca aggctgagcg ggaggaagcg      1260
agaggcatct aagcaggcag tgttttgcct tcaccccaag tgaccatgag aggtgccacg     1320
cgagtctcaa tcatgctcct cctagtaact gtgtctgact gtgctgtgat cacagggggta   1380 agtcgcctaa cattctctgt gccttgggtt ttgggaagat gtcagggtct gcacgggttg     1440
tgagcccagg aaccatgcag gaggctctgt tggctcaaca cagtgtgaac caaagggaat    1500
ggggaattat gcattaaagg gattgcatgc gattttcaga ctagttagac ctcactctac     1560
taaatgggat ctgcttttga gaagctgtgt atgaatcaaa tcctgttttc aatgtgttag     1620
cagagcattg aacattttga agttcagtcc tttggtaaag tgaagattcc tattaagtaa    1680
taaggaattc ctttataaag tggattggca aaccttaact tatcttttgt gtgaatttta    1740
attttatttt atggtctgat tcacatatta atattaatat taatttacat agcatgttga     1800
cttaattaaa ggcagtaagc ttaattaaag gtggtaagct tataaacttc yattgtataa    1860
acttaacctc cgcttagaaa ggatatcttt gaaactcttt cactctgtgc ctgcctagtt    1920
agttctgaga ggaatatggg tgccactaac attcagctga gtgtacccca agcaagcat     1980 ccagataaca agtagatatc cagtctcgaa gcagagaagc aaaggttcag catatgggca    2040
ctgtacaatt ggttcaaaat attcagatca tggttttctc tcggaagttt gcttttacct   2100
caaaccacct tcaaataggg gcacatgatg tgttatggta gcaggaccat tcttactgaa    2160
gcagaaagca atgctgtacc tgagagcttt ccatataaaa tccactggaa gaaaaaggtc    2220
ggggaagcag ggaaactaac ttttagttca gcctccacca gcttttaca tggatagtgg    2280 aaatgtagag aaatgccaaa caattcctgg aattgggtta attttaccat tcacagaaag   2340
gacaaattct ttcttttctc ttttaaagga aaaacactga gttcaaaaga acaaatatta    2400
aaggcgagtc aaatgctttt gagatccaaa gcaaaaataa aaataattgt gaaggcagaa    2460
ttatacctaa tgaagtgttt acactgtagg ctgcccttct atggggtagc ttgaaaatct    2520
gggagggcaa gaacaatgga gagaagcccc rgctgctgcg cggtgagggc aggagcagcg    2580
tggttggcct ggatgccagg cttgcctcac cacccgtgcc agctccagca ctggcccaga    2640
gtgacagcag ggcaggcaga tctgagagcg gcaggcaaac atttttcacgg tgaaaagcac  2700 aatagagagc acttttccct aggtgaggga aacccaggaa agacaggtga gtggtgagaa    2760
cagggcagta agggaagtc aggaaccccc aggctcccca catcctccat gtcctgctgg     2820
tgtcccactt ctgattttca gcaggagccc aggctccacc acctctacac tcccctgctc    2880
cctggactgt aactgtcccc acatccaagg ctttatgatc cttcttccaa gagtgggaca    2940
```

```
gtgatgcccc acctctatgg gagaagaaga gtcgactggg gtttcctttA ccccaacccc   3000
aagcttttgt ggcctggctg ggtgtgagac gtgcccttgc tgggctggag acaggcacag   3060
ctgggtgccc accacccgta actcctctgc atgatctgtg gagctgacat ccactctttc   3120
cctyttgggt ctgagcaagt aggaggcttc caggtcctgc cacgtcccac acagcagcct   3180
gaaggtgccc ataggctttt attggagaag agtgatccaa aacccagctt tgcatttcag   3240
ctcagaaaag ccacatagca tctctgagaa tggcaagtgt ggatgcttct tcagcaggtc   3300
cccacctgag tctggagcag ttaagagttc tgtcttcccc ggctctggct tttatttaac   3360
gtgggctcat gttaaatgtg agcttattta atgtggcctt ctttacaaat ggtaccttcc   3420
ccaaaccagg cagggccgct cagctcctgt tctgcgatcc tctctgggaa tcatggaagt   3480
cagtagagaa accctgggag aggcacctgt tcactggggt gctggcccct ctgctgaggc   3540
tgggccactt gagggccagg atrgggtgc ctccatgcag aggggaggga ctgaccacag   3600
tgcagagtca gggctggaga ctcctggtcc aaggcagctc agtactgacc accaaggaat   3660
ttgggccatc agggtccctc ccacctctga gaattctaat taattcaatt ccaccagcat   3720
ccactgagca tctacttagc cctagaaaag ctatgccttc taacctccag ccttgtcaga   3780
aaaggaggac trtcttcctt ctgagtggcc tccaggagct tggaagtttc ctcagatcca   3840
gatccaatgc ccccctgagc cctgagcctc cccacgaggg gagcaaggca ataaagtgtg   3900
gcccagggtg ttctgttagg ctaaggccgg gggtgatact ctcagcctct tcttgctcca   3960
tcctgataag ggcttttttgg atctaccctt cccttctgct ttctcttggg tgcactaatg   4020
aactgttccc ttctctctcc ctcctacagg cctgtgagcg ggatgtccag tgtggggcag   4080
gcacctgctg tgccatcagc ctgtggcttc gagggctgcg gatgtgcacc ccgctggggc   4140
gggaaggcga ggagtgccac cccggcagcc acaaggtact ctgcagacac tgcataggtg   4200
cacatatgtg ggtgggccat gcggggagca gagggtgatg tcctgggcc ttgctctagc   4260 taggaaggct agagaggctg gctccagaga ggcagtctag ggaggctgtg gctccagagg   4320
acttcaccct cctctgatag ctgatccagc cctgatccag ccctgaatg tccaaggga   4380 agcagaaggc tatggggttg ctgtgcccct gccatcmaca ggcatccacc ttacttagtg   4440
ccctgcagat gacacatttg tacatttatt tgtacagggc ctgacataat tcatctacaa   4500
acttctagca caggttggag aaccactgat ctttatttga tcctcactgc aaccctgggc   4560
aatgctgagg aaactgacat acagcaaagt catgtgactt gctcaaggca cacaaccaat   4620
gagacagagc tgggactgga actgcagttt tccgatgcca cctctagtca tacctcactg   4680
atgttgggca ctgcctcctt gttttttgggg ggcagcctca ggtggagggg tgccactgat   4740
cttataggct gttaaacaag ctgggcattc ccagcccta atttgctgtg tggacttggg   4800
caaactacct cacctgctct caggccacac ttatatgatg agtggagcaa actcactacc   4860
tctaatgtcc cttatggatc tgatgaattc agatttggga aggatctcac atgcccttg   4920 ctctgtaaga acttcccttc agggacacaa aagtagaccc acaaaatcgc cttccacacc   4980
tggtcaggcc tacagtgagg caagtgaggt gcccacttta agaagtcact ctctcttgtg   5040
gcataagtac atagctcctg ccttgctccc actccttgac ctccagctcc cagtccagag   5100
tcctctggag ccacagcatc cctgctgctc tccctctctg gagccacttt accacacttt   5160
accagttaac cagtgaagct cccaattccc acagcttttt cattaaaatg caaatggtgg   5220
tggttcaatc tagtctgaca ttgacatatt agaaggcaat tagggcattt ccacaggctc   5280
```

```
tcaggtgact tgctttcctc cctgggcctt gcccctctcc ctacatgtac ccctctgtct    5340
gaattagaca ttcctgaaca caggctttca ggcttaccag ctgtcttcca cctggcactc    5400
aggcatgttt cctgctcttc ggggacttgc ctgcaccccg gctcggtgct catctctagg    5460
cacggagcgt cctccagcgg tttctctccc aatcacagcc cctgtccaac ctcctgtccc    5520
aggacgaaga ggggctaggg agtggtgaac gagtcaggac aatgtggcag tccttgtaac    5580
cttggggaat gtgaggtggt tcagctccag atccatattc ccaatacaga caacagtgat    5640
aaaaaaacta atgctgagtg cttcctgtat gccacccttc atactgggtg cttttttgtta   5700 ttttaacctc tttataacca catgtggtag gtgctattat taaaccattt tacaaaygat    5760
aaagctgagg cacagagagg ccaaatgatt tgctgattat cacacagctg ggaagcggta    5820
gacctgggat ttgaacccag gcagtctgac aatgggccca tgctcctaac ttctccctga    5880
ggatacccca ttggtttagc actcctctag ggtgtgagtc agggcagaga tggtggctgt    5940
cctattcacg gctgcacttg cagcacccac catggttttg agcccataat ggatgagcaa    6000
caaacattca atcaatggac atgtgtgtgc gtgtgtgtgt gtgtgtgcac gcacatgtgt    6060
gctgagtctc cagagccagg tagcctgggt gcaaatccta gctcctccac aaattagctg    6120
tgtgatcttg gcgtattgct tagccacacc gtacctcggt ttcctcatct ctaattgcta    6180
ttattgttgt gctaggtgca gtggagaagt gggctagggt gtgggggtga gacttttgcc    6240
agtgctgggc tgagcagaga ctgctgccag gaggcccacc tacctccctt tggtgaaggt    6300 gttgattttct tctctcctta grtccccttc ttcaggaaac gcaagcacca cacctgtcct    6360
tgcttgccca acctgctgtg ctccaggttc ccggacggca ggtaccgctg ctccatggac    6420
ttgaagaaca tcaattttta ggcgcttgcc tggtctcagg atacccacca tccttttcct    6480
gagcacagcc tggattttta tttctgccat gaaacccagc tcccatgact ctcccagtcc    6540
ctacactgac tacctgatc tctcttgtct agtacgcaca tatgcacaca ggcagacata    6600
cctcccatca tgacatggtc cccaggctgg cctgaggatg tcacagcttg aggctgtggt    6660
gtgaaaggtg gccagcctgg ttctcttccc tgctcaggct gccagagagg tggtaaatgg    6720
cagaaaggac attcccccctc ccctcccccag gtgacctgct ctctttcctg ggccctgccc    6780
ctctccccac atgtatccct cggtctgaat tagacattcc tgggcacagg ctcttgggtg    6840
cattgctcag agtcccaggt cctggcctga ccctcaggcc cttcacgtga ggtctgtgag    6900
gtccaatttg ggcgcccctc tccttccctc gattggttaa ctccttagtt tcag           6954
```

<210> SEQ ID NO 2
<211> LENGTH: 666
<212> TYPE: DNA
<213> ORGANISM: Homo sapiens
<220> FEATURE:
<221> NAME/KEY: sig_peptide
<222> LOCATION: 1..20
<223> OTHER INFORMATION: Von Heijne matrix, score:7.21 seq:
      VSIMLLLVTVSDC/AV
<220> FEATURE:
<221> NAME/KEY: 5'UTR
<222> LOCATION: 1..68
<220> FEATURE:
<221> NAME/KEY: CDS
<222> LOCATION: 69..386
<220> FEATURE:
<221> NAME/KEY: 3'UTR
<222> LOCATION: 387..666
<220> FEATURE:
<221> NAME/KEY: allele
<222> LOCATION: 266
<223> OTHER INFORMATION: VLP_6322_A_G : polymorphic base A or G

<400> SEQUENCE: 2

```
acaaggctga gcgggaggaa gcgagaggca tctaagcagg cagtgttttg ccttcacccc      60 aagtgacc atg aga ggt gcc acg cga gtc tca atc atg ctc ctc cta gta     110
         Met Arg Gly Ala Thr Arg Val Ser Ile Met Leu Leu Leu Val
         1               5                   10 act gtg tct gac tgt gct gtg atc aca ggg gcc tgt gag cga gat gtc     158
Thr Val Ser Asp Cys Ala Val Ile Thr Gly Ala Cys Glu Arg Asp Val
15                  20                  25                  30 cag tgt ggg gca ggc acc tgc tgt gcc atc agc ctg tgg ctt cga ggg     206
Gln Cys Gly Ala Gly Thr Cys Cys Ala Ile Ser Leu Trp Leu Arg Gly
                    35                  40                  45 ctg cgg atg tgc acc ccg ctg ggg cgg gaa ggc gag gag tgc cac ccc     254
Leu Arg Met Cys Thr Pro Leu Gly Arg Glu Gly Glu Glu Cys His Pro
            50                  55                  60 ggc agc cac aag atc ccc ttc ttc agg aaa cgc aag cac cac acc tgt     302
Gly Ser His Lys Ile Pro Phe Phe Arg Lys Arg Lys His His Thr Cys
65                  70                  75 cct tgc ttg ccc aac ctg ctg tgc tcc agg ttc ccg gac ggc agg tac     350
Pro Cys Leu Pro Asn Leu Leu Cys Ser Arg Phe Pro Asp Gly Arg Tyr
80                  85                  90 cgc tgc tcc atg gac ttg aag aac atc aat ttt taggcgcttg cctggtctca   403
Arg Cys Ser Met Asp Leu Lys Asn Ile Asn Phe
95                  100                 105 ggatacccac catcctttc ctgagcacag cctggatttt tatttctgcc atgaaaccca     463
gctcccatga ctctcccagt ccctacactg actaccctga tctctcttgt ctagtacgca    523
catatgcaca caggcagaca tacctcccat catgacatgg tccccaggct ggcctgagga    583
tgtcacagct tgaggctgtg gtgtgaaagg tggccagcct ggttctcttc cctgctcagg    643
ctgcactcaa aaaaaaaaaa aaa                                            666
```

<210> SEQ ID NO 3
<211> LENGTH: 105
<212> TYPE: PRT
<213> ORGANISM: Homo sapiens

<400> SEQUENCE: 3

```
Met Arg Gly Ala Thr Arg Val Ser Ile Met Leu Leu Leu Val Thr Val
1               5                   10                  15

Ser Asp Cys Ala Val Ile Thr Gly Ala Cys Glu Arg Asp Val Gln Cys
            20                  25                  30

Gly Ala Gly Thr Cys Cys Ala Ile Ser Leu Trp Leu Arg Gly Leu Arg
        35                  40                  45

Met Cys Thr Pro Leu Gly Arg Glu Gly Glu Glu Cys His Pro Gly Ser
    50                  55                  60

His Lys Ile Pro Phe Phe Arg Lys Arg Lys His His Thr Cys Pro Cys
65                  70                  75                  80

Leu Pro Asn Leu Leu Cys Ser Arg Phe Pro Asp Gly Arg Tyr Arg Cys
                85                  90                  95

Ser Met Asp Leu Lys Asn Ile Asn Phe
            100                 105
```

<210> SEQ ID NO 4
<211> LENGTH: 47
<212> TYPE: DNA
<213> ORGANISM: Homo sapiens

<400> SEQUENCE: 4
catctgggag gaggcgggggg atgmaggaga gcctggcctc cccagct    47

<210> SEQ ID NO 5
<211> LENGTH: 47
<212> TYPE: DNA
<213> ORGANISM: Homo sapiens

<400> SEQUENCE: 5
ggccctgaaa agttctgcaa aaarcaagcc ggtttgtgtt tcccaaa    47

<210> SEQ ID NO 6
<211> LENGTH: 47
<212> TYPE: DNA
<213> ORGANISM: Homo sapiens

<400> SEQUENCE: 6
aaggtggtaa gcttataaac ttcyattgta taaacttaac ctccgct    47

<210> SEQ ID NO 7
<211> LENGTH: 47
<212> TYPE: DNA
<213> ORGANISM: Homo sapiens

<400> SEQUENCE: 7
caagaacaat ggagagaagc cccrgctgct gcgcggtgag ggcagga    47

<210> SEQ ID NO 8
<211> LENGTH: 47
<212> TYPE: DNA
<213> ORGANISM: Homo sapiens

<400> SEQUENCE: 8
gagctgacat ccactctttc cctyttgggt ctgagcaagt aggaggc    47

<210> SEQ ID NO 9
<211> LENGTH: 47
<212> TYPE: DNA
<213> ORGANISM: Homo sapiens

<400> SEQUENCE: 9
ctgggccact tgagggccag gatrggggtg cctccatgca gagggga    47

<210> SEQ ID NO 10
<211> LENGTH: 47
<212> TYPE: DNA
<213> ORGANISM: Homo sapiens

<400> SEQUENCE: 10
agccttgtca gaaaaggagg actrtcttcc ttctgagtgg cctccag    47

<210> SEQ ID NO 11
<211> LENGTH: 47
<212> TYPE: DNA
<213> ORGANISM: Homo sapiens

```
<400> SEQUENCE: 11
ggggttgctg tgcccctgcc atcmacaggc atccaccta cttagtg                47

<210> SEQ ID NO 12
<211> LENGTH: 47
<212> TYPE: DNA
<213> ORGANISM: Homo sapiens

<400> SEQUENCE: 12
ctattattaa accatttac aaaygataaa gctgaggcac agagagg                47

<210> SEQ ID NO 13
<211> LENGTH: 47
<212> TYPE: DNA
<213> ORGANISM: Homo sapiens

<400> SEQUENCE: 13
gtgttgattt cttctctcct tagrtcccct tcttcaggaa acgcaag                47

<210> SEQ ID NO 14
<211> LENGTH: 47
<212> TYPE: DNA
<213> ORGANISM: Homo sapiens

<400> SEQUENCE: 14
tagataagtc ttggtgtgag tgaragggaa ccaataatct tgtatgt                47

<210> SEQ ID NO 15
<211> LENGTH: 47
<212> TYPE: DNA
<213> ORGANISM: Homo sapiens

<400> SEQUENCE: 15
gaggctttcc tctgccccaa gtargataga aggataccca gaggcag                47

<210> SEQ ID NO 16
<211> LENGTH: 47
<212> TYPE: DNA
<213> ORGANISM: Homo sapiens

<400> SEQUENCE: 16
ctgtttctag tgtctggtgg agayatcaat ttaaagagct cttcaga                47

<210> SEQ ID NO 17
<211> LENGTH: 47
<212> TYPE: DNA
<213> ORGANISM: Homo sapiens

<400> SEQUENCE: 17
actgtgtttc tttttctttt ttcstcttct tttttatggt tttaaaa                47

<210> SEQ ID NO 18
<211> LENGTH: 47
<212> TYPE: DNA
<213> ORGANISM: Homo sapiens

<400> SEQUENCE: 18
tcaagctgaa gggatgcttt ggcytgactt ccaccacctg ggctcat                47
```

GSSP4 POLYNUCLEOTIDES AND POLYPEPTIDES AND USES THEREOF

FIELD OF THE INVENTION

The present invention relates to the field of metabolic research, in particular the discovery of compounds effective for reducing cholesterol levels, body fat, and body mass, and useful for treating metabolic-related diseases and disorders. The metabolic-related diseases or disorders envisioned to be treated by the methods of the invention include, but are not limited to, obesity, hyperlipidemia, hypercholesterolemia, atherosclerosis, diabetes, glucose intolerance, insulin resistance and hypertension.

BACKGROUND OF THE INVENTION

The following discussion is intended to facilitate the understanding of the invention, but is not intended nor admitted to be prior art to the invention.

Obesity is a public health problem that is serious, widespread, and increasing. In the United States, 20 percent of the population is obese; in Europe, a slightly lower percentage is obese (Friedman (2000) Nature 404:632–634). Obesity is associated with increased risk of hypertension, cardiovascular disease, diabetes, and cancer as well as respiratory complications and osteoarthritis (Kopelman (2000) Nature 404:635–643). Even modest weight loss ameliorates these associated conditions.

While still acknowledging that lifestyle factors including environment, diet, age and exercise play a role in obesity, twin studies, analyses of familial aggregation, and adoption studies all indicate that obesity is largely the result of genetic factors (Barsh et al (2000) Nature 404:644–651). In agreement with these studies, is the fact that an increasing number of obesity-related genes are being identified. Some of the more extensively studied genes include those encoding leptin (ob) and its receptor (db), pro-opiomelanocortin (Pomc), melanocortin-4-receptor (Mc4r), agouti protein ($A^y$), carboxypeptidase E (fat), 5-hydroxytryptamine receptor 2C (Htr2c), nescient basic helix-loop-helix 2 (Nhlh2), prohormone convertase 1 IPCSK1), and tubby protein (tubby) (rev'd in Barsh et al (2000) Nature 404:644–651).

SUMMARY OF THE INVENTION

The instant invention is based on the discovery that GSSP4 polypeptides have unexpected effects in vitro and in vivo, including utility for weight reduction, prevention of weight gain, reduction of cholesterol levels, and control of blood glucose levels in humans and other mammals. These unexpected effects of administration of GSSP4 polypeptides in mammals also include reduction of elevated free fatty acid levels caused by administration of epinephrine, i.v. injection of "intralipid", or administration of a high fat test meal, as well as increased fatty acid oxidation in muscle cells, reduction of circulating cholesterol levels, modulation of blood glucose and weight reduction in mammals, particularly those consuming a high fat/high carbohydrate diet. These effects are unexpected and surprising given that proteins of similar structure or homology (such as colipase and mamba intestinal toxin 1) have not been shown to have utility for weight reduction, prevention of weight gain, reduction of cholesterol levels, and control of blood glucose levels. However, the GSSP4 polypeptides of the invention are effective and can be provided at levels that are feasible for treatments in humans.

Thus, the invention is drawn to GSSP4 polypeptides, polynucleotides encoding said polypeptides, vectors comprising said GSSP4 polynucleotides, and cells recombinant for said GSSP4 polynucleotides, as well as to pharmaceutical and physiologically acceptable compositions comprising said GSSP4 polypeptide and methods of administering said GSSP4 polypeptides or polynucleotides in a pharmaceutical and physiologically acceptable compositions in order to reduce body weight, cholesterol levels or glucose levels, or to treat metabolic-related diseases and disorders. Assays for identifying agonists and antagonists of metabolic-related activity are also part of the invention.

In a first aspect, the invention features a purified, isolated, or recombinant GSSP4 polypeptides. In preferred embodiments, said polypeptides comprise, consist essentially of, or consist of, those having significant activity wherein the said activity is selected from the group consisting of cholesterol reduction, cholesterol regulation, lipid partitioning, lipid metabolism, glucose control, and insulin-like activity. In preferred embodiments, said polypeptides comprise, consist essentially of, or consist of, the full length polypeptide of SEQ ID NO:3 or a fragment of consecutive amino acids of the full length polypeptide sequence of SEQ ID NO:3. In other preferred embodiments, said polypeptides comprise an amino acid sequence at least 70%, 75%, 80%, 85%, 90%, 91%, 92%, 93%, 94%, 95%, 96%, 97%, 98%, or 99% identical to the corresponding consecutive amino acids of the polypeptide sequences identified in SEQ ID NO:3.

In a further preferred embodiment, the GSSP4 polypeptide is able to lower circulating (either blood, serum or plasma) levels (concentration) of: (i) free fatty acids, (ii) glucose, and/or (iii) triglycerides.

Further preferred GSSP4 polypeptides are those that significantly stimulate muscle lipid or free fatty acid oxidation. Further preferred GSSP4 polypeptides are those that cause C2C12 cells differentiated in the presence of said polypeptides to undergo at least 10%, 20%, 30%, 35%, or 40% more oleate oxidation as compared to untreated cells.

Further preferred GSSP4 polypeptides are those that are at least 30% more efficient than untreated cells at increasing leptin uptake in a liver cell line (preferably BPRCL mouse liver cells (ATCC CRL-2217)).

Further preferred GSSP4 polypeptides are those that significantly reduce the postprandial increase in plasma free fatty acids, particularly following a high fat meal.

Further preferred GSSP4 polypeptides are those that significantly reduce or eliminate ketone body production, particularly following a high fat meal.

Further preferred GSSP4 polypeptides are those that increase glucose uptake in skeletal muscle cells.

Further preferred GSSP4 polypeptides are those that increase glucose uptake in adipose cells.

Further preferred GSSP4 polypeptides are those that increase glucose uptake in neuronal cells.

Further preferred GSSP4 polypeptides are those that increase glucose uptake in red blood cells.

Further preferred GSSP4 polypeptides are those that increase glucose uptake in the brain.

Further preferred GSSP4 polypeptides are those that significantly reduce the postprandial increase in plasma glucose following a meal, particularly a high carbohydrate meal.

Further preferred GSSP4 polypeptides are those that significantly prevent the postprandial increase in plasma glucose following a meal, particularly a high fat or a high carbohydrate meal.

Further preferred GSSP4 polypeptides are those that improve insulin sensitivity.

Further preferred GSSP4 polypeptides are those that modulate food intake or food selection.

Further preferred GSSP4 polypeptides are those that modulate satiety.

Further preferred GSSP4 polypeptides are those that modulate fatty acid metabolism.

Further preferred GSSP4 polypeptides are those that modulate cholesterol metabolism, particularly in steroidogenic tissues. Therefore, said polypeptides have a potential role in effecting, either directly or indirectly or both, levels of reproductive hormones (eg. estradiol, progesterone, testosterone).

Further preferred GSSP4 polypeptides are those that modulate cortisol levels.

Further preferred GSSP4 polypeptides are those that modulate aldosterone levels. Therefore, said polypeptides have a potential role in effecting, either directly or indirectly or both, levels of sodium and potassium.

Further preferred GSSP4 polypeptides are those that modulate blood pressure preferably to normalize blood pressure within a normal range.

Further preferred GSSP4 polypeptides are those that form multimers (e.g., heteromultimers or homomultimers) in vitro and/or in vivo. Preferred multimers are homodimers or homotrimers. Other preferred multimers are homomultimers comprising at least 4, 6, 8, 9, 10 or 12 GSSP4 polypeptides. Other preferred multimers are hetero multimers comprising GSSP4 polypeptides of the invention.

Further preferred embodiments include heterologous polypeptides comprising a GSSP4 polypeptide of the invention.

In a second aspect, the invention features purified, isolated, or recombinant polynucleotides encoding said GSSP4 polypeptides described in the first aspect, or the complement thereof. A further preferred embodiment of the invention is a recombinant, purified or isolated polynucleotide comprising, or consisting of a mammalian genomic sequence, gene, cDNA, or fragments thereof. In one aspect the sequence is derived from a human, mouse or other mammal. In a preferred aspect, the genomic sequence includes isolated, purified, or recombinant polynucleotides comprising a contiguous span of at least 12, 15, 18, 20, 22, 25, 30, 35, 40, 50, 60, 70, 80, 90, 100, 150, 200, 500, 1000, 2000, 5000, 6000 or 7500 nucleotides of any one of the polynucleotide sequences described in SEQ ID NO:1, 2, or the complements thereof, wherein said contiguous span comprises a nucleotide sequence at least 90%, 91%, 92%, 93%, 94%, 95%, 96%, 97%, 98%, or 99% identical to the corresponding nucleotide sequence in SEQ ID NO: 1, 2, or 3. In further embodiments the polynucleotides are DNA, RNA, DNA/RNA hybrids, single-stranded, and double-stranded.

Further preferred are GSSP4 polynucleotides and polypeptides that have cholesterol regulating activies.

Further preferred are GSSP4 polynucleotides and polypeptides that have body weight regulating activies.

Further preferred are GSSP4 polynucleotides and polypeptides that have body fat regulating activies.

Further preferred are GSSP4 polynucleotides and polypeptides that have glucose regulating activies.

Further preferred are GSSP4 polynucleotides and polypeptides that have lipid regulating activies.

In a third aspect, the invention features a recombinant vector comprising, consisting essentially of, or consisting of, said polynucleotide described in the second aspect.

In a fourth aspect, the invention features a recombinant cell comprising, consisting essentially of, or consisting of, said recombinant vector described in the third aspect. A further embodiment includes a host cell recombinant for a polynucleotide of the invention.

In a fifth aspect, the invention features a pharmaceutical or physiologically acceptable composition comprising, consisting essentially of, or consisting of, said GSSP4 polypeptides described in the first aspect and, a pharmaceutical or physiologically acceptable diluent.

In a sixth aspect, the invention features a method of controlling cholesterol levels comprising, providing, or administering to individuals with said pharmaceutical or physiologically acceptable composition described in the fifth aspect or polynucleotides described in the second aspect.

In further preferred embodiments, the invention features a method of lowering body weight comprising, providing, or administering to individuals with said pharmaceutical or physiologically acceptable composition described in the fifth aspect or polynucleotides described in the second aspect.

In further preferred embodiments, the invention features a method of lowering body fat comprising, providing, or administering to individuals with said pharmaceutical or physiologically acceptable composition described in the fifth aspect or polynucleotides described in the second aspect.

In further preferred embodiments, the invention features a method of lowering controlling blood glucose comprising, providing, or administering to individuals with said pharmaceutical or physiologically acceptable composition described in the fifth aspect or polynucleotides described in the second aspect.

In a seventh aspect, the invention features a method of preventing or treating a metabolic-related disease or disorder comprising, providing or administering to an individual in need of such treatment said pharmaceutical or physiologically acceptable composition described in the fifth aspect or polynucleotides described in the second aspect. Preferably, said obesity-related disease or disorder is selected from the group consisting of obesity, impaired glucose tolerance (IGT), insulin resistance, atherosclerosis, atheromatous disease, heart disease, hypertension, stroke, Syndrome X, Non-insulin dependent diabetes mellitus (NIDDM or Type II diabetes), Insulin dependent diabetes mellitus (IDDM or Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure. In preferred embodiments, said individual is a mammal, preferably a human.

In a further preferred embodiment, a pharmaceutical or physiologically acceptable composition described in the fifth aspect or polynucleotides described in the second aspect suggest that a compound may have utility in alleviating insulin resistance in individuals, particularly those that are obese or overweight.

In a further preferred embodiment, the present invention may be used in complementary therapy in individuals to improve their cholesterol, weight or glucose level, comprising a pharmaceutical or physiologically acceptable composition described in the fifth aspect or polynucleotides described in the second aspect in combination with known agents.

The present invention further provides a method of improving the cholesterol levels, body weight or glucose control in individuals comprising the administration of said pharmaceutical or physiologically acceptable composition described in the fifth aspect or polynucleotides described in the second aspect alone, without known agents.

In a further preferred embodiment, the present invention may be administered either concomitantly or concurrently, with known agents for example in the form of separate dosage units to be used simultaneously, separately or sequentially (either before or after the known agent). Accordingly, the present invention further provides a product containing a composition a pharmaceutical or physiologically acceptable composition described in the fifth aspect or polynucleotides described in the second aspect and a known agent as a combined preparation for simultaneous, separate or sequential use for the improvement of cholesterol levels, body weight or glucose control in individuals, particularly those who are obese or overweight. The ratio of the present composition to known agent is such that the quantity of each active ingredient employed will be such as to provide a therapeutically effective level, but will not be larger than the quantity recommended as safe for administration.

In further preferred embodiments, the present invention of said pharmaceutical or physiologically acceptable composition described in the fifth aspect or polynucleotides described in the second aspect can be used as a method to improve insulin sensitivity in some persons, particularly those with Insulin Dependent Diabetes Mellitus (IDDM, Type I diabetes) or noninsulin dependent diabetics (Type II) in combination with insulin therapy.

In further preferred embodiments, the present invention of said pharmaceutical or physiologically acceptable composition described in the fifth aspect or polynucleotides described in the second aspect can be used as a method to improve insulin sensitivity in some persons, particularly those with Insulin Dependent Diabetes Mellitus (IDDM, Type I diabetes) or noninsulin dependent diabetes mellitus (NIDDM, Type II) in combination with alternate therapies.

In further preferred embodiments, the present invention of said pharmaceutical or physiologically acceptable composition described in the fifth aspect or polynucleotides described in the second aspect is used as a method in prophylaxis of long-term detrimental effects caused by prolonged high dosage of insulin in humans having IDDM or NIDDM.

In further preferred embodiments, the present invention of said pharmaceutical or physiologically acceptable composition described in the fifth aspect or polynucleotides described in the second aspect is used in therapeutics or methods for reducing or preventing hypersecretion of insulin and disorders or conditions resulting therefrom.

In further preferred embodiments, the present invention of said pharmaceutical or physiologically acceptable composition described in the fifth aspect or polynucleotides described in the second aspect is used in therapeutics or methods for reducing or preventing obesity and consequences or complications thereof.

In further preferred embodiments, the present invention of said pharmaceutical or physiologically acceptable composition described in the fifth aspect or polynucleotides described in the second aspect is used in therapeutics or methods for reducing or preventing hypercholesterolemia and consequences or complications thereof.

In further preferred embodiments, the present invention of said pharmaceutical or physiologically acceptable composition described in the fifth aspect or polynucleotides described in the second aspect is used in therapeutics or methods for reducing or preventing NIDDM or IDDM and consequences or complications thereof.

In further preferred embodiments, the present invention of said pharmaceutical or physiologically acceptable composition described in the fifth aspect or polynucleotides described in the second aspect is used in therapeutics or methods for reducing or preventing impaired glucose tolerance (IGT).

Further preferred embodiment thus provides therapeutics and methods for normalizing insulin resistance.

Further preferred embodiment thus provides therapeutics and methods for reducing, slowing or preventing the progression to NIDDM.

In further preferred embodiments, the present invention of said pharmaceutical or physiologically acceptable composition described in the fifth aspect or polynucleotides described in the second aspect is used in therapeutics or methods for reducing or preventing the appearance of insulin-resistance syndrome.

In further preferred embodiments, other conditions, particularly obesity, associated with insulin resistance are treated or prevented according to the methods of the invention. Thus, by preventing or treating obesity, the methods of the invention will allow an individual to have a more comfortable life and avoid the onset of various diseases triggered by obesity.

In further preferred embodiments, the target of the methods according to the present invention includes individuals with normal glucose tolerance (NGT) who are obese or who have fasting hyperinsulinemia, or who have both.

In an eighth aspect, the invention features a method of controlling blood free fatty acid (FFA) levels and lipid metabolism comprising, providing, or administering to individuals in need of increasing mobilization and utilization of fat stores and decreasing total fat stores with said pharmaceutical or physiologically acceptable composition described in the fifth aspect or polynucleotides described in the second aspect.

In a further preferred embodiment, the identification of said individuals in need of increasing mobilization and utilization of fat stores and decreasing total fat stores to be treated with said pharmaceutical or physiologically acceptable composition comprises a person who is involved in physical activity which increases metabolic demand. Furthermore, increasing mobilization and utilization of fat stores and decreasing total fat stores would provide a means to decrease body weight, preventing weight gain, decrease body fat in overweight and obese individuals. Reduction in weight and obesity will thus decrease the risk of chronic disease associated with obesity such as but not limited to the onset of various lipid metabolism disorders, hypertension, Type II diabetes, atherosclerosis, cardiovascular disease and stroke.

In related aspects, embodiments of the present invention includes methods of causing or inducing a desired biological response in an individual comprising the steps of: providing or administering to an individual a composition comprising a GSSP4 polypeptide, wherein said biological response is selected from the group consisting of:

(a) lowering circulating (either blood, serum, or plasma) levels (concentration) of free fatty acids;

(b) lowering circulating (either blood, serum or plasma) levels (concentration) of glucose;

(c) lowering circulating (either blood, serum or plasma) levels (concentration) of triglycerides;

(d) stimulating muscle lipid or free fatty acid oxidation;

(e) increasing leptin uptake in the liver or liver cells;

(f) reducing the postprandial increase in plasma free fatty acids, particularly following a high fat meal; and, (g) reducing or eliminating ketone body production, particularly following a high fat meal;

(h) increasing tissue sensitivity to insulin, particularly muscle, adipose, liver or brain, (i) reducing cholesterol levels, particularly in those with elevated cholesterol (ie. greater than 200 mg/dl);

(j) modulating circulating (either blood, serum or plasma) levels (concentration) of glucose within physiological range, preferably maintaining glucose between 60–190 mg/dl;

(k) modulating circulating (either blood, serum or plasma) levels (concentration) of FFA within physiological range preferably maintaining FFA between 190–420 mg/dl;

(l) modulating ketone body production as the result of a high fat meal, wherein said modulating is preferably reducing or eliminating;

(m) reducing body weight particularly in individuals with a BMI of greater than 27.

In a ninth aspect, the invention features a method of making the GSSP4 polypeptide described in the first aspect, wherein said method is selected from the group consisting of: proteolytic cleavage, recombinant methodology and artificial synthesis.

In a tenth aspect, the present invention provides a method of making a recombinant GSSP4 polypeptides, the method comprising providing a transgenic, non-human mammal whose milk contains said recombinant GSSP4 polypeptides, and purifying said recombinant GSSP4 polypeptides from the milk of said non-human mammal. In one embodiment, said non-human mammal is a cow, goat, sheep, rabbit, or mouse. In another embodiment, the method comprises purifying a recombinant GSSP4 polypeptides from said milk, and further comprises cleaving said protein in vitro to obtain a desired GSSP4 polypeptides.

In an eleventh aspect, the invention features a purified or isolated antibody capable of specifically binding to a protein comprising the sequence of one of the polypeptides of the present invention. In one aspect of this embodiment, the antibody is capable of binding to a polypeptide comprising at least 6 consecutive amino acids, at least 8 consecutive amino acids, or at least 10 consecutive amino acids of the sequence of one of the polypeptides of the present invention.

In a twelfth aspect, the invention features a use of polypeptides described in the first aspect or polynucleotides described in the second aspect for treatment of metabolic-related diseases and disorders or reducing or increasing body mass. Preferably, said metabolic-related disease or disorder is selected from the group consisting of obesity, impaired glucose tolerance (IGT), insulin resistance, atherosclerosis, atheromatous disease, heart disease, hypertension, stroke, Syndrome X, Noninsulin dependent diabetes mellitus (NIDDM or Type II diabetes), Insulin dependent diabetes mellitus (IDDM or Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure. In preferred embodiments, said individual is a mammal, preferably a human.

In a thirteenth aspect, the invention features a use of polypeptides described in the first aspect or polynucleotides described in the second aspect for the preparation of a medicament for the treatment of metabolic-related diseases and disorders or for reducing body mass. Preferably, said metabolic-related disease or disorder is selected from the group consisting of obesity, impaired glucose tolerance (IGT), insulin resistance, atherosclerosis, atheromatous disease, heart disease, hypertension, stroke, Syndrome X, Noninsulin dependent diabetes mellitus (NIDDM or Type II diabetes), Insulin dependent diabetes mellitus (IDDM or Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure. In preferred embodiments, said individual is a mammal, preferably a human.

In a fourteenth aspect, the invention provides polypeptides of the first aspect of the invention or a composition of the fifth aspect for use in a method of treatment of the human or animal body.

In a fifteenth aspect, the invention provides polynucleotides described in the second aspect or an acceptable composition thereof, for use in a method of treatment of the human or animal body. In a sixteenth aspect, the invention features methods of reducing body weight for cosmetic purposes comprising providing to an individual said pharmaceutical or physiologically acceptable composition described in the fifth aspect or polynucleotides described in the second aspect, or polypeptides described in the first aspect. Preferably, for said reducing body weight said individual has a BMI of at least 20, 25, 30, 35, or 40.

In a seventeenth aspect, the invention features the pharmaceutical or physiologically acceptable composition described in the fifth aspect or polynucleotides described in the second aspect or a polypeptide described in the first aspect for reducing body mass in said individuals with a BMI of at least 30, 35, 40, or 45 or for treatment or prevention of metabolic-related diseases or disorders. Preferably, said metabolic-related disease or disorder is selected from the group consisting of obesity, impaired glucose tolerance (IGT), insulin resistance, atherosclerosis, atheromatous disease, heart disease, hypertension, stroke, Syndrome X, Noninsulin dependent diabetes mellitus (NIDDM or Type II diabetes), Insulin dependent diabetes mellitus (IDDM or Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure. In preferred embodiments, said individual is a mammal, preferably a human.

In preferred embodiments, the identification of said individuals to be treated with said pharmaceutical or physiologically acceptable composition comprises genotyping GSSP4 single nucleotide polymorphisms (SNPs) or measuring GSSP4 polypeptide or mRNA levels in clinical samples from said individuals. Preferably, said clinical samples are selected from the group consisting of blood, serum, plasma, urine, and saliva.

In an eighteenth aspect, the invention features the pharmaceutical or physiologically acceptable composition described in the fifth aspect or polynucleotides described in the second aspect for reducing body weight for cosmetic reasons.

In further preferred embodiments, the invention features the pharmaceutical or physiologically acceptable composition described in the fifth aspect or polynucleotides described in the second aspect for reducing glucose levels.

In a nineteenth aspect, the invention features methods of treating insulin resistance comprising providing to an individual said pharmaceutical or physiologically acceptable composition described in the fifth aspect or polynucleotides described in the second aspect, or a polypeptide described in the first aspect.

BRIEF DESCRIPTION OF THE SEQUENCES

SEQ ID NO:1 shows GSSP4 genomic sequence indicating regulatory regions, exons, polymorphic alleles and positions, and reverse and forward microsequencing primers for haplotyping.

SEQ ID NO:2 shows GSSP4 polynucleotide sequence of cDNA

SEQ ID NO:3 shows GSSP4 polypeptide sequence

SEQ ID NO:4–18 shows GSSP4 47-mer nucleotide sequence comprising polymorphic allele at position 24. The corresponding alleles and primers indicated in SEQ ID NO:1 are as follows:

```
VLP_1206_C_A,  m = C or A       SEQ ID NO:4
VLP_148_A_G,   r = A or G       SEQ ID NO:5
VLP_1851_T_C,  y = T or C       SEQ ID NO:6
VLP_2551_G_A,  r = G or A       SEQ ID NO:7
VLP_3124_C_T,  y = C or T       SEQ ID NO:8
VLP_3563_G_A,  r = G or A       SEQ ID NO:9
VLP_3792_G_A,  r = G or A       SEQ ID NO:10
VLP_4417_A_C,  m = A or G       SEQ ID NO:11
VLP_5757_T_C,  y = T or C       SEQ ID NO:12
VLP_6322_A_G,  r = G or A       SEQ ID NO:13
VLP_816_G_A,   r = G or A       SEQ ID NO:14
VLP_924_G_A,   r = G or A       SEQ ID NO:15
VLP_99-1_174_T_C, y = T or C    SEQ ID NO:16
VLP_99-1_325_C_G, s = C or G    SEQ ID NO:17
VLP_99-2_389_T_C, y = T or G    SEQ ID NO:18
```

DETAILED DESCRIPTION OF THE INVENTION

Before describing the invention in greater detail, the following definitions are set forth to illustrate and define the meaning and scope of the terms used to describe the invention herein.

As used interchangeably herein, the terms "oligonucleotides", and "polynucleotides" and nucleic acid include RNA, DNA, or RNA/DNA hybrid sequences of more than one nucleotide in either single chain or duplex form. The terms encompass "modified nucleotides" which comprise at least one modification, including by way of example and not limitation: (a) an alternative linking group, (b) an analogous form of purine, (c) an analogous form of pyrimidine, or (d) an analogous sugar. For examples of analogous linking groups, purines, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

The terms polynucleotide construct, recombinant polynucleotide and recombinant polypeptide are used herein consistently with their use in the art. The terms "upstream" and "downstream" are also used herein consistently with their use in the art. The terms "base paired" and "Watson & Crick base paired" are used interchangeably herein and consistently with their use in the art. Similarly, the terms "complementary", "complement thereof", "complement", "complementary polynucleotide", "complementary nucleic acid" and "complementary nucleotide sequence" are used interchangeably and consistently with their use in the art.

The term "purified" is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). Purified can also refer to the separation of covalently closed polynucleotides from linear polynucleotides, or vice versa, for example. A polynucleotide is substantially pure when at least about 50%, 60%, 75%, or 90% of a sample contains a single polynucleotide sequence. In some cases this involves a determination between conformations (linear versus covalently closed). A substantially pure polynucleotide typically comprises about 50, 60, 70, 80, 90, 95, 99% weight/weight of a nucleic acid sample. Polynucleotide purity or homogeneity may be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

Similarly, the term "purified" is used herein to describe a polypeptide of the invention that has been separated from other compounds including, but not limited to, nucleic acids, lipids, carbohydrates and other proteins. In some preferred embodiments, a polypeptide is substantially pure when at least about 50%, 60%, 75%, 85%, 90%, 95%, 96%, 97%, 98%, 99%, or 99.5% of the polypeptide molecules of a sample have a single amino acid sequence. In some preferred embodiments, a substantially pure polypeptide typically comprises about 50%, 60%, 70%, 80%, 90% 95%, 96%, 97%, 98%, 99% or 99.5% weight/weight of a protein sample. Polypeptide purity or homogeneity is indicated by a number of methods well known in the art, such as agarose or polyacrylamide gel electrophoresis of a sample, followed by visualizing a single polypeptide band upon staining the gel. For certain purposes higher resolution can be provided by using HPLC or other methods well known in the art.

Further, as used herein, the term "purified" does not require absolute purity; rather, it is intended as a relative definition. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both) or polypeptides. As a preferred embodiment, the polynucleotides or polypeptides of the present invention are at least; 10%, 20%, 30%, 40%, 50%, 60%, 70%, 80%, 90%, 95%, 96%, 96%, 98%, 99%, 99.5% or 100% pure relative to heterologous polynucleotides or polypeptides. As a further preferred embodiment the polynucleotides or polypeptides have an "at least" purity ranging from any number, to the thousandth position, between 90% and 100% (e.g., at least 99.995% pure) relative to heterologous polynucleotides or polypeptides. Additionally, purity of the polynucleotides or polypeptides may be expressed as a percentage (as described above) relative to all materials and compounds other than the carrier solution. Each number, to the thousandth position, may be claimed as individual species of purity.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

Specifically excluded from the definition of "isolated" are: naturally occurring chromosomes (e.g., chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a 5' EST makes up less than 5% (or alternatively 1%, 2%, 3%, 4%, 10%, 25%, 50%, 75%, or 90%, 95%, or 99%) of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

The term "primer" denotes a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment (or nucleotide analog segment, e.g., PNA as defined hereinbelow) which can be used to identify a specific polynucleotide sequence present in a sample, said nucleic acid segment comprising a nucleotide sequence complementary to the specific polynucleotide sequence to be identified.

The term "polypeptide" refers to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The phrases "control of blood glucose", "glucose regulation" "regulation of blood glucose", "modulating blood glucose", and "glucose control" refer to maintaining or regulating blood, serum, and plasma levels of glucose between 70–190 mg/dl. Without being limited by theory, the compounds/polypeptides of the invention feature a method of chronic control of blood glucose within a narrow and more physiological range compared to the control of blood glucose attained with current therapies which treat disorders of glucose metabolism or insulin action, including but not limited to hyperglycemia, insulin resistance, insulin dependent diabetes mellitus and noninsulin dependent diabetes mellitus.

Without being limited by theory, the compounds/polypeptides of the invention are capable of modulating the control of blood glucose (as defined above), directing or partitioning glucose between the liver and the peripheral tissues, and are thus believed to treat "diseases involving the control of blood glucose between the liver and peripheral tissues". The term "peripheral tissues" is meant to include the blood, brain, muscle and adipose tissue. In preferred embodiments, the compounds/polypeptides of the invention direct or partition glucose towards the liver, muscle and brain. In alternative preferred embodiments, glucose is directed or partitioned towards the adipose tissue. In other preferred embodiments, glucose is directed or partitioned towards the liver. In other preferred embodiments, glucose is directed or partitioned towards the brain. In other preferred embodiments, glucose is directed towards the blood. In yet other preferred embodiments, the compounds/polypeptides of the invention increase or decrease the oxidation of glucose, preferably by the muscle.

Without being limited by theory, the compounds/polypeptides of the invention are capable of modulating the partitioning of dietary or endogenous lipids between the liver and peripheral tissues, and are thus believed to treat "diseases involving the partitioning of lipids between the liver and peripheral tissues." The term "peripheral tissues" is meant to include the blood, muscle and adipose tissue. In preferred embodiments, the compounds/polypeptides of the invention partition the lipids toward the muscle. In alternative preferred embodiments, the lipids are partitioned toward the blood. In alternative preferred embodiments, the lipids are partitioned toward the adipose tissue. In other preferred embodiments, the lipids are partitioned toward the liver. In yet other preferred embodiments, the compounds/polypeptides of the invention increase or decrease the oxidation of dietary or endogenous lipids, preferably free fatty acids (FFA) by the muscle. Dietary and endogenous lipids include, but are not limited to triglycerides (TG) and FFA.

"Preferred diseases" believed to involve the the control of cholesterol, body fat, lipid metabolism, blood glucose, partitioning of blood glucose, and partitioning of lipids include obesity, impaired glucose tolerance (IGT), insulin resistance, atherosclerosis, atheromatous disease, heart disease, hypertension, stroke, reproductive cancers, hypercortisolism, aldosteronism, hyperandrogenism, hyperkalemia, hypernatremia, hyperlipoproteinemia, hyperinsulinemia, hyperglycemia, Syndrome X, Noninsulin dependent diabetes mellitus (NIDDM, Type II diabetes), Insulin dependent diabetes mellitus (IDDM, Type I diabetes), diabetes-related complications (eg. ketosis), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be prevented or treated by the methods of the invention. Heart disease includes, but is not limited to, cardiac insufficiency, coronary insufficiency, and high blood pressure. The term "heterologous", when used herein, is intended to designate any polypeptide or polynucleotide other than a GSSP4 polypeptide or a polynucleotide encoding a GSSP4 polypeptide of the present invention.

The terms "comprising", "consisting of" and "consisting essentially of" are defined according to their standard meaning. A defined meaning set forth in the M.P.E.P. controls over a defined meaning in the art and a defined meaning set forth in controlling Federal Circuit case law controls over a meaning set forth in the M.P.E.P. With this in mind, the terms may be substituted for one another throughout the instant application in order to attach the specific meaning associated with each term.

The term "host cell recombinant for" a particular polynucleotide of the present invention, means a host cell that has been altered by the hands of man to contain said polynucleotide in a way not naturally found in said cell. For example, said host cell may be transiently or stably transfected or transduced with said polynucleotide of the present invention.

The term "obesity" as used herein is defined by the National Heart, Lung and Blood Institute Expert Panel (J Amer Diet Assoc 98:1178–1191, 1998) based on Body Mass Index (BMI). BMI is calculated as body weight in kilograms divided by the square of height in meters, ie $kg/m^2$. A BMI of less than 18.5 $kg/m^2$ is considered "Underweight"; a BMI of 18.5–24.9 $kg/m^2$ is considered "Normal" (healthy); a BMI of 25.0–29.9 $kg/m^2$ is considered "Overweight"; a BMI of 30.0–34.9 $kg/m^2$ is considered "Class I Obesity"; a BMI of 35.0–39.9 $kg/m^2$ is considered "Class II Obesity"; a BMI of greater than 39.9 $kg/m^2$ is considered "Class III Obesity". Waist circumference can also be used to indicate a risk of metabolic complications where in men a circumference of greater than or equal to 94 cm indicates an increased risk, and greater than or equal to 102 cm indicates a substantially increased risk Similarly for women, greater than or equal to 88 cm indicates an increased risk, and greater than or equal to 88 cm indicates a substantially increased risk. The waist circumference is measured in cm at midpoint between lower border of ribs and upper border of the pelvis. Other measures of obesity include, but are not limited to, skinfold thickness which is a measurement in cm of skinfold thickness using calipers and bioimpedance which is based on the principle that lean mass and water will conduct electrical current and measurement of resistance to a weak current (impedance) applied across extremities provides an estimate of body fat using an empirically derived equation.

The term "Insulin Dependent Diabetes Mellitus", "IDDM", "Type I Diabetes" and "Type I diabetics" are synomous, inclusive, or interchangable.

The term "diabetes-related complications" refer to pathologic or physiologic states experienced by Type I diabetics (as defined previously) or Type II diabetics (as defined previously) or both.

The term "Noninsulin Dependent Diabetes Mellitus", "NIDDM", "Type II Diabetes" and "Type II diabetics" are synomous, inclusive, or interchangable.

The term "agent acting on the control of blood glucose, directing glucose between the liver and peripheral tissues" refers to a compound or polypeptide of the invention that modulates the control of blood glucose as previously described. Preferably, the agent increases or decreases the oxidation of glucose, preferably by the muscle. Preferably the agent decreases or increases the body weight of individuals or is used to treat or prevent an metabolic-related disease or disorder such as obesity, impaired glucose tolerance (IGT), insulin resistance, atherosclerosis, atheromatous disease, heart disease, hypertension, stroke, Syndrome X, Noninsulin dependent diabetes mellitus (NIDDM, Type II diabetes), Insulin dependent diabetes mellitus (IDDM, Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure.

The terms "response to an agent acting on the control of blood glucose, directing glucose between the liver and peripheral tissues" refer to drug efficacy, including but not limited to, ability to metabolize a compound, ability to convert a pro-drug to an active drug, and the pharmacokinetics (absorption, distribution, elimination) and the pharmacodynamics (receptor-related) of a drug in an individual.

The terms "side effects to an agent acting on the control of blood glucose, directing glucose between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

The term "agent acting on the partitioning of glucose between the liver and peripheral tissues" refers to a compound or polypeptide of the invention that modulates the partitioning of glucose between the liver and the peripheral tissues as previously described. Preferably, the agent increases or decreases blood glucose levels. Preferably, the agent increases or decreases oxidation of glucose, preferably by the muscle. Preferably the agent decreases or increases the body weight of individuals or is used to treat or prevent an metabolic-related disease or disorder such as obesity, impaired glucose tolerance (IGT), insulin resistance, atherosclerosis, atheromatous disease, heart disease, hypertension, stroke, Syndrome X, Noninsulin dependent diabetes mellitus (NIDDM, Type II diabetes), Insulin dependent diabetes mellitus (IDDM, Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure.

The terms "response to an agent acting on the partitioning of glucose between the liver and peripheral tissues" refer to drug efficacy, including but not limited to, ability to metabolize a compound, ability to convert a pro-drug to an active drug, and the pharmacokinetics (absorption, distribution, elimination) and the pharmacodynamics (receptor-related) of a drug in an individual.

The terms "side effects to an agent acting on the partitioning of glucose between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

The term "agent acting on the partitioning of dietary lipids between the liver and peripheral tissues" refers to a compound or polypeptide of the invention that modulates the partitioning of dietary lipids between the liver and the peripheral tissues as previously described. Preferably, the agent increases or decreases the oxidation of dietary lipids, preferably free fatty acids (FFA) by the muscle. Preferably the agent decreases or increases the body weight of individuals or is used to treat or prevent an metabolic-related disease or disorder such as obesity, impaired glucose tolerance (IGT), insulin resistance, atherosclerosis, atheromatous disease, heart disease, hypertension, stroke, Syndrome X, Noninsulin dependent diabetes mellitus (NIDDM, Type II diabetes), Insulin dependent diabetes mellitus (IDDM, Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure.

The terms "response to an agent acting on the partitioning of dietary lipids between the liver and peripheral tissues" refer to drug efficacy, including but not limited to, ability to metabolize a compound, ability to convert a pro-drug to an active drug, and the pharmacokinetics (absorption, distribution, elimination) and the pharmacodynamics (receptor-related) of a drug in an individual.

The terms "side effects to an agent acting on the partitioning of dietary lipids between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

The term "agent acting on the partitioning of endogenous lipids between the liver and peripheral tissues" refers to a compound or polypeptide of the invention that modulates the partitioning of endogenous lipids between the liver and the peripheral tissues as previously described. Preferably, the agent increases or decreases the oxidation of endogenous lipids, preferably free fatty acids (FFA) by the muscle. Preferably the agent decreases or increases the body weight of individuals or is used to treat or prevent an metabolic-related disease or disorder such as obesity, impaired glucose tolerance (IGT), insulin resistance, atherosclerosis, atheromatous disease, heart disease, hypertension, stroke, Syndrome X, Noninsulin dependent diabetes mellitus (NIDDM, Type II diabetes), Insulin dependent diabetes mellitus (IDDM, Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure.

The terms "response to an agent acting on the partitioning of endogenous lipids between the liver and peripheral tissues" refer to drug efficacy, including but not limited to, ability to metabolize a compound, ability to convert a pro-drug to an active drug, and the pharmacokinetics (absorption, distribution, elimination) and the pharmacodynamics (receptor-related) of a drug in an individual.

The terms "side effects to an agent acting on the partitioning of endogenous lipids between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of endogenous lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

The term "GSSP4-related diseases and disorders" as used herein refers to any disease or disorder comprising an aberrant functioning of a GSSP4, or which could be treated or prevented by modulating GSSP4 levels or activity. "Aberrant functioning of a GSSP4" includes, but is not limited to, aberrant levels of expression of a GSSP4 polypeptide (either increased or decreased, but preferably decreased), aberrant activity of a GSSP4 polypeptide (either increased or decreased), and aberrant interactions with ligands or binding partners (either increased or decreased). By "aberrant" is meant a change from the type, or level of activity seen in normal cells, tissues, or patients, or seen previously in the cell, tissue, or patient prior to the onset of the illness. In preferred embodiments, these GSSP4-related diseases and disorders include obesity and the metabolic-related diseases and disorders described previously.

The term "cosmetic treatments" is meant to include treatments with compounds or polypeptides of the invention that increase or decrease the body mass of an individual where the individual is not clinically obese or clinically underweight as defined previously. Thus, these individuals have a body mass index (BMI) below the cut-off for clinical obesity (e.g. below 30 kg/m$^2$) and above the cut-off for clinical thinness (e.g. above 18.5 kg/m$^2$). In addition, these individuals are preferably healthy (e.g. do not have an metabolic-related disease or disorder of the invention). "Cosmetic treatments" are also meant to encompass, in some circumstances, more localized increases in adipose tissue, for example, gains or losses specifically around the waist or hips, or around the hips and thighs, for example. These localized gains or losses of adipose tissue can be identified by increases or decreases in waist or hip size, for example.

The term "prevent" or "preventing" as used herein refers to administering a compound prior to the onset of clinical symptoms of a disease or condition so as to prevent a physical manifestation of aberrations associated with obesity or insulin resistance to some extent. The term "prevent" or "preventing" does not mean the result is necessarily absolute, but rather effective for providing some degree of prevention or amelioration of the progression of the metabolic or GSSP4-related disorder (i.e., provide protective effects), amelioration of the symptoms of the disorder, and amelioration of the reoccurrence of the metabolic or GSSP4-related disorder.

The term "treat" or "treating" as used herein refers to administering a compound after the onset of clinical symptoms. The term "treat" or "treating" means to ameliorate, alleviate symptoms, eliminate the causation of the symptoms either on a temporary or permanent basis, or to prevent or slow the appearance of symptoms of the named disorder or condition.

The term "in need of treatment" as used herein refers to a judgment made by a caregiver (e.g. physician, nurse, nurse practitioner, etc in the case of humans; veterinarian in the case of animals, including non-human mammals) that an individual or animal requires or will benefit from treatment. This judgment is made based on a variety of factors that are in the realm of a caregiver's expertise, but that include the knowledge that the individual or animal is ill, or will be ill, as the result of a condition that is treatable by the compounds of the invention.

The term "perceives a need for treatment" refers to a sub-clinical determination that an individual desires to reduce weight for cosmetic reasons as discussed under "cosmetic treatment" above. The term "perceives a need for treatment" in other embodiments can refer to the decision that an owner of an animal makes for cosmetic treatment of the animal.

The term "patient" or "individual" as used herein refers to any animal, including mammals, preferably mice, rats, other rodents, rabbits, dogs, cats, swine, cattle, sheep, horses, or primates, and most preferably humans. The term may specify male or female or both, or exclude male or female.

The term "non-human animal" refers to any non-human vertebrate, including birds and more usually mammals, preferably primates, animals such as swine, goats, sheep, donkeys, horses, cats, dogs, rabbits or rodents, more preferably rats or mice. Both the terms "animal" and "mammal" expressly embrace human subjects unless preceded with the term "non-human".

The inventors believe GSSP4 polypeptides are able to significantly reduce the postprandial response of glucose in an individual, particularly following a high fat/high carbohydrate meal, while not effecting the levels of insulin. Further, GSSP4 polypeptides of the invention are believed to modulate weight gain, particularly in individuals are fed a high fat/high carbohydrate diet.

The instant invention encompasses the use of GSSP4 polypeptides in the modulation of glucose as an important new tool to control energy homeostasis and glucose regulation.

The instant invention encompasses the use of GSSP4 polypeptides in the partitioning of glucose as an important new tool to control energy homeostasis and glucose regulation.

The instant invention encompasses the use of GSSP4 polypeptides in the partitioning of lipids as an important new tool to control energy homeostasis and lipid regulation.

The instant invention encompasses the use of GSSP4 polypeptides in the partitioning of dietary lipids as an important new tool to control energy homeostasis and lipid regulation.

The instant invention encompasses the use of GSSP4 polypeptides in the partitioning of endogenous lipids as an important new tool to control energy homeostasis and lipid regulation.

PREFERRED EMBODIMENTS OF THE INVENTION

I. GSSP4 Polypeptides of the Invention

GSSP4 polypeptides that have measurable activity in vitro and in vivo have been identified. These activities include, but are not limited to, reduction of the postprandial response of plasma free fatty acids, glucose, and triglycerides, particularly in mice fed a high fat/carbohydrate meal, increase in muscle free fatty acid oxidation in vitro and ex vivo, and sustained weight loss in mice on a high fat/carbohydrate diet. Other assays for GSSP4 polypeptide activity in vitro and in vivo are also provided (Examples 2–13, for example), and equivalent assays can be designed by those with skill in the art.

The term "obesity-related" or "metabolic-related" activity as used herein refers to at least one, and preferably all, of the activities described herein for GSSP4 polypeptides. Assays for the determination of these activities are provided herein, and equivalent assays can be designed by those with ordinary skill in the art. The term "metabolic-related activity" as used herein refers to at least one, and preferably all, of the activities described herein for GSSP4 polypeptides. Assays for the determination of these activities are provided herein, known in the art, or can be designed by those with ordinary skill in the art. Optionally, "metabolic-related activity" can be selected from the group consisting of control of blood glucose, partitioning of glucose, glucose metabolism, lipid partitioning, lipid metabolism, and insulin-like activity, or an activity within one of these categories. Optionally, "obesity-related" activity can be selected from the group consisting of lipid partitioning, lipid metabolism, and insulin-like activity, or an activity within one of these categories. By "lipid partitioning" activity is meant the ability to effect the location of dietary lipids among the major tissue groups including, adipose tissue, liver, and muscle. The inventors have shown that GSSP4 polypeptides of the invention play a role in the partitioning of lipids to the muscle, liver or adipose tissue. By "lipid metabolism" activity is meant the ability to influence the metabolism of lipids. The inventors have shown that GSSP4 polypeptides of the invention have the ability to affect the level of free fatty acids in the plasma as well as to increase the metabolism of lipids in the muscle through free fatty acid oxidation experiments (Examples 4, 8, 10, 11, and 12) and to transiently affect the levels of triglycerides in the plasma and the muscle (Examples 7, 10, and 13). By "insulin-like" activity is meant the ability of GSSP4 polypeptides to modulate the levels of glucose in the plasma. The inventors have found that GSSP4 polypeptides do not significantly impact insulin levels but do impact glucose levels similarly to the effects of insulin (Examples 9 & 10). These effects are not seen in the presence of the intact (full-length) GSSP4 polypeptide or are significantly greater in the presence of the GSSP4 polypeptides compared with the full-length GSSP4 polypeptide.

By "intact" or "full-length" GSSP4 polypeptide as used herein is meant the full length polypeptide sequence of the GSSP4 polypeptide of SEQ ID NO:3, from the N-terminal methionine to the C-terminal stop codon. Preferred GSSP4 polypeptides have a biological activity described herein, and as they would be useful in making antibodies, diagnostic assays, etc.

As a further preferred embodiment, GSSP4 polypeptides which allow a rise in plasma glucose to not more than 190 mg/dl, particularly following consumption of food, or which prevent a drop in serum glucose to not less than 70 mg/dl, particularly following consumption of food.

As a further preferred embodiment, GSSP4 polypeptides which allow a rise in plasma fatty acids to not more than 420 mg/dl, particularly following consumption of food, or which prevent a drop in serum fatty acids to not less than 190 mg/dl, particularly following consumption of food.

By "significantly" as used herein is meant statistically significant as it is typically determined by those with ordinary skill in the art. For example, data are typically calculated as a mean±SEM, and a p-value$\leq$0.05 is considered statistically significant. Statistical analysis is typically done using either the unpaired Student's t test or the paired Student's t test, as appropriate in each study.

Representative "metabolic-related assays" are provided in Examples below. These assays include, but are not limited to, in vivo and in vitro methods of measuring the postprandial response, methods of measuring glucose uptake, glucose oxidation, glucose concentration, lipid concentration, free fatty acid levels, fatty acid oxidation and methods of measuring weight modulation. In preferred embodiments, the post-prandial response is measured in non-human animals, preferably rodents. In preferred embodiments physiologic parameters are measured including, but not limited to, levels of glucose, fatty acids, insulin, and leptin. In other preferred embodiments, free fatty acid oxidation is measured in cells in vitro or ex vivo, preferably in muscle cells or tissue of non-human animals, preferably rodents. In yet other preferred embodiments weight modulation is measured in human or non-human animals, preferably rodents (rats or mice), primates, canines, felines or procines on a high fat/carbohydrate diet. Optionally, "metabolic-related activity" includes other activities not specifically identified herein. In general, "measurable parameters" relating to obesity and the field of metabolic research can be selected from the group consisting of free fatty acid levels, free fatty acid oxidation, triglyceride levels, glucose levels, insulin levels, leptin levels, food intake, and body weight.

In these metabolic-related assays, preferred GSSP4 polypeptides or polynucleotides or both would cause a significant change in at least one of the measurable parameters selected from the group consisting of post-prandial lipemia, free fatty acid levels, triglyceride levels, glucose levels, glucose oxidation, glucose uptake, free fatty acid oxidation, and weight. Alternatively, preferred GSSP4 polypeptides or polynucleotides or both would have a significant change in at least one of the measurable parameters selected from the group consisting of an increase in blood fatty acid levels (FFA), an decrease in blood glucose levels, a decrease in insulin levels, an increase in glucose oxidation and an increase in FFA oxidation.

The invention is drawn, inter alia, to isolated, purified or recombinant GSSP4 polypeptides. GSSP4 polypeptides of the invention are useful for treating or preventing insulin resistance, and reducing body weight or increasing body weight (using antagonists of GSSP4 polypeptides) either as a cosmetic treatment or for treatment or prevention of metabolic-related diseases and disorders. GSSP4 polypeptides are also useful inter alia in screening assays for agonists or antagonists of GSSP4 polypeptide activity, for raising GSSP4 polypeptide-specific antibodies, and in diagnostic assays.

The GSSP4 polypeptides of the present invention are preferably provided in an isolated form, and may be partially or substantially purified. A recombinantly produced version of any one of the GSSP4 polypeptides can be substantially purified by the one-step method described by Smith et al. ((1988) Gene 67(1):31–40) or by the methods described herein or known in the art. Polypeptides of the invention also can be purified from natural or recombinant sources using antibodies directed against the polypeptides of the invention by methods known in the art of protein purification.

Preparations of GSSP4 polypeptides of the invention involving a partial purification of or selection for the GSSP4 polypeptides are also specifically contemplated. These crude preparations are envisioned to be the result of the concentration of cells expressing GSSP4 polypeptides with perhaps a few additional purification steps, but prior to complete purification of the polypeptides. The cells expressing GSSP4 polypeptides are present in a pellet, they are lysed, or the crude polypeptide is lyophilized, for example.

GSSP4 polypeptides can be any integer in length from at least 6 consecutive amino acids to 1 amino acids less than a full length GSSP4 polypeptide of SEQ ID NO:4. Thus, for SEQ ID NO:4, a GSSP4 polypeptide can be: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, or 105 consecutive amino acids.

Each GSSP4 polypeptide as described above can be further specified in terms of its N-terminal and C-terminal positions. For example, every combination of a N-terminal and C-terminal position that polypeptides of from 6 contiguous amino acids to 1 amino acids less than the full length GSSP4 polypeptide could occupy, on any given intact and contiguous full length GSSP4 polypeptide sequence are included in the present invention. Thus, a 6 consecutive amino acid fragment could occupy positions selected from the group consisting of 1–6, 2–7, 3–8, 4–9, 5–10, 6–11, 7–12, 8–13, 9–14, 10–15, 11–16, 12–17, 13–18, 14–19, 15–20, 16–21, 17–22, 18–23, 19–24, 20–25, 21–26, 22–27, 23–28, 24–29, 25–30, 26–31, 27–32, 28–33, 29–34, 30–35, 31–36, 32–37, 33–38, 34–39, 35–40, 36–41, 37–42, 38–43, 39–44, 40–45, 41–46, 42–47, 43–48, 44–49, 45–50, 46–51, 47–52, 48–53, 49–54, 50–55, 51–56, 52–57, 53–58, 54–59, 55–60, 56–61, 57–62, 58–63, 59–64, 60–65, 61–66, 62–67, 63–68, 64–69, 65–70, 66–71, 67–72, 68–73, 69–74, 70–75, 71–76, 72–77, 73–78, 74–79, 75–80, 76–81, 77–82, 78–83, 79–84, 80–85, 81–86, 82–87, 83–88, 84–89, 85–90, 86–91, 87–92, 88–93, 89–94, 90–95, 91–96, 92–97, 93–98, 94–99, 95–100, 96–101, 97–102, 98–103, 99–104, and 100–105, of a 105 consecutive amino acid fragment. Similarly, the positions occupied by all the other fragments of sizes between 6 amino acids and 105 amino acids of SEQ ID NO:3 are included in the present invention and can also be immediately envisaged based on these two examples and therefore, are not individually listed solely for the purpose of not unnecessarily lengthening the specification. Furthermore, the positions occupied by fragments of 6 to 105 consecutive amino acids of SEQ ID NO:3 are included in the present invention and can also be immediately envisaged based on these two examples and therefore are not individually listed solely for the purpose of not unnecessarily lengthening the specification. In addition, the positions occupied by fragments of 6 consecutive amino acids to 1 amino acid less than any other full length GSSP4 polypeptide can also be envisaged based on these two examples and therefore are not individually listed solely for the purpose of not unnecessarily lengthening the specification.

The GSSP4 polypeptides of the present invention may alternatively be described by the formula "n to c" (inclusive); where "n" equals the N-terminal most amino acid position (as defined by the sequence listing) and "c" equals the C-terminal most amino acid position (as defined by the sequence listing) of the polypeptide; and further where "n" equals an integer between 1 and 99; and where "c" equals an integer between 7 and 105, the number of amino acids of the full length polypeptide sequence; and where "n" is an integer smaller then "c" by at least 6. Therefore, for the sequences provided in SEQ ID NO:3, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99; and "c" is any integer selected from the group consisting of: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, and 105. Every combination of "n" and "c" positions are included as specific embodiments of the invention. Moreover, the formula "n" to "c" may be modified as "'n1–n2" to "c1–c2"', wherein "n1–n2" and "c1–c2" represent positional ranges selected from any two integers above which represent amino acid positions of the sequence listing. Alternative formulas include "'n1–n2" to "c"' and "'n" to "c1–c2"'.

These specific embodiments, and other polypeptide and polynucleotide fragment embodiments described herein may be modified as being "at least", "equal to", "equal to or less than", "less than", "at least _____ but not greater than _____" or "from _____ to _____". a specified size or specified N-terminal and/or C-terminal positions. It is noted that all ranges used to describe any embodiment of the present invention are inclusive unless specifically set forth otherwise.

The present invention also provides for the exclusion of any individual fragment specified by N-terminal and C-terminal positions or of any fragment specified by size in amino acid residues as described above. In addition, any number of fragments specified by N-terminal and C-terminal positions or by size in amino acid residues as described above may be excluded as individual species. Further, any number of fragments specified by N-terminal and C-terminal positions or by size in amino acid residues as described above may make up a polypeptide fragment in any combination and may optionally include non-GSSP4 polypeptide sequence as well.

The term "GSSP4 fragment" as used herein refers to fragments of a full-length GSSP4 polypeptides that comprise at least 6 and any other integer number of amino acids up to 104 of the full-length GSSP4 polypeptide (defined above). GSSP4 polypeptides of the invention include variants, fragments, analogs and derivatives of the GSSP4 polypeptides described above, including modified GSSP4 polypeptides.

Variants

It will be recognized by one of ordinary skill in the art that some amino acids of the GSSP4 polypeptide sequences of the present invention can be varied without significant effect on the structure or function of the proteins; there will be critical amino acids in the sequence that determine activity. Thus, the invention further includes variants of GSSP4 polypeptides that have metabolic-related activity as described above. Such variants include GSSP4 polypeptide sequences with one or more amino acid deletions, insertions, inversions, repeats, and substitutions either from natural mutations or human manipulation selected according to general rules known in the art so as to have little effect on activity. Guidance concerning how to make phenotypically silent amino acid substitutions is provided below.

There are two main approaches for studying the tolerance of an amino acid sequence to change (see, Bowie, et al. (1990) Science, 247, 1306–10). The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions and indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged.

In particular embodiments, conservative substitutions of interest are shown in Table 1 under the heading of preferred substitutions. If such substitutions result in a change in biological activity, then more substantial changes, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gin; asn | lys |
| Asn (N) | gin; his; lys; arg | gin |
| Asp (D) | glu | glu |
| Cys (C) | ser | ser |
| Gin (Q) | asn | asn |
| Glu (E) | asp | asp |
| Gly (G) | pro; ala | ala |
| His (H) | asn; gin; lys; arg | arg |
| Ile (I) | leu; val; met; ala; phe; norleucine | leu |
| Leu (L) | norleucine; ile; val; met; ala; phe | ile |
| Lys (K) | arg; gin; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the GSSP4 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the GSSP4 variant DNA.

Amino acids in the GSSP4 polypeptide sequences of the invention that are essential for function can also be identified by methods known in the art, such as site-directed mutagenesis or alanine-scanning mutagenesis (see, e.g., Cunningham, et al. (1989) Science 244(4908):1081–5). The latter procedure introduces single alanine mutations at every residue in the molecule. The resulting mutant molecules are then tested for metabolic-related activity using assays as described above. Of special interest are substitutions of charged amino acids with other charged or neutral amino acids that may produce proteins with highly desirable improved characteristics, such as less aggregation. Aggregation may not only reduce activity but also be problematic when preparing pharmaceutical or physiologically acceptable formulations, because aggregates can be immunogenic (see, e.g., Pinckard, et al., (1967) Clin. Exp. Immunol 2:331–340; Robbins, et al., (1987) Diabetes July;36(7): 838–41; and Cleland, et al., (1993) Crit Rev Ther Drug Carrier Syst. 10(4):307–77).

Thus, the fragment, derivative, analog, or homolog of the GSSP4 polypeptides of the present invention may be, for example: (i) one in which one or more of the amino acid residues are substituted with a conserved or non-conserved amino acid residue (preferably a conserved amino acid residue) and such substituted amino acid residue may or may not be one encoded by the genetic code (i.e. may be a non-naturally occurring amino acid); or (ii) one in which one or more of the amino acid residues includes a substituent group; or (iii) one in which the GSSP4 polypeptide is fused with another compound, such as a compound to increase the half-life of the fragment (for example, polyethylene glycol); or (iv) one in which the additional amino acids are fused to the above form of the fragment, such as an IgG Fc fusion region peptide or leader or secretory sequence or a sequence which is employed for purification of the above form of the fragment or a pro-protein sequence. Such fragments, derivatives and analogs are deemed to be within the scope of those skilled in the art from the teachings herein.

A further embodiment of the invention relates to a polypeptide which comprises the amino acid sequence of GSSP4 polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a GSSP4 fragment, having at least one, but not more than 10, 9, 8, 7, 6, 5, 4, 3, 2 or 1 conservative amino acid substitutions.

Another specific embodiment of a modified GSSP4 polypeptide of the invention is a polypeptide that is resistant to proteolysis, for example a GSSP4 polypeptide in which a —CONH— peptide bond is modified and replaced by one or more of the following: a (CH2NH) reduced bond; a (NHCO) retro inverso bond; a (CH2-O) methylene-oxy bond; a (CH2-S) thiomethylene bond; a (CH2CH2) carba bond; a (CO—CH2) cetomethylene bond; a (CHOH—CH2) hydroxyethylene bond); a (N—N) bound; a E-alcene bond; or a —CH=CH— bond. Thus, the invention also encompasses a GSSP4 polypeptide or a variant thereof in which at least one peptide bond has been modified as described above.

In addition, amino acids have chirality within the body of either L or D. In some embodiments it is preferable to alter the chirality of the amino acids in the GSSP4 polypeptides of the invention in order to extend half-life within the body. Thus, in some embodiments, one or more of the amino acids are preferably in the L configuration. In other embodiments, one or more of the amino acids are preferably in the D configuration.

Percent Identity

The polypeptides of the present invention also include polypeptides having an amino acid sequence at least 50% identical, at least 60% identical, or 70%, 80%, 85%, 90%, 91%, 92%, 93%, 94%, 95%, 96%, 97%, 98% or 99% identical to a GSSP4 polypeptide as described above. By a polypeptide having an amino acid sequence at least, for example, 95% "identical" to a GSSP4 polypeptide amino acid sequence is meant that the amino acid sequence is identical to the GSSP4 polypeptide sequence except that it may include up to five amino acid alterations per each 100 amino acids of the GSSP4 polypeptide amino acid sequence. The reference sequence is the GSSP4 polypeptide with a sequence corresponding to the sequences provided in SEQ ID NO:3. Thus, to obtain a polypeptide having an amino acid sequence at least 95% identical to a GSSP4 polypeptide amino acid sequence, up to 5% (5 of 100) of the amino acid residues in the sequence may be inserted, deleted, or substituted with another amino acid compared with the GSSP4 polypeptide sequence. These alterations may occur at the amino or carboxy termini or anywhere between those terminal positions, interspersed either individually among residues in the sequence or in one or more contiguous groups within the sequence.

As a practical matter, whether any particular polypeptide is a percentage identical to a GSSP4 polypeptide can be determined conventionally using known computer programs. Such algorithms and programs include, but are by no means limited to, TBLASTN, BLASTP, FASTA, TFASTA, and CLUSTALW (Pearson and Lipman, (1988) Proc Natl Acad Sci USA April;85(8):2444–8; Altschul et al., (1990) *J. Mol. Biol.* 215(3):403–410; Thompson et al., (1994) *Nucleic Acids Res.* 22(2):4673–4680; Higgins et al., (1996) Meth. Enzymol. 266:383–402; Altschul et al., (1997) *Nuc. Acids Res.* 25:3389–3402; Altschul et al., (1993) *Nature Genetics* 3:266–272). In a particularly preferred embodiment, protein and nucleic acid sequence homologies are evaluated using the Basic Local Alignment Search Tool ("BLAST"), which is well known in the art (See, e.g., Karlin and Altschul (1990) Proc Natl Acad Sci USA March;87(6):2264–8; Altschul et al., 1990, 1993, 1997, all supra). In particular, five specific BLAST programs are used to perform the following tasks:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (see, Gonnet et al., (1992) Science June 5;256(5062): 1443–5; Henikoff and Henikoff (1993) Proteins September;17(1):49–61). Less preferably, the PAM or PAM250 matrices may also be used (See, e.g., Schwartz and Dayhoff, eds, (1978) Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (See, e.g., Karlin and Altschul, (1990) Proc Natl Acad Sci USA March;87(6):2264–8). The BLAST programs may be used with the default parameters or with modified parameters provided by the user. Preferably, the parameters are default parameters.

A preferred method for determining the best overall match between a query sequence (a sequence of the present invention) and a subject sequence, also referred to as a global sequence alignment, can be determined using the FASTDB computer program based on the algorithm of Brutlag et al. (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N- or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence. For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues are perfectly matched the final percent identity would be 90%.

In another example, a 90-residue subject sequence is compared with a 100-residue query sequence. This time the deletions are internal so there are no residues at the N- or C-termini of the subject sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are made for the purposes of the present invention.

Production

Note, throughout the disclosure, wherever GSSP4 polypeptides are discussed, GSSP4 fragments are specifically intended to be included as a preferred subset of GSSP4 polypeptides. Specific production methods are addressed in detail in sections III, IV, V, and VI of the present specification.

In brief, GSSP4 polypeptides are preferably isolated from mammalian tissue samples, preferably human samples, or expressed from mammalian genes, preferably human genes, in mammalian cells, preferably human cells. The GSSP4 polypeptides of the invention can be made using expression methods known in the art. The polynucleotides encoding the desired polypeptides of the invention, including fragments thereof, are ligated into an expression vector suitable for the particular host used. Both eukaryotic and prokaryotic host systems can be used in forming recombinant polypeptides. The polypeptides are isolated from lysed cells or from the culture medium and purified to the extent needed for its intended use. In addition, shorter protein fragments may be produced by chemical synthesis. Purification is by techniques known in the art, for example, differential extraction, salt fractionation, chromatography, centrifugation, and the like. Nucleotides comprising the coding sequence of the polynucleotides of the invention, or fragments thereof, are cloned into expression vectors by anyone skilled in the art. Preferred expression vectors include eukaryotic and prokaryotic expression vectors. Further preferred is the pGEX-3X expression vector. Purification of GSSP4 polypeptides may be facilitated by recombinant fusion of a heterologous peptide to the C- or N-terminus of the GSSP4 polypeptides. Preferred fusion polypeptides expressed include heterologous polypeptides containing a His-tag added to the C-terminus, a glutathione-S-transferase (GST) tag and a factor Xa protease digestion site.

A preferred method of making the polypeptides of the invention includes a method comprising the following steps: *Escherichia coli* cells, preferably BL21, and preferably comprising the pGEX-3X vector containing polynucleotides of the invention containing a His tag added to the C-terminus, GST tag and Xa protease site, are grown to subconfluence, preferably absorbance of 0.8, and induced with isopropyl beta-D-thiogalactoside. Cells are pelleted, washed and lysed in buffer, preferably in buffer containing guanidine hydrochloride. Polypeptides are allowed to bind to nickel, preferably Ni—NTA containing beads, and are washed with buffers, preferably buffers containing urea. Polypeptide bound to nickel are equilibrated with buffer, preferably buffer containing sodium chloride and calcium chloride, preferably at pH 7.5. Polypeptides bound to Nickel are digested, ie. treated with buffer comprising protease, preferably protease factor Xa. Digestion is preferably carried out at room temperature for 12 to 20 hours. The cleaved GST tag, if any, is washed away with buffer, preferably buffer with urea, preferably at pH 5.9. Polypeptides of the invention are eluted with buffer, preferably buffer with urea, preferably at pH 4.5. Polypeptides of the invention are refolded, preferably by methods comprising the following steps: Polypeptides are diluted in buffer common in the art, preferably to a concentration of 100 microgram/ml, preferably in buffer containing urea at pH 4.5. Polypeptides are dialyzed against buffer, preferably dialysis buffer comprising 4M urea, 5 mM cysteine, 0.02% Tween-20, 10% glycerol, 10 mM Tris, 150 mM sodium chloride, and 100 mM NaH2PO4, preferably at pH 8.3. Dialysis buffer comprising 2 M urea is used to replace the initial dialysis buffer, and dialysis buffer is replaced at least 1, 2, or 3 times over at least 1, 2, 3, 4, 5, or 6 days. The refolded polypeptide is desalted by any method known in the art, preferably using a spin column. Polypeptides of the invention are further purified by methods known in the art. Preferably polpeptides are purified with reverse phase HPLC. Polypeptides are preferably eluted with 0.08% trifluoroacetic acid and a 10–50% acetonitrile gradient, and elution is monitored preferably at 206 nm. Acetonitrile and trifluoroacetic acid are removed for the compositions comprising the purified polypeptide, preferably by evaporation by lyophilization.

Further examples of methods useful for the expression or purification of polypeptides of the invention are found described in *Methods in Enzymology*.

The nucleic acid encoding a GSSP4 fragment can be obtained by PCR from a vector containing the GSSP4 nucleotide sequence using oligonucleotide primers complementary to the desired GSSP4 cDNA and containing restriction endonuclease sequences.

Transfection of a GSSP4 fragment-expressing vector into mouse NIH 3T3 cells is one embodiment of introducing polynucleotides into host cells. Introduction of a polynucleotide encoding a polypeptide into a host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al. ((1986) Methods in Molecular Biology, Elsevier Science Publishing Co., Inc., Amsterdam). It is specifically contemplated that the polypeptides of the present invention may in fact be expressed by a host cell lacking a recombinant vector.

A polypeptide of this invention (i.e. a GSSP4 fragment) can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, the polypeptides of the present invention may be glycosylated or may be non-glycosylated. Preferably the polypeptides of the invention are non-glycosylated. In addition, polypeptides of the invention may also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., (1989) Proc Natl Acad Sci USA November;86(22):8932–5; Koller et al., (1989) Proc Natl Acad Sci USA November;86(22):8927–31; and Zijlstra et al. (1989) Nature November 23;342(6248):435–8; the disclosures of each of which are incorporated by reference in their entireties).

Modifications

In addition, polypeptides of the invention can be chemically synthesized using techniques known in the art (See, e.g., Creighton, 1983 Proteins. New York, N.Y.: W.H. Freeman and Company; and Hunkapiller et al., (1984) Nature July 12–18;310(5973):105–11). For example, a relative short fragment of the invention can be synthesized by use of a peptide synthesizer. Furthermore, if desired, nonclassical amino acids or chemical amino acid analogs can be introduced as a substitution or addition into the fragment sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptide fragments which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptide fragments may also be modified with a detectable label, such as an enzymatic, fluorescent, isotopic or affinity label to allow for detection and isolation of the polypeptide.

Also provided by the invention are chemically modified derivatives of the polypeptides of the invention that may provide additional advantages such as increased solubility, stability and circulating time of the polypeptide, or decreased immunogenicity. See U.S. Pat. No. 4,179,337. The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the polypeptide with consideration of effects on functional or antigenic domains of the polypeptide. There are a number of attachment methods available to those skilled in the art, e.g., EP 0 401 384, herein incorporated by reference (coupling PEG to G-CSF), see also Malik et al. (1992) Exp Hematol. September;20(8):1028–35, reporting pegylation of GM-CSF using tresyl chloride). Preferred for therapeutic purposes is attachment at an amino group, such as attachment at the N-terminus or lysine group.

Multimers

The polypeptide fragments of the invention may be in monomers or multimers (i.e., dimers, trimers, tetramers and higher multimers). Accordingly, the present invention relates to monomers and multimers of the polypeptide fragments of the invention, their preparation, and compositions (preferably, pharmaceutical or physiologically acceptable compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the GSSP4 polypeptides of the invention (including polypeptide fragments, variants, splice variants, and fusion proteins corresponding to these polypeptide fragments as described herein). These homomers may contain polypeptide fragments having identical or different amino acid sequences. In a specific embodiment, a homomer of the invention is a multimer containing only polypeptide fragments having an identical amino acid sequence. In another specific embodiment, a homomer of the invention is a multimer containing polypeptide fragments having different amino acid sequences. In specific embodiments, the multimer of the invention is a homodimer (e.g., containing polypeptide fragments having identical or different amino acid sequences) or a homotrimer (e.g., containing polypeptide fragments having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., corresponding to different proteins or polypeptide fragments thereof) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences, which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. FEBS Letters (1994) May 16;344(2–3): 191–5. and in U.S. patent application Ser. No. 08/446,922, hereby incorporated by reference. Other peptides derived from naturally occurring trimeric proteins may be employed in preparing trimeric polypeptides of the invention. In another example, proteins of the invention are associated by interactions between Flag® & polypeptide sequence contained in fusion proteins of the invention containing Flag® polypeptide sequence. In a further embodiment, proteins of the invention are associated by interactions between heterologous polypeptide sequence contained in Flag® fusion proteins of the invention and anti Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, at least 30 techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (See, e.g., U.S. Pat. No. 5,478,925, which is herein incorporated by reference in its entirety).

II. GSSP4 Polynucleotides of the Invention

Preferred polynucleotides are those that encode GSSP4 polypeptides of the invention. The recombinant polynucleotides encoding GSSP4 polypeptides can be used in a variety of ways, including, but not limited to, expressing the polypeptides in recombinant cells for use in screening assays for antagonists and agonists of its activity as well as to facilitate its purification for use in a variety of ways including, but not limited to screening assays for agonists and antagonists of its activity, diagnostic screens, and raising antibodies, as well as treatment and/or prevention of metabolic-related diseases and disorders and/or to reduce body mass.

The invention relates to the polynucleotides encoding GSSP4 polypeptides and variant polypeptide fragments thereof as described herein. These polynucleotides may be purified, isolated, and/or recombinant. In all cases, the desired GSSP4 polynucleotides of the invention are those that encode GSSP4 polypeptides of the invention having metabolic-related activity as described and discussed herein.

Fragments

A polynucleotide fragment is a polynucleotide having a sequence that entirely is the same as part, but not all, of the full length GSSP4 polypeptide or a specified GSSP4 polypeptide nucleotide sequence. Such fragments may be "free-standing", i.e. not part of or fused to other polynucleotides, or they may be comprised within another non-GSSP4 (heterologous) polynucleotide of which they form a part or region. However, several GSSP4 polynucleotide fragments may be comprised within a single polynucleotide.

The GSSP4 polynucleotides of the invention comprise from 18 consecutive bases to 18 consecutive bases less than the full length polynucleotide sequences encoding the intact GSSP4 polypeptides, for example the GSSP4 polynucleotide sequences in SEQ ID NO:1 or 2. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, or 648 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer representing 18 nucleotides less than the 3' most nucleotide position of the intact GSSP4 polypeptides cDNA as set forth in SEQ ID NO: 2, or elsewhere herein.

Further included as preferred polynucleotides of the present invention are nucleic acid fragments at least 18 nucleotides in length, as described above, that are further specified in terms of their 5' and 3' position set forth in the sequence listing below. For allelic and degenerate and other variants, position 1 is defined as the 5' most nucleotide of the ORF, i.e., the nucleotide "A" of the start codon (ATG) with the remaining nucleotides numbered consecutively. Therefore, every combination of a 5' and 3' nucleotide position that a polynucleotide fragment invention, at least 18 contiguous nucleotides in length, could occupy on an intact GSSP4 polypeptide polynucleotide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the polynucleotide sequence of the present invention minus 18, and where "y" equals an integer between 19 and the number of nucleotides of the polynucleotide sequence of the present invention minus 18 nucleotides; and where "x" is an integer smaller then "y" by at least 18.

The GSSP4 polynucleotide fragments of the invention comprise from 18 consecutive bases to the full length polynucleotide sequence encoding the GSSP4 fragments described in Section II of the Preferred Embodiments of the Invention. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 740, 770, 800, 850, 900, 950, 1000, 1100, 1200, 1300, 1400, 1500, 1600, 1700, 1800, 1900, 2000, 2100 or 2200 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer corresponding to the 3' most nucleotide position of a GSSP4 fragment cDNA herein.

Further included as preferred polynucleotides of the present invention are nucleic acid fragments at least 18 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the open reading frame (ORF), i.e., the nucleotide "A" of the start codon (ATG) with the remaining nucleotides numbered consecutively. Therefore, every combination of a 5' and 3' nucleotide position that a polynucleotide fragment invention, at least 18 contiguous nucleotides in length, could occupy on a GSSP4 fragment polynucleotide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the GSSP4 polynucleotide sequences of the present invention minus 18, and where "y" equals an integer between 9 and the number of nucleotides of the GSSP4 polynucleotide sequences of the present invention; and where "x" is an integer smaller than "y" by at least 18. Every combination of "x" and 'y' positions are included as specific embodiments of the invention. Moreover, the formula "x" to "y" may be modified as "'x1–x2" to "y1–y2"', wherein "x1–x2" and "y1–y2" represent positional ranges selected from any two nucleotide positions of the sequence listing. Alternative formulas include "'x1–x2' to 'y'" and "'x' to 'y1–y2'".

These specific embodiments, and other polynucleotide fragment embodiments described herein may be modified as being "at least", "equal to", "equal to or less than", "less than", "at least _____ but not greater than _____" or "from _____ to _____". a specified size or specified 5' and/or 3' positions.

The present invention also provides for the exclusion of any species of polynucleotide fragments of the present invention specified by 5' and 3' positions or polynucleotides specified by size in nucleotides as described above. Any number of fragments specified by 5' and 3' positions or by size in nucleotides, as described above, may be excluded.

Variants

In other preferred embodiments, variants of GSSP4 polynucleotides encoding GSSP4 polypeptides are envisioned. Variants of polynucleotides, as the term is used herein, are polynucleotides whose sequence differs from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Polynucleotide variants that comprise a sequence substantially different from those described above but that, due to the degeneracy of the genetic code, still encode GSSP4 polypeptides of the present invention are also specifically envisioned. It would also be routine for one skilled in the art to generate the degenerate variants described above, for instance, to optimize codon expression for a particular host (e.g., change codons in the human mRNA to those preferred by other mammalian or bacterial host cells).

As stated above, variant polynucleotides may occur naturally, such as a natural allelic variant, or by recombinant methods. By an "allelic variant" is intended one of several alternate forms of a gene occupying a given locus on a chromosome of an organism (See, e.g., B. Lewin, (1990) Genes IV, Oxford University Press, New York). Non-naturally occurring variants may be produced using art-known mutagenesis techniques. Such nucleic acid variants include those produced by nucleotide substitutions, deletions, or additions. The substitutions, deletions, or additions may involve one or more nucleotides. Alterations in the coding regions may produce conservative or non-conservative amino acid substitutions, deletions or additions. Especially preferred among these are silent substitutions, additions and deletions, which do not alter the properties and activities of GSSP4 polypeptides of the invention. Also preferred in this regard are conservative substitutions.

Nucleotide changes present in a variant polynucleotide are preferably silent, which means that they do not alter the amino acids encoded by the polynucleotide. However, nucleotide changes may also result in amino acid substitutions, additions, deletions, fusions and truncations in the polypeptide encoded by the reference sequence.

In cases where the nucleotide substitutions result in one or more amino acid changes, preferred GSSP4 polypeptides include those that retain one or more metabolic-related activity as described in Section I of the Preferred Embodiments of the Invention.

By "retain the same activities" is meant that the activity measured using the polypeptide encoded by the variant GSSP4 polynucleotide in assays is at least 75%, 80%, 85%, 90%, 95%, 96%, 97%, 98%, 99%, or 100%, and not more than 101%, 102%, 103%, 104%, 105%, 110%, 115%, 120% or 125% of the activity measured using a GSSP4 polypeptide described in the Examples Section herein.

By the activity being "increased" is meant that the activity measured using the polypeptide encoded by the variant GSSP4 polynucleotide in assays is at least 125%, 130%, 135%, 140%, 145%, 150%, 155%, 160%, 170%, 180%, 190%, 200%, 225%, 250%, 275%, 300%, 325%, 350%, 375%, 400%, 450%, or 500% of the activity measured using a GSSP4 polypeptide described in the Examples Section herein.

By the activity being "decrease" is meant that the activity measured using the polypeptide encoded by the variant GSSP4 polynucleotide in assays is decreased by at least 25%, 30%, 35%, 40%, 45%, or 50% of the activity measured using a GSSP4 polypeptide described in the Examples Section herein Percent Identity The present invention is further directed to nucleic acid molecules having sequences at least 50%, 60%, 70%, 80%, 90%, 95%, 96%, 97%, 98% or 99% identical to the polynucleotide sequences of SEQ ID NO:1, or 2 or fragments thereof that encode a polypeptide having metabolic-related activity as described in Section I of the Preferred Embodiments of the Invention. Of course, due to the degeneracy of the genetic code, one of ordinary skill in the art will immediately recognize that a large number of the nucleic acid molecules at least 50%, 60%, 70%, 80%, 90%, 95%, 96%, 97%, 98%, or 99% identical to the nucleic acid sequences shown in SEQ ID NO:1, or 2 or fragments thereof will encode a polypeptide having biological activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly affect protein function (e.g., replacing one aliphatic amino acid with a second aliphatic amino acid), as further described previously in Section I of the Preferred Embodiments of the Invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the GSSP4 polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence or any fragment specified as described herein.

The methods of determining and defining whether any particular nucleic acid molecule or polypeptide is at least 50%, 60%, 70%, 80%, 90%, 95%, 96%, 97%, 98% or 99% identical to a nucleotide sequence of the present invention can be done by using known computer programs. A preferred method for determining the best overall match between a query sequence (a sequence of the present invention) and a subject sequence, also referred to as a global sequence alignment, can be determined using the FASTDB computer program based on the algorithm of Brutlag et al., ((1990) Comput Appl Biosci. July;6(3):237–45). In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score. No other manual corrections are made for the purposes of the present invention.

Fusions

Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including for example, but not limited to non-coding 5' and 3' sequences, vector sequence, sequences used for purification, probing, or priming. For example, heterologous sequences include transcribed, non-translated sequences that may play a role in transcription, and mRNA processing, for example, ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification of the fused polypeptide. In certain preferred embodiments of this aspect of the invention, the tag amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein (See, Gentz et al., (1989) Proc Natl Acad Sci USA February;86(3):821–4). The "HA" tag is another peptide useful for purification which corresponds to an epitope derived from the influenza hemagglutinin protein (See, Wilson et al., (1984) Cell 37(3): 767–78). As discussed above, other such fusion proteins include GSSP4 fragment cDNA fused to Fc at the N- or C-terminus.

III. Recombinant Vectors of the Invention

The term "vector" is used herein to designate either a circular or a linear DNA or RNA molecule, that is either double-stranded or single-stranded, and that comprises at least one polynucleotide of interest that is sought to be transferred in a cell host or in a unicellular or multicellular host organism.

The present invention relates to recombinant vectors comprising any one of the polynucleotides described herein.

The present invention encompasses a family of recombinant vectors that comprise polynucleotides encoding GSSP4 polypeptides of the invention.

In a first preferred embodiment, a recombinant vector of the invention is used to amplify the inserted polynucleotide in a suitable cell host, this polynucleotide being amplified every time that the recombinant vector replicates. The inserted polynucleotide can be one that encodes GSSP4 polypeptides of the invention.

A second preferred embodiment of the recombinant vectors according to the invention consists of expression vectors comprising polynucleotides encoding GSSP4 polypeptides of the invention. Within certain embodiments, expression vectors are employed to express a GSSP4 polypeptide of the invention, preferably a modified GSSP4 fragment described in the present invention, which can be then purified and, for example, be used as a treatment for metabolic-related diseases, or simply to reduce body mass of individuals.

Expression requires that appropriate signals are provided in the vectors, said signals including various regulatory elements, such as enhancers/promoters from both viral and mammalian sources, that drive expression of the genes of interest in host cells. Dominant drug selection markers for establishing permanent, stable, cell clones expressing the products are generally included in the expression vectors of the invention, as they are elements that link expression of the drug selection markers to expression of the polypeptide.

More particularly, the present invention relates to expression vectors which include nucleic acids encoding a GSSP4 polypeptide of the invention, or a modified GSSP4 fragment as described herein, or variants or fragments thereof, under the control of a regulatory sequence selected among GSSP4 polypeptides, or alternatively under the control of an exogenous regulatory sequence.

Consequently, preferred expression vectors of the invention are selected from the group consisting of: (a) a GSSP4 fragment regulatory sequence and driving the expression of a coding polynucleotide operably linked thereto; and (b) a GSSP4 fragment coding sequence of the invention, operably linked to regulatory sequences allowing its expression in a suitable cell host and/or host organism.

Some of the elements which can be found in the vectors of the present invention are described in further detail in the following sections.

1) General Features of the Expression Vectors of the Invention:

A recombinant vector according to the invention comprises, but is not limited to, a YAC (Yeast Artificial Chromosome), a BAC (Bacterial Artificial Chromosome), a phage, a phagemid, a cosmid, a plasmid, or even a linear DNA molecule which may consist of a chromosomal, non-chromosomal, semi-synthetic or synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription;

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation sites, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

2) Regulatory Elements

Promoters

The suitable promoter regions used in the expression vectors of the present invention are chosen taking into account the cell host in which the heterologous gene is expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., (1983) Mol Cell Biol December;3(12):2156–65; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. In addition, promoters specific for a particular cell type may be chosen, such as those facilitating expression in adipose tissue, muscle tissue, or liver. Selection of a convenient vector and promoter is well within the level of ordinary skill in the art.

The choice of a promoter is well within the ability of a person skilled in the field of genetic engineering. For example, one may refer to Sambrook et al. (1989) Molecular Cloning: A Laboratory Manual, Cold Spring Harbor Laboratory Press, NY, Vol. 1, 2, 3 (1989), or also to the procedures described by Fuller et al. (1996) Immunology in Current Protocols in Molecular Biology.

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

3) Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4) Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and pGEM1 (Promega Biotec, Madison, Wis., USA).

Large numbers of other suitable vectors are known to those of skill in the art, and are commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Baculovirus Vectors

A suitable vector for the expression of polypeptides of the invention is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*.

Other suitable vectors for the expression of GSSP4 polypeptides in a baculovirus expression system include those described by Chai et al. (1993; Biotechnol Appl Biochem. December; 18 (Pt 3):259–73; Vlasak et al. (1983;

Eur J Biochem September 1;135(1):123–6); and Lenhard et al. (1996; Gene March 9;169(2):187–90).

Viral Vectors

In one specific embodiment, the vector is derived from an adenovirus. Preferred adenovirus vectors according to the invention are those described by Feldman and Steg (1996; Semin Interv Cardiol September;1(3):203–8) or Ohno et al. (1994; Science August 5;265(5173):781–4). Another preferred recombinant adenovirus according to this specific embodiment of the present invention is the human adenovirus type 2 or 5 (Ad 2 or Ad 5) or an adenovirus of animal origin (French patent application No. FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vivo gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., ((1989) Proc Natl Acad Sci USA December;86(23): 9079–83), Julan et al., (1992) J. Gen. Virol. 3:3251–3255 and Neda et al., ((1991) J Biol Chem August 5;266(22): 14143–6).

Yet another viral vector system that is contemplated by the invention consists of the adeno-associated virus (AAV). The adeno-associated virus is a naturally occurring defective virus that requires another virus, such as an adenovirus or a herpes virus, as a helper virus for efficient replication and a productive life cycle (Muzyczka et al., (1992) Curr Top Microbiol Immunol;158:97–129). It is also one of the few viruses that may integrate its DNA into non-dividing cells, and exhibits a high frequency of stable integration (Flotte et al., (1992) Am J Respir Cell Mol Biol September;7(3): 349–56; Samulski et al., (1989) J Virol September;63(9): 3822–8; McLaughlin et al., (1989) Am. J. Hum. Genet. 59:561–569). One advantageous feature of AAV derives from its reduced efficacy for transducing primary cells relative to transformed cells.

5) Delivery of the Recombinant Vectors

In order to effect expression of the polynucleotides of the invention, these constructs must be delivered into a cell. This delivery may be accomplished in vitro, as in laboratory procedures for transforming cell lines, or in vivo or ex vivo, as in the treatment of certain disease states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., (1973) Virology August;54(2):536–9; Chen et al., (1987) Mol Cell Biol August;7(8):2745–52), DEAE-dextran (Gopal, (1985) Mol Cell Biol May;5(5):1188–90), electroporation (Tur-Kaspa et al., (1986) Mol Cell Biol February;6(2):716–8; Potter et al., (1984) Proc Natl Acad Sci USA November;81 (22):7161–5.), direct microinjection (Harland et al., (1985) J Cell Biol September;101(3):1094–9), DNA-loaded liposomes (Nicolau et al., (1982) Biochim Biophys Acta October 11;721(2):185–90; Fraley et al., (1979) Proc Natl Acad Sci USA July;76(7):3348–52), and receptor-mediated transfection (Wu and Wu, (1987) J Biol Chem April 5;262(10): 4429–32; Wu and Wu (1988) Biochemistry February 9;27 (3):887–92). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Universit éd'Ottawa) as well as in the articles of Tascon et al. (1996) Nature Medicine. 2(8):888–892 and of Huygen et al. ((1996) Nat Med August;2(8):893–8).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. ((1990) Curr Genet February;17(2):97–103).

In a further embodiment, the polynucleotide of the invention may be entrapped in a liposome (Ghosh and Bacchawat, (1991) Targeted Diagn Ther;4:87–103; Wong et al., (1980) Gene 10:87–94; Nicolau et al., (1987) Methods Enzymol.; 149:157–76). These liposomes may further be targeted to cells expressing LSR by incorporating leptin, triglycerides, ACRP30, or other known LSR ligands into the liposome membrane.

In a specific embodiment, the invention provides a composition for the in vivo production of an GSSP4 polypeptides described herein. It comprises a naked polynucleotide operatively coding for this polypeptide, in solution in a physiologically acceptable carrier, and suitable for introduction into a tissue to cause cells of the tissue to express the said polypeptide.

The amount of vector to be injected to the desired host organism varies according to the site of injection. As an indicative dose, it will be injected between 0.1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired GSSP4 polypeptides or the desired fragment thereof is reintroduced into the animal body in order to deliver the recombinant protein within the body either locally or systemically.

IV. Recombinant Cells of the Invention

Another object of the invention consists of host cells recombinant for, i.e., that have been transformed or transfected with one of the polynucleotides described herein, and more precisely a polynucleotide comprising a polynucleotide encoding a GSSP4 polypeptide of the invention such as any one of those described in "Polynucleotides of the Invention". These polynucleotides can be present in cells as a result of transient or stable transfection. The invention includes host cells that are transformed (prokaryotic cells) or that are transfected (eukaryotic cells) with a recombinant vector such as any one of those described in "Recombinant Vectors of the Invention".

Generally, a recombinant host cell of the invention comprises at least one of the polynucleotides or the recombinant vectors of the invention that are described herein.

Preferred host cells used as recipients for the recombinant vectors of the invention are the following:

a) Prokaryotic host cells: *Escherichia coli* strains (I.E. DH5-α strain), *Bacillus subtilis, Salmonella typhimurium*, and strains from species like *Pseudomonas, Streptomyces* and *Staphylococcus*, and b) Eukaryotic host cells: HeLa cells (ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711), C127 cells (ATCC N° CRL-1804), 3T3 (ATCC N° CRL-6361), CHO (ATCC N° CCL-61), human kidney 293 (ATCC N° 45504; N° CRL-1573), BHK (ECACC N° 84100501; N° 84111301), PLC cells, HepG2, and Hep3B.

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skilled artisan.

Further, according to the invention, these recombinant cells can be created in vitro or in vivo in an animal, preferably a mammal, most preferably selected from the group consisting of mice, rats, dogs, pigs, sheep, cattle, and primates, not to include humans. Recombinant cells created in vitro can also be later surgically implanted in an animal, for example. Methods to create recombinant cells in vivo in animals are well-known in the art.

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct that alters the expression of a targeted gene in a cell type in which the gene is not normally expressed. This occurs when a polynucleotide construct is inserted into the chromosomal DNA of the target cell, wherein the polynucleotide construct comprises: a) a targeting sequence; b) a regulatory sequence and/or a coding sequence; and c) an unpaired splice-donor site, if necessary. Further included are polynucleotide constructs, as described above, wherein the construct further comprises a polynucleotide which encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles described by Koller et al., (1994) Annu. Rev. Immunol. 10:705–730; the disclosures of each of which are incorporated by reference in their entireties).

The expression of GSSP4s in mammalian, and typically human, cells may be rendered defective, or alternatively it may be enhanced, with the insertion of a GSSP4 genomic or cDNA sequence with the replacement of the GSSP4 gene counterpart in the genome of an animal cell by a GSSP4 polynucleotide according to the invention. These genetic alterations may be generated by homologous recombination events using specific DNA constructs that have been previously described.

One kind of host cell that may be used are mammalian zygotes, such as murine zygotes. For example, murine zygotes may undergo microinjection with a purified DNA molecule of interest, for example a purified DNA molecule that has previously been adjusted to a concentration range from 1 ng/ml—for BAC inserts-3 ng/µl—for P1 bacteriophage inserts-in 10 mM Tris-HCl, pH 7.4, 250 µM EDTA containing 100 mM NaCl, 30 µM spermine, and 70 µM spermidine. When the DNA to be microinjected has a large size, polyamines and high salt concentrations can be used in order to avoid mechanical breakage of this DNA, as described by Schedl et al ((1993) Nature March 18;362 (6417):258–61).

Any one of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC No. CRL-1821), ES-D3 (ATCC No. CRL1934 and No. CRL-11632), YS001 (ATCC No. CRL-11776), 36.5 (ATCC No. CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993; Methods Enzymol;225:803–23) and are inhibited in growth by irradiation, such as described by Robertson ((1987) Embryo-derived stem cell lines. In: E. J. Robertson Ed. Teratocarcinomas and embrionic stem cells: a practical approach. IRL Press, Oxford), or by the presence of an inhibitory concentration of LIF, such as described by Pease and Williams (1990; Exp Cell Res. October;190(2):209–11).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period. Cells are typically harvested by centrifugation, disrupted by physical or chemical means, and the resulting crude extract retained for further purification. Microbial cells employed in the expression of proteins can be disrupted by any convenient method, including freeze-thaw cycling, sonication, mechanical disruption, or use of cell lysing agents. Such methods are well known by the skilled artisan.

V. Transgenic Animals

The present invention also provides methods and compositions for the generation of non-human animals and plants that express recombinant GSSP4 polypeptides, i.e. recombinant GSSP4 fragments or full-length GSSP4 polypeptides. The animals or plants can be transgenic, i.e. each of their cells contains a gene encoding a GSSP4 polypeptide, or, alternatively, a polynucleotide encoding a GSSP4 polypeptide can be introduced into somatic cells of the animal or plant, e.g. into mammary secretory epithelial cells of a mammal. In preferred embodiments, the non-human animal is a mammal such as a cow, sheep, goat, pig, or rabbit.

Methods of making transgenic animals such as mammals are well known to those of skill in the art, and any such method can be used in the present invention. Briefly, transgenic mammals can be produced, e.g., by transfecting a pluripotential stem cell such as an ES cell with a polynucleotide encoding a polypeptide of interest. Successfully transformed ES cells can then be introduced into an early stage embryo which is then implanted into the uterus of a mammal of the same species. In certain cases, the transformed ("transgenic") cells will comprise part of the germ line of the resulting animal, and adult animals comprising the transgenic cells in the germ line can then be mated to other animals, thereby eventually producing a population of transgenic animals that have the transgene in each of their cells, and which can stably transmit the transgene to each of their offspring. Other methods of introducing the polynucleotide can be used, for example introducing the polynucleotide encoding the polypeptide of interest into a fertilized egg or early stage embryo via microinjection. Alternatively, the transgene may be introduced into an animal by infection of zygotes with a retrovirus containing the transgene (Jaenisch, R. (1976) Proc. Natl. Acad. Sci. USA 73, 1260–1264). Methods of making transgenic mammals are described, e.g., in Wall et al. (1992) J Cell Biochem 1992 June;49(2): 113–20; Hogan, et al. (1986) in Manipulating the mouse embryo. A Laboratory Manual. Cold Spring Harbor Laboratory Press, Cold Spring Harbor, N.Y.; in WO 91/08216, or in U.S. Pat. No. 4,736,866.

In a preferred method, the polynucleotides are microinjected into the fertilized oocyte. Typically, fertilized oocytes are microinjected using standard techniques, and then cultured in vitrountil a "pre-implantation embryo" is obtained. Such pre-implantation embryos preferably contain approximately 16 to 150 cells. Methods for culturing fertilized oocytes to the pre-implantation stage are described, e.g., by Gordon et al. ((1984) Methods in Enzymology, 101, 414); Hogan et al. ((1986) in Manipulating the mouse embryo. A Laboratory Manual. Cold Spring Harbor Laboratory Press, Cold Spring Harbor, N.Y) (for the mouse embryo); Hammer et al. ((1985) Nature, 315, 680) (for rabbit and porcine embryos); Gandolfi et al. ((1987) J. Reprod. Fert. 81, 23–28); Rexroad et al. ((1988) J. Anim. Sci. 66, 947–953) (for ovine embryos); and Eyestone et al. ((1989) J. Reprod. Fert. 85, 715–720); Camous et al. ((1984) J. Reprod. Fert. 72, 779–785); and Heyman et al. ((1987) Theriogenology 27, 5968) (for bovine embryos); the disclosures of each of which are incorporated herein in their entireties. Pre-implantation embryos are then transferred to an appropriate female by standard methods to permit the birth of a transgenic or chimeric animal, depending upon the stage of development when the transgene is introduced.

As the frequency of transgene incorporation is often low, the detection of transgene integration in pre-implantation embryos is often desirable using any of the herein-described methods. Any of a number of methods can be used to detect the presence of a transgene in a pre-implantation embryo. For example, one or more cells may be removed from the pre-implantation embryo, and the presence or absence of the transgene in the removed cell or cells can be detected using any standard method e.g. PCR. Alternatively, the presence of a transgene can be detected in utero or post partum using standard methods.

In a particularly preferred embodiment of the present invention, transgenic mammals are generated that secrete recombinant GSSP4 polypeptides in their milk. As the mammary gland is a highly efficient protein-producing organ, such methods can be used to produce protein concentrations in the gram per liter range, and often significantly more. Preferably, expression in the mammary gland is accomplished by operably linking the polynucleotide encoding the GSSP4 polypeptide to a mammary gland specific promoter and, optionally, other regulatory elements. Suitable promoters and other elements include, but are not limited to, those derived from mammalian short and long WAP, alpha, beta, and kappa, casein, alpha and beta lactoglobulin, beta-CN 5' genes, as well as the the mouse mammary tumor virus (MMTV) promoter. Such promoters and other elements may be derived from any mammal, including, but not limited to, cows, goats, sheep, pigs, mice, rabbits, and guinea pigs. Promoter and other regulatory sequences, vectors, and other relevant teachings are provided, e.g., by Clark (1998) J Mammary Gland Biol Neoplasia 3:337–50; Jost et al. (1999) Nat. Biotechnol 17:160–4; U.S. Pat. Nos. 5,994,616; 6,140,552; 6,013,857; Sohn et al. (1999) DNA Cell Biol. 18:845–52; Kim et al. (1999) J. Biochem. (Japan) 126:320–5; Soulier et al. (1999) Euro. J. Biochem. 260:533–9; Zhang et al. (1997) Chin. J. Biotech. 13:271–6; Rijnkels et al. (1998) Transgen. Res. 7:5–14; Korhonen et al. (1997) Euro. J. Biochem. 245: 482–9; Uusi-Oukari et al. (1997) Transgen. Res. 6:75–84; Hitchin et al. (1996) Prot. Expr. Purif. 7:247–52; Platenburg et al. (1994) Transgen. Res. 3:99–108; Heng-Cherl et al. (1993) Animal Biotech 4:89–107; and Christa et al. (2000) Euro. J. Biochem. 267:1665–71; the entire disclosures of each of which is herein incorporated by reference.

In another embodiment, the polypeptides of the invention can be produced in milk by introducing polynucleotides encoding the polypeptides into somatic cells of the mammary gland in vivo, e.g. mammary secreting epithelial cells. For example, plasmid DNA can be infused through the nipple canal, e.g. in association with DEAE-dextran (see, e.g., Hens et al. (2000) Biochim. Biophys. Acta 1523: 161–171), in association with a ligand that can lead to receptor-mediated endocytosis of the construct (see, e.g., Sobolev et al. (1998) 273:7928–33), or in a viral vector such as a retroviral vector, e.g. the Gibbon ape leukemia virus (see, e.g., Archer et al. (1994) PNAS 91:6840–6844). In any of these embodiments, the polynucleotide may be operably linked to a mammary gland specific promoter, as described above, or, alternatively, any strongly expressing promoter such as CMV or MoMLV LTR.

The suitability of any vector, promoter, regulatory element, etc. for use in the present invention can be assessed beforehand by transfecting cells such as mammary epithelial cells, e.g. MacT cells (bovine mammary epithelial cells) or GME cells (goat mammary epithelial cells), in vitro and assessing the efficiency of transfection and expression of the transgene in the cells.

For in vivo administration, the polynucleotides can be administered in any suitable formulation, at any of a range of concentrations (e.g. 1–500 µg/ml, preferably 50–100 µg/ml), at any volume (e.g. 1–100 ml, preferably 1 to 20 ml), and can be administered any number of times (e.g. 1, 2, 3, 5, or 10 times), at any frequency (e.g. every 1, 2, 3, 5, 10, or any number of days). Suitable concentrations, frequencies, modes of administration, etc. will depend upon the particular polynucleotide, vector, animal, etc., and can readily be determined by one of skill in the art.

In a preferred embodiment, a retroviral vector such as as Gibbon ape leukemia viral vector is used, as described in Archer et al. ((1994) PNAS 91:6840–6844). As retroviral infection typically requires cell division, cell division in the mammary glands can be stimulated in conjunction with the administration of the vector, e.g. using a factor such as estrodiol benzoate, progesterone, reserpine, or dexamethasone. Further, retroviral and other methods of infection can be facilitated using accessory compounds such as polybrene.

In any of the herein-described methods for obtaining GSSP4 polypeptides from milk, the quantity of milk obtained, and thus the quantity of GSSP4 polypeptides produced, can be enhanced using any standard method of lactation induction, e.g. using hexestrol, estrogen, and/or progesterone.

The polynucleotides used in such embodiments can either encode a full-length GSSP4 polypeptide or a GSSP4 fragment. Typically, the encoded polypeptide will include a signal sequence to ensure the secretion of the protein into the milk. Where a full length GSSP4 sequence is used, the full length protein can, e.g., be isolated from milk and cleaved in vitro using a suitable protease. Alternatively, a second, protease-encoding polynucleotide can be introduced into the animal or into the mammary gland cells, whereby expression of the protease results in the cleavage of the GSSP4 polypeptide in vivo, thereby allowing the direct isolation of GSSP4 fragments from milk.

VI. Pharmaceutical or Physiologically Acceptable Compositions of the Invention

The GSSP4 polypeptides of the invention can be administered to non-human animals and/or humans, alone or in pharmaceutical or physiologically acceptable compositions where they are mixed with suitable carriers or excipient(s). The pharmaceutical or physiologically acceptable composition is then provided at a therapeutically effective dose. A therapeutically effective dose refers to that amount of a GSSP4 polypeptide sufficient to result in prevention or amelioration of symptoms or physiological status of metabolic-related diseases or disorders as determined by the methods described herein. A therapeutically effective dose can also refer to the amount of a GSSP4 polypeptide necessary for a reduction in weight or a prevention of an increase in weight or prevention of an increase in the rate of weight gain in persons desiring this affect for cosmetic reasons. A therapeutically effective dosage of a GSSP4 polypeptide of the invention is that dosage that is adequate to promote weight loss or weight gain with continued periodic use or administration. Techniques for formulation and administration of GSSP4 polypeptides may be found in "Remington's Pharmaceutical Sciences," Mack Publishing Co., Easton, Pa., latest edition.

Other diseases or disorders that GSSP4 polypeptides of the invention could be used to treat or prevent include, but are not limited to, obesity and metabolic-related diseases and disorders such as obesity, impaired glucose tolerance (IGT), insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other metabolic-related disorders to be treated by compounds of the invention include hyperlipidemia and hyperuricemia. The GSSP4 polypeptides may also be used to enhance physical performance during work or exercise or enhance a feeling of general well-being. Physical performance activities include walking, running, jumping, lifting and/or climbing.

The GSSP4 polypeptides or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

It is expressly considered that the GSSP4 polypeptides of the invention may be provided alone or in combination with other pharmaceutically or physiologically acceptable compounds. Other compounds useful for the treatment of obesity and other diseases and disorders are currently well-known in the art.

In a preferred embodiment, the GSSP4 polypeptides are useful for, and used in, the treatment of insulin resistance and diabetes using methods described herein and known in the art. More particularly, a preferred embodiments relates to process for the therapeutic modification and regulation of glucose metabolism in an animal or human subject, which comprises administering to a subject in need of treatment (alternatively on a timed daily basis) GSSP4 polypeptide (or polynucleotide encoding said polypeptide) in dosage amount and for a period sufficient to reduce plasma glucose levels in said animal or human subject.

Further preferred embodiments relate to methods for the prophylaxis or treatment of diabetes comprising administering to a subject in need of treatment (alternatively on a timed daily basis) a GSSP4 polypeptide (or polynucleotide encoding said polypeptide) in dosage amount and for a period sufficient to reduce plasma glucose levels in said animal or human subject.

Routes of Administration.

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. A particularly useful method of administering compounds for promoting weight loss involves surgical implantation, for example into the abdominal cavity of the recipient, of a device for delivering GSSP4 polypeptidesover an extended period of time. Other particularly preferred routes of administration are aerosol and depot formulation. Sustained release formulations, particularly depot of the invented medicaments are expressly contemplated.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable acceptable carrier and at least one polypeptide that is a GSSP4 polypeptide of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g. carbon dioxide. In the case of a pressurized aerosol the dosage unit may be determined by providing a valve to deliver a metered amount. Capsules and cartridges of, e.g. gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical or physiologically acceptable compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage.

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to increase leptin or lipoprotein uptake or binding in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD5O and ED5O. Compounds that exhibit high therapeutic indices are preferred.

The data obtained from these cell culture assays and animal studies can be used in formulating a range of dosage for use in humans. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to maintain or prevent weight loss or gain, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10–90% of the time, preferably between 30–90%; and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

A preferred dosage range for the amount of a GSSP4 polypeptide of the invention, which can be administered on a daily or regular basis to achieve desired results, including a reduction in levels of circulating plasma triglyceride-rich lipoproteins, range from 0.01–0.5 mg/kg body mass. A more preferred dosage range is from 0.05–0.1 mg/kg. Of course, these daily dosages can be delivered or administered in small amounts periodically during the course of a day. It is noted that these dosage ranges are only preferred ranges and are not meant to be limiting to the invention.

VII. Methods of Treatment

The invention is drawn inter alia to methods of preventing or treating metabolic-related diseases and disorders comprising providing an individual in need of such treatment with a GSSP4 polypeptide of the invention. Preferably, the GSSP4 polypeptide has metabolic-related activity either in vitro or in vivo. Preferably the GSSP4 polypeptide is provided to the individual in a pharmaceutical composition that is preferably taken orally. Preferably the individual is a mammal, and most preferably a human. In preferred embodiments, the metabolic-related disease or disorder is selected from the group consisting of obesity, impaired glucose tolerance (IGT), insulin resistance, atherosclerosis, atheromatous disease, heart disease, hypertension, stroke, Syndrome X, Noninsulin dependent diabetes mellitus (NIDDM, Type II diabetes), Insulin dependent diabetes mellitus (IDDM, Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure. In highly preferred embodiments, GSSP4 polypeptides in pharmaceutical compositions are used to modulate body weight in healthy individuals for cosmetic reasons.

The invention also features a method of preventing or treating metabolic-related diseases and disorders comprising providing an individual in need of such treatment with a compound identified by assays of the invention (described in Section VI of the Preferred Embodiments of the Invention and in the Examples). Preferably these compounds antagonize or agonize effects of GSSP4 polypeptides in cells in vitro, muscles ex vivo, or in animal models. Alternatively, these compounds agonize or antagonize the effects of GSSP4 polypeptides on glucose metabolism, fatty acid metabolism, or lipid metabolism. Preferably, the compound is provided to the individual in a pharmaceutical composition that is preferably taken orally. Preferably the individual is a mammal, and most preferably a human. In preferred embodiments, the metabolic-related disease or disorder is selected from the group consisting of obesity, impaired glucose tolerance (IGT), insulin resistance, atherosclerosis, atheromatous disease, heart disease, hypertension, stroke, Syndrome X, Noninsulin dependent diabetes mellitus (NIDDM, Type II diabetes), Insulin dependent diabetes mellitus (IDDM, Type I diabetes), diabetes-related complications (such as elevated ketone bodies), microangiopathy, retinopathy, ocular lesions, neuropathy, nephropathy, polycystic ovarian syndrome (PCOS), and microangiopathic lesions, as well as syndromes such as acanthosis nigricans, leprechaunism, and lipoatrophy to be treated by the methods of the invention. Heart disease includes, but is not limited to, cardiac insufficiency, coronary insufficiency, and high blood pressure. In highly preferred embodiments, the pharmaceutical compositions are used to modulate glucose levels. In highly preferred embodiments, the pharmaceutical compositions are used to modulate body weight for cosmetic reasons.

In a further preferred embodiment, NIDDM patients are often treated with oral insulin secretagogues, such as 1,1-dimethyl-2-(2-morpholinophenyl)guanidine fumarate (BTS67582) or sulfonylureas including tolbutamide, tolazamide, chlorpropamide, glibendamide, glimepiride, glipizide and glidazide, or with insulin sensitising agents including metformin, ciglitazone, trogitazone and pioglitazone. A further use of the present invention is in therapy of NIDDM patients to improve their weight and glucose control, comprising a pharmaceutical or physiologically acceptable composition described in the fifth aspect or polynucleotides described in the second aspect in combination with an oral insulin secretagogue or an insulin sensitising agent. Preferably, the oral insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the weight and glucose control of NIDDM patients comprising the administration of said pharmaceutical or physiologically acceptable composition described in the fifth aspect or polynucleotides described in the second aspect alone, without an oral insulin secretagogue or an insulin sensitising agent.

In a further preferred embodiment, the present invention may be administered either concomitantly or concurrently, with the oral insulin secretagogue or insulin sensitising agent for example in the form of separate dosage units to be used simultaneously, separately or sequentially (either before or after the secretagogue or either before or after the sensitising agent). Accordingly, the present invention further provides a product containing a composition of said a pharmaceutical or physiologically acceptable composition described in the fifth aspect or polynucleotides described in the second aspect and an oral insulin secretagogue or insulin sensitising agent as a combined preparation for simultaneous, separate or sequential use for the improvement of weight and glucose control in NIDDM patients. The ratio of the present composition to the oral insulin secretagogue or insulin sensitising agent is such that the quantity of each active ingredient employed will be such as to provide a therapeutically effective level, but will not be larger than the quantity recommended as safe for administration.

The action of reducing insulin resistance by the present invention indicates that compounds of such invention may be useful in the manufacture of a medicament which can be used as an insulin sensitiser. Accordingly, the present invention further provides for the use in the manufacture of a medicament which is an insulin sensitiser.

In further embodiments, some patients who are diagnosed with Insulin Dependent Diabetes Mellitus (IDDM, Type I) can also show a certain amount of insulin resistance. Therefore, there may be benefits in treating these patients with said pharmaceutical or physiologically acceptable composition described in the fifth aspect or polynucleotides described in the second aspect in order to reduce their insulin resistance. This would mean that these patients would require a lower dosage of insulin in order to maintain similar or better control of their diabetes since the insulin dose would be associated with a greater blood glucose lowering efficacy. Such therapy would provide long-term benefits in terms of reducing the detrimental effects which can be caused by prolonged high-dosage of insulin treatment. Additionally, some Noninsulin Dependent Diabetes Mellitus (NIDDM, Type II) patients are also treated with insulin and have insulin resistance. Accordingly the present invention further provides a method for, and the use thereof in the manufacture of the medicament for, reducing the amount of insulin required daily by a human having NIDDM. The present invention also provides a method for, and the use of the composition in the manufacture of a medicament for, the prophylaxis of long-term detrimental effects caused by prolonged high dosage of insulin in humans having IDDM.

A consequence of the resistance is that glucose concentrations rise. This leads, in turn, to an increased release of insulin. Hyperinsulinemia, both in the fasting and postprandial states, is a hallmark of insulin resistance. Hyperinsulinemia is also caused by stimulation of gluconeogenesis. Epidemilogical studies have shown that hyperinsulinemia is a risk factor for morbidity and mortality in cardiovascular disease (Smith U. (1994) *Am. J. Clin. Nutr.* 59, suppl. 686S). Accordingly, the invention also provides therapeutics and methods for reducing or preventing hypersecretion of insulin and disorders or conditions resulting therefrom.

NIDDM is associated with various complications. As defined herein, "complications of NIDDM" is referred to as cardiovascular complications or several of the metabolic and circulatory disturbances that are associated with hyperglycemia, e.g., insulin resistance, hyperinsulinemia and/or hyperproinsulinemia, delayed insulin release, dyslipidemia, retinopathy, peripheral neuropathy, hypertension, and other coronary artery diseases (CADs). CAD is a major cause of morbidity and mortality in patients with NIDDM. Thus, by providing therapeutics and methods for reducing glucose levels, the invention provides therapeutics and methods for treating and preventing NIDDM and consequences thereof.

The invention also provides therapeutics and methods for treating and preventing having impaired glucose tolerance (IGT). The usual meaning of impaired glucose tolerance is that it is a condition associated with insulin-resistance which is intermediate between frank, NIDDM and normal glucose tolerance (NGT). A high percentage of the IGT population is known to progress to NIDDM relative to persons with normal glucose tolerance (Sad, et al., *New Engl. J. Med.* 1988; 319:1500–6). Thus, by providing therapeutics and methods for reducing or preventing IGT, i.e., for normalizing insulin resistance, the progression to NIDDM can be delayed or prevented.

IGT is diagnosed by a procedure wherein an affected person's postprandial glucose response is determined to be abnormal as assessed by 2-hour postprandial plasma glucose levels. In this test, a measured amount of glucose is given to the patient and blood glucose levels measured regular intervals, usually every half hour for the first two hours and every hour thereafter. In a "normal" or non-IGT individual glucose levels rise during the first two hours to level less than 140 mg/dl and then drop rapidly. In an IGT individual, the blood glucose levels are higher and the drop-off level is at a slower rate.

Resistance to insulin-stimulated glucose uptake in individuals who do not become frankly hyperglycemic nevertheless increases the likelihood of these individuals to develop numerous other diseases. In particular, an attempt to compensate for insulin resistance sets in motion a series of events that play an important role in the development of both hypertension and coronary artery disease (CAD), such as premature atherosclerotic vascular disease. This cluster of abnormalities is commonly called the "Metabolic Syndrome", or the "Insulin-Resistance Syndrome" or "Syndrome X". Increased plasma triglyceride and decreased HDL-cholesterol concentrations, conditions which are known to be associated with CAD, have also been reported to be associated with insulin resistance. Thus, by providing therapeutics and methods for reducing or preventing insulin resistance, the invention provides methods for reducing and/or preventing the appearance of insulin-resistance syndrome.

Yet other diseases are associated with insulin resistance and, thus, be treated or prevented according to the methods of the invention. For example, obesity, which is the result of an imbalance between caloric intake and energy expenditure is highly correlated with insulin resistance and diabetes (Hotamisligil, Spiegelman et al., Science, 1993, 259:87–91). In humans obesity can be defined as a body weight exceeding 20% of the desirable body weight for individuals of the same sex, height and frame (Slans, L. B., in *Endocrinology & Metabolism*, 2d Ed., McGraw-Hill, New York 1987, pp. 1203–1244; see also, R. H. Williams, *Textbook of Endocrinology*, 1974, pp. 904–916). In other animals (or also in humans) obesity can be determined by body weight patterns correlated with prolactin profiles given that members of a species that are young, lean and "healthy" (i.e., free of any disorders, not just metabolic disorders) have daily plasma prolactin level profiles that follow a regular pattern that is highly reproducible with a small standard deviation. Obesity, or excess fat deposits, correlate with and may trigger the onset of various lipid metabolism disorders, e.g. hypertension, Type II diabetes (NIDDM), atherosclerosis, cardiovascular disease, etc. Even in the absence of clinical obesity (according to the above definition) the reduction of body fat stores (notably visceral fat stores) in man especially on a long-term or permanent basis would be of significant benefit, both cosmetically and physiologically. Thus, by preventing or treating obesity, the methods of the invention will allow an individual to have a more comfortable life and avoid the onset of various diseases triggered by obesity.

In yet another embodiment, the invention provides a method for treating a subject having polycystic ovary syndrome (PCOS). PCOS is among the most common disorders of premenopausal women, affecting 5–10% of this population. It is a syndrome of unknown Etiology characterized by hyperandrogenism, chronic anovulation, defects in insulin action, insulin secretion, ovarian steroidogenesis and fibrinolysis. Women with PCOS frequently are insulin resistant and at increased risk to develop glucose intolerance or NIDDM in the third and fourth decades of life (Dunaif et al. (1996) *J. Clin. Endocrinol. Metab.* 81:3299). Hyperandrogenism also is a feature of a variety of diverse insulin-resistant states, from the type A syndrome, through leprechaunism and lipoatrophic diabetes, to the type B syndrome, when these conditions occur in premenopausal women. It has been suggested that hyperinsulinemia per se causes hyperandrogenism. Insulin-sensitizing agents, e.g., troglitazone, have been shown to be effective in PCOS and that, in particular, the defects in insulin action, insulin secretion, ovarian steroidogenosis and fibrinolysis are improved (Ehrman et al. (1997) *J. Clin. Invest.* 100:1230), such as in insulin-resistant humans. Accordingly, the invention provides methods for reducing insulin resistance, normalizing blood glucose thus treating and/or preventing PCOS.

Insulin resistance is also often associated with infections and cancer. Thus, prevention or reducing insulin resistance according to the methods of the invention may prevent or reduce infections and cancer.

Insulin resistance can be diagnosed by various methods, such as by the intravenous glucose tolerance test or by measuring the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. Another way to do this is to follow the approach as disclosed in The New England Journal of Medicine, No. 3, pp. 1188 (1995), i.e. to select obese subjects as an initial criteria for entry into the treatment group. Some obese subjects have impaired glucose tolerance (IGT) while others have normal glucose tolerance (NGT). Since essentially all obese subjects are insulin resistant, i.e. even the NGT obese subjects are insulin resistant, they have fasting hyperinsulinemia. Therefore, the target of the treatment according to the present invention can be defined as NGT individuals who are obese or who have fasting hyperinsulinemia, or who have both.

Insulin resistance can also be diagnosed by the euglycemic glucose clamp test. This test involves the simultaneous administration of a constant insulin infusion and a variable rate glucose infusion. During the test, which lasts 3–4 hours, the plasma glucose concentration is kept constant at euglycemic levels by measuring the glucose level every 5–10 minutes and then adjusting the variable rate glucose infusion to keep the plasma glucose level unchanged. Under these circumstances, the rate of glucose entry into the bloodstream is equal to the overall rate of glucose disposal in the body. The difference between the rate of glucose disposal in the basal state (no insulin infusion) and the insulin infused state, represents insulin mediated glucose uptake. In normal individuals, insulin causes brisk and large increase in overall body glucose disposal, whereas in NIDDM subjects, this effect of insulin is greatly blunted, and is only 20–30% of normal. In insulin resistant subjects with either IGT or NGT, the rate of insulin stimulated glucose disposal is about half way between normal and NIDDM. For example, at a steady state plasma insulin concentration of about 100 uU/ml (a physiologic level) the glucose disposal rate in normal subjects is about 7 mg/kg/min. In NIDDM subjects, it is about 2.5 mg/.kg/min., and in patients with IGT (or insulin resistant subjects with NGT) it is about 4–5 mg/kg/min. This is a highly reproducible and precise test, and can distinguish patients within these categories. It is also known, that as subjects become more insulin resistant, the fasting insulin level rises. There is an excellent positive correlation between the height of the fasting insulin level and the magnitude of the insulin resistance as measured by euglycemic glucose clamp tests and, therefore, this provides the rationale for using fasting insulin levels as a surrogate measure of insulin resistance.

Thus, any of the above-described tests or other tests known in the art can be used to determine that a subject is insulin-resistant, which patient can then be treated according to the methods of the invention to reduce or cure the insulin-resistance. Alternatively, the methods of the invention can also be used to prevent the development of insulin resistance in a subject, e.g., those known to have an increased risk of developing insulin-resistance.

More generally, the instant invention is drawn to treatment with GSSP4 polypeptides where an individual is shown to have a particular genotype for GSSP4 marker. Treatment comprises providing pharmaceutically acceptable GSSP4 polypeptides to the individual. The exact amount of GSSP4 polypeptide provided would be determined through clinical trials under the guidance of qualified physicians, but would be expected to be in the range of 5–7 mg per individual per day. In general, a preferred range would be from 0.5 to 14 mg per individual per day, with a highly preferred range being between 1 and 10 mg per individual per day. Individuals who could benefit from treatment with GSSP4 polypeptides could be identified through genotyping.

GSSP4 Genotyping

The methods treatment using genotyping to identify individuals that would benefit from treatments of the invention are based on the finding that single nucleotide polymorphisms (SNPs) in GSSP4 have been identified that show an association in obese adolescents with free fatty acid (FFA) and respiratory quotient levels, others that show an association with the relationship between BMI and leptin, and still others that show an association with glucose levels. Further, a combination of GSSP4 SNPs associated with FFA and leptin metabolism may also predict people who will be seriously overweight.

Briefly, the term "genotype" as used herein refers to the identity of the alleles present in an individual or a sample. The term "genotyping" a sample or an individual for a biallelic marker consists of determining the specific allele or the specific nucleotide carried by an individual at a biallelic marker. Biallelic markers generally consist of a polymorphism at one single base position. Each biallelic marker therefore corresponds to two forms of a polynucleotide sequence which, when compared with one another, present a nucleotide modification at one position. Usually, the nucleotide modification involves the substitution of one nucleotide for another, optionally either the original or the alternative allele of the biallelic markers disclosed in SEQ ID NO:1. Optionally either the original or the alternative allele of these biallelic markers may be specified as being present. Preferred polynucleotides may consist of, consist essentially of, or comprise a contiguous span of nucleotides upstream and down-stream of the alternate allele position noted in SEQ ID No:1 as well as sequences which are complementary thereto. The "contiguous span" may be at least 8, 10, 12, 15, 18, 20, 25, 35, 40, 50, 70, 80, 100, 250, 500 or 1000 nucleotides in length, to the extent that a contiguous span of these lengths is consistent with the lengths of the particular Sequence ID.

Methods of genotyping comprise determining the identity of a nucleotide at GSSP4 biallelic marker site by any method known in the art. Preferably, microsequencing is used. The genotype is used to determine whether an individual should be treated with GSSP4 polypeptides. Thus, these genotyping methods are performed on nucleic acid samples derived from a single individual. These methods are well-known in the art, and discussed fully in the applications referenced briefly below.

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods that do not require amplification are also encompassed by the present genotyping methods.

Methods well-known to those skilled in the art that can be used to detect biallelic polymorphisms include methods such as conventional dot blot analysis, single strand conformational polymorphism analysis (SSCP; Orita et al. (1989) Proc Natl Acad Sci USA April;86(8):2766–70), denaturing gradient gel electrophoresis (DGGE), heteroduplex analysis, mismatch cleavage detection, and other conventional techniques as described in Sheffield et al. (1991; Am J Hum Genet October;49(4):699–706); White et al. (1992), Grompe et al. ((1989) Proc Natl Acad Sci USA August;86(15): 5888–92; (1993) Nat Genet. October;5(2):111–7). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, allele-specific amplification assay, or hybridization assay. The following is a description of some preferred methods. A highly preferred method is the microsequencing technique. The term "sequencing" is used herein to refer to polymerase extension of duplex primer/template complexes and includes both traditional sequencing and microsequencing. Preferred biallelic markers, as shown in SEQ ID NO:1 and corresponding 47 mers as shown in SEQ ID NOs:4–18, include but are not limited to:

1. Biallelic marker 1: position base 148, alternate alleles A/G
2. Biallelic marker 2: position base 2551, alternate alleles G/A
3. Biallelic marker 3: position base 4417, alternate alleles A/C
4. Biallelic marker 4: position base 6322, alternate alleles A/G (amino acid change isoleucine to valine)
5. Biallelic marker 7: position base 816, alternate alleles G/A
6. Biallelic marker 8: position base 924, alternate alleles G/A
7. Biallelic marker 9: position base 1206, alternate alleles C/A
8. Biallelic marker 10: position base 1851, alternate alleles T/C
9. Biallelic marker 11: position base 3124, alternate alleles C/T
10. Biallelic marker 12: position base 3563, alternate alleles G/A
11. Biallelic marker 13: position base 3792, alternate alleles G/A
12. Biallelic marker 14: position base 5757, alternate alleles T/C 1) Sequencing Assays The nucleotide present at a polymorphic site can be determined by sequencing methods. In a preferred embodiment, DNA samples are subjected to PCR amplification before sequencing using any method known in the art. Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers that hybridize just upstream of the polymorphic base of interest in the target nucleic acid. A polymerase is used to specifically extend the 3' end of the primer with one single ddNTP (chain terminator) complementary to the nucleotide at the polymorphic site. The identity of the incorporated nucleotide is then determined in any suitable way. Preferred microsequencing primers are described in SEQ ID NO:1.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883. Alternatively capillary electrophoresis can be used in order to process a higher number of assays simultaneously.

Different approaches can be used for the labeling and detection of ddNTPs. A homogeneous phase detection method based on fluorescence resonance energy transfer has been described by Chen and Kwok ((1997) Nucleic Acids Res. January 15;25(2):347–53) and Chen et al. ((1997) Proc Natl Acad Sci USA September 30;94(20):10756–61). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, (1997) Nucleic Acids Res. September 15;25(18):3749–50; (1997) Genome Res. April; 7(4):378–88).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template.

For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvänen, (1994) Clin Chim Acta. May;226(2):225–36) or linked to fluorescein (Livak and Hainer, (1994) Hum Mutat.;3(4):379–85). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate).

Other possible reporter-detection pairs include: ddNTP linked to dinitrophenyl (DNP) and anti-DNP alkaline phosphatase conjugate (Harju et al., (1993) Clin Chem. November;39(11 Pt 1):2282–7) or biotinylated ddNTP and horseradish peroxidase-conjugated streptavidin with o-phenylenediamine as a substrate (WO 92/15712). As yet another alternative solid-phase microsequencing procedure, Nyren et al. ((1993) Anal Biochem. January;208(1):171–5). described a method relying on the detection of DNA polymerase activity by an enzymatic luminometric inorganic pyrophosphate detection assay (ELIDA).

Pastinen et al. ((1997) Genome Res. June;7(6):606–14) describe a method for multiplex detection of single nucleotide polymorphism in which the solid phase minisequencing principle is applied to an oligonucleotide array format. High-density arrays of DNA probes attached to a solid support (DNA chips) are further described below.

It will be appreciated that any primer having a 3' end immediately adjacent to the polymorphic nucleotide may be used. Similarly, it will be appreciated that microsequencing analysis may be performed for any biallelic marker or any combination of biallelic markers of the present invention.

3) Allele-Specific Amplification Assay Methods

Discrimination between the two alleles of a biallelic marker can also be achieved by allele specific amplification, a selective strategy, whereby one of the alleles is amplified without, or at a much higher rate than, amplification of the other allele. This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well with the ordinary skill in the art.

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. ((1990) Proc Natl Acad Sci USA November;

87(22):8923–7). In this method, PCR is used to achieve the exponential amplification of target DNA, which is then detected using OLA.

Other amplification methods which are particularly suited for the detection of single nucleotide polymorphism include LCR (ligase chain reaction) and Gap LCR (GLCR). LCR uses two pairs of probes to exponentially amplify a specific target. The sequences of each pair of oligonucleotides are selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site.

In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide.

In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include probes specific for GSSP4 cDNA surrounding GSSP4 biallelic markers. Any hybridization assay may be used including Southern hybridization, Northern hybridization, dot blot hybridization and solid-phase hybridization (see Sambrook et al., supra).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele.

Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., supra). Stringent conditions are sequence dependent and will be different in different circumstances. Generally, stringent conditions are selected to be about 5° C. lower than the thermal melting point (Tm) for the specific sequence at a defined ionic strength and pH. Although such hybridizations can be performed in solution, it is preferred to employ a solid-phase hybridization assay. The target DNA comprising a biallelic marker of the present invention may be amplified prior to the hybridization reaction.

The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., (1998) Genome Res. August;8(8): 769–76). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence resonance energy transfer (FRET). Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995).

In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., (1998) Nat Biotechnol. January;16(1):49–53).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. In preferred embodiments the polymorphic base is within 5, 4, 3, 2, 1, nucleotides of the center of the said polynucleotide, more preferably at the center of said polynucleotide. Preferably the probes of the present invention are labeled or immobilized on a solid support.

By assaying the hybridization to an allele specific probe, one can detect the presence or absence of a biallelic marker allele in a given sample. High-Throughput parallel hybridizations in array format are specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in S. cerevisiae mutant strains, and in the protease gene of HIV-1 virus (Hacia et al., (1996) Nat Genet. December; 14(4): 441–7; Shoemaker et al., (1996) Nat Genet December; 14(4):450–6; Kozal et al., (1996) Nat Med. July;2(7): 753–9). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual, which target sequences include a polymorphic marker. EP 785280 describes a tiling strategy for the detection of single nucleotide polymorphisms.

Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995. In a particular aspect, arrays are tiled for a number of specific, identified biallelic marker sequences. In particular, the array is tiled to include a number of detection blocks, each detection block being specific for a specific biallelic marker or a set of biallelic markers.

For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424, 186.

Thus, in some embodiments, the chips may comprise an array of nucleic acid sequences of fragments of about 15 nucleotides in length. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides.

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping biallelic markers, the microfluidic system may integrate nucleic acid amplification, microsequencing, capillary electrophoresis and a detection method such as laser-induced fluorescence detection.

In a first step, the DNA samples are amplified, preferably by PCR. Then, the amplification products are subjected to automated microsequencing reactions using ddNTPs (specific fluorescence for each ddNTP) and the appropriate oligonucleotide microsequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can for example be polyacrylamide, polyethyleneglycol or dextran. The incorporated ddNTPs in the single-nucleotide primer extension products are identified by fluorescence detection. This microchip can be used to process at least 96 to 384 samples in parallel. It can use the usual four color laser induced fluorescence detection of the ddNTPs.

GSSP4 Association Studies

Association studies focus on population frequencies and rely on the phenomenon of linkage disequilibrium. Linkage disequilibrium is the deviation from random of the occurrence of pairs of specific alleles at different loci on the same chromosome. If a specific allele in a given gene is directly associated with a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region.

Case-control populations can be genotyped for biallelic markers to identify associations that narrowly locate a trait causing allele, as any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Case-Control Populations (Inclusion Criteria)

Population-based association studies do not concern familial inheritance, but compare the prevalence of a particular genetic marker, or a set of markers, in case-control populations. They are case-control studies based on comparison of unrelated case (affected or trait positive) individuals and unrelated control (unaffected, trait negative or random) individuals. Preferably, the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. The terms "trait positive population", "case population" and "affected population" are used interchangeably herein.

An important step in the dissection of complex traits using association studies is the choice of case-control populations (see, Lander and Schork, (1994) Science, September 30;265 (5181):2037–48). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity.

The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations consist of phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and preferably selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of trait negative individuals are included in such studies.

In the present invention, typical examples of inclusion criteria include obesity and disorders related to obesity as well as physiologic parameters associated with obesity, such as free fatty acid levels, glucose levels, insulin levels, leptin levels, triglyceride levels, free fatty acid oxidation levels, and weight loss.

Association Analysis

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (i.e. the associated allele is the trait causing allele), or more likely the associated allele is in linkage disequilibrium with the trait causing allele. The specific characteristics of the associated allele with respect to the candidate gene function usually give further insight into the relationship between the associated allele and the trait (causal or in linkage disequilibrium). If the evidence indicates that the associated allele within the candidate gene is most probably not the trait-causing allele but is in linkage disequilibrium with the real trait-causing allele, then the trait-causing allele can be found by sequencing the vicinity of the associated marker, and performing further association studies with the polymorphisms that are revealed in an iterative manner.

Association studies are usually run in two successive steps. In a first phase, the frequencies of a reduced number of biallelic markers from the candidate gene are determined in the trait positive and trait negative populations. In a second phase of the analysis, the position of the genetic loci responsible for the given trait is further refined using a higher density of markers from the relevant region. However, if the candidate gene under study is relatively small in length a single phase may be sufficient to establish significant associations.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odds ratio are calculated. If a statistically significant association is found the relative risk for an individual carrying the given haplotype of being affected with the trait under study can be approximated.

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists in stratifying the case-control populations with respect to a given haplotype for the first loci and performing a haplotype analysis with the second loci with each subpopulation.

VIII. Assays for Identifying Modulators of GSSP4 Polypeptide Activity

The invention features methods of screening for one or more compounds that modulate the activity of GSSP4s in cells, which includes providing potential compounds to be tested to the cells. Exemplary assays that may be used are described in the Examples 2, 5–7,9–11. To these assays would be added compounds to be tested for their inhibitory or stimulatory activity as compared to the effects of GSSP4 polypeptides alone. Other assays in which an effect is observed based on the addition of GSSP4 polypeptides can also be used to screen for modulators of GSSP4 polypeptide activity or effects of the presence of GSSP4 polypeptides on cells. The essential step is to apply an unknown compound and then to monitor an assay for a change from what is seen when only GSSP4 polypeptides are applied to the cell. A change is defined as something that is significantly different in the presence of the compound plus GSSP4 polypeptide compared to GSSP4 polypeptide alone. In this case, significantly different would be an "increase" or a "decrease" in a measurable effect of at least 25%, 30%, 35%, 40%, 45%, 50%, 55%, 60%, 65%, 70%, or 75%.

The term "modulation" as used herein refers to a measurable change in an activity. Examples include, but are not limited to, lipolysis stimulated receptor (LSR) modulation, leptin modulation, lipoprotein modulation, plasma FFA levels, FFA oxidation, TG levels, glucose levels, and weight. These effects can be in vitro or preferably in vivo. Modulation of an activity can be either an increase or a decrease in the activity. Thus, LSR activity can be increased or decreased, leptin activity can be increased or decreased, and lipoprotein activity can be increased or decreased. Similarly, FFA, TG, and glucose levels (and weight) can be increased or decreased in vivo Free Fatty Acid oxidation can be increased or decreased in vivo or ex vivo.

By "LSR" activity is meant expression of LSR on the surface of the cell, or in a particular conformation, as well as its ability to bind, uptake, and degrade leptin and lipoprotein. By "leptin" activity is meant its binding, uptake and degradation by LSR, as well as its transport across a blood brain barrier, and potentially these occurrences where LSR is not necessarily the mediating factor or the only mediating factor. Similarly, by "lipoprotein" activity is meant its binding, uptake and degradation by LSR, as well as these occurrences where LSR is not necessarily the mediating factor or the only mediating factor. Exemplary assays are provided in Examples 2, 5–7,9–11. These assay and other comparable assays can be used to determine/identify compounds that modulate GSSP4 polypeptide activity. In some cases it may be important to identify compounds that modulate some but not all of the GSSP4 polypeptide activities, although preferably all activities are modified.

The term "increasing" as used herein refers to the ability of a compound to increase the activity of GSSP4 polypeptides in some measurable way compared to the effect of GSSP4 polypeptides in its absence. As a result of the presence of the compound leptin binding and/or uptake might increase, for example, as compared to controls in the presence of the GSSP4 polypeptide alone. Preferably, an increase in activity is at least 25%, 30%, 35%, 40%, 45%, 50%, 55%, 60%, 65%, 70%, or 75% compared to the level of activity in the presence of the GSSP4 polypeptide.

Similarly, the term "decreasing" as used herein refers to the ability of a compound to decrease an activity in some measurable way compared to the effect of a GSSP4 polypeptide in its absence. For example, the presence of the compound decreases the plasma concentrations of FFA, TG, and glucose in mice. Also as a result of the presence of a compound leptin binding and/or uptake might decrease, for example, as compared to controls in the presence of the GSSP4 polypeptide alone. Preferably, an decrease in activity is at least 25%, 30%, 35%, 40%, 45%, 50%, 55%, 60%, 65%, 70%, or 75% as compared to the level of activity in the presence of the GSSP4 polypeptide alone.

The invention features a method for identifying a potential compound to modulate body mass in individuals in need of modulating body mass comprising: a) contacting a cell with a GSSP4 polypeptide and a candidate compound; b) detecting a result selected from the group consisting of LSR modulation, leptin modulation, lipoprotein modulation; FFA oxidation modulation; and c) wherein said result identifies said potential compound if said result differs from said result when said cell is contacted with the GSSP4 polypeptide alone.

In preferred embodiments, said contacting further comprises a ligand of said LSR. Preferably said ligand is selected from the group consisting of cytokine, lipoprotein, free fatty acids, and C1q, and more preferably said cytokine is leptin, and most preferably said leptin is a leptin polypeptide fragment as described in U.S. Provisional application No. 60/155,506 hereby incorporated by reference herein in its entirety including any figures, drawings, or tables.

In other preferred embodiments, said GSSP4 polypeptide is mouse or is human. In other preferred embodiments, said cell is selected from the group consisting of PLC, CHO-K1, Hep3B, and HepG2.

In yet other preferred embodiments, said lipoprotein modulation is selected from the group consisting of binding, uptake, and degradation. Preferably, said modulation is an increase in said binding, uptake, or degradation. Alternatively, said modulation is a decrease in said binding, uptake, or degradation.

In other preferred embodiments, leptin modulation is selected from the group consisting of binding, uptake, degradation, and transport. Preferably, said modulation is an increase in said binding, uptake, degradation, or transport. Alternatively, said modulation is a decrease in said binding, uptake, degradation, or transport. Preferably, said transport is across a blood-brain barrier.

In yet other preferred embodiments, said LSR modulation is expression on the surface of said cell. Preferably, said detecting comprises FACS, more preferably said detecting further comprises antibodies that bind specifically to said LSR, and most preferably said antibodies bind specifically to the carboxy terminus of said LSR.

In still other preferred embodiments, said potential compound is selected from the group consisting of peptides, peptide libraries, non-peptide libraries, peptoids, fatty acids, lipoproteins, medicaments, antibodies, small molecules, and proteases.

IX. Epitopes and Antibody Fusions

A preferred embodiment of the present invention is directed to eiptope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes. See, e.g., Geysen, et al. (1983) Proc. Natl. Acad. Sci. USA 81:39984002. It is particularly noted that although a particular epitope may not be immunogenic, it is nonetheless useful since antibodies can be made in vitro to any epitope.

An epitope can comprise as few as 3 amino acids in a spatial conformation which is unique to the epitope. Generally an epitope consists of at least 6 such amino acids, and more often at least 8–10 such amino acids. In preferred embodiment, antigenic epitopes comprise a number of amino acids that is any integer between 3 and 50. Fragments which function as epitopes may be produced by any conventional means. See, e.g., Houghten, R. A., Proc. Natl. Acad. Sci. USA 82:5131–5135 (1985), further described in U.S. Pat. No. 4,631,211. Methods for determining the amino acids which make up an immunogenic epitope include x-ray crystallography, 2-dimensional nuclear magnetic resonance, and epitope mapping, e.g., the Pepscan method described by H. Mario Geysen et al. (1984); Proc. Natl. Acad. Sci. U.S.A. 81:3998–4002; PCT Publication No. WO 84/03564; and PCT Publication No. WO 84/03506. Another example is the algorithm of Jameson and Wolf, Comp. Appl. Biosci. 4:181–186 (1988) (said references incorporated by reference in their entireties). The Jameson-Wolf antigenic analysis, for example, may be performed using the computer program PROTEAN, using default parameters (Version 4.0 Windows, DNASTAR, Inc., 1228 South Park Street Madison, Wis.).

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length sequence of the sequence listing. All combinations of sequences between the integers of 6 and the full-length sequence of a polypeptide of the present invention are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See, Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.; (1985) and Bittle, F. J. et al., (1985). A preferred immunogenic epitope includes the polypeptides of the sequence listing. The immunogenic epitopes may be presented together with a carrier protein, such as an albumin, to an animal system (such as rabbit or mouse) if necessary. Immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as—maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention including, but not limited to, polypeptides comprising an immunogenic or antigenic epitope can be fused to heterologous polypeptide sequences. For example, the polypeptides of the present invention may be fused with the constant region comprising portions of immunoglobulins (IgA, IgE, IgG, IgM), or portions of the constant region (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acids encoding the above epitopes can also be recombined with a gene of interest as an epitope tag to aid in detection and purification of the expressed polypeptide.

Additonal fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos. 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). (Each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Antibodies:

The present invention further relates to antibodies and T-cell antigen receptors (TCR), which specifically bind the polypeptides, and more specifically, the epitopes of the polyepeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab')2 and F(ab)2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991); U.S. Pat. Nos. 5,573,920, 4,474,893, 5,601,819, 4,714,681, 4,925,648; Kostelny, S. A. et al. (1992).

Antibodies of the present invention may be described or specified in terms of the epitope(s) or epitope-bearing portion(s) of a polypeptide of the present invention, which are recognized or specifically bound by the antibody. In the case of proteins of the present invention secreted proteins, the antibodies may specifically bind a full-length protein encoded by a nucleic acid of the present invention, a mature protein (i.e., the protein generated by cleavage of the signal peptide) encoded by a nucleic acid of the present invention, a signal peptide encoded by a nucleic acid of the present invention, or any other polypeptide of the present invention. Therefore, the epitope(s) or epitope bearing polypeptide portion(s) may be specified as described herein, e.g., by N-terminal and C-terminal positions, by size in contiguous amino acid residues, or otherwise described herein (including the sequence listing). Antibodies which specifically bind any epitope or polypeptide of the present invention may also be excluded as individual species. Therefore, the present invention includes antibodies that specifically bind specified polypeptides of the present invention, and allows for the exclusion of the same.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein, eg., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd value less than $5\times10^{-6}M$, $10^{-6}M$, $5\times10^{-7}M$, $10^{-7}M$, $5\times10^{-8}M$, $10^{-8}M$, $5\times10^{-9}M$, $10^{-9}M$, $5\times10^{-10}M$, $10^{-10}M$, $5\times10^{-11}M$, $10^{-11}M$, $5\times10^{-12}M$, $10^{-12}M$, $5\times10^{-13}M$, $10^{-13}M$, $5\times10^{-14}M$, $10^{-14}M$, $5\times10^{-15}M$, and $10^{-15}M$.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples (See, e.g., Harlow et al., 1988).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al. 1988); Hammerling, et al, 1981). (Said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992); and Sawai, H. et al. (1995); and Better, M. et al. (1988).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988). For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986); Gillies, S. D. et al. (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing, (EP 0 592 106; EP 0 519 596; Padlan E. A., 1991; Studnicka G. M. et al., 1994; Roguska M. A. et al., 1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741.

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art (See e.g., Harbor et al. supra; WO 93/21232; EP 0 439 095; Naramura, M. et al. 1994; U.S. Pat. No. 5,474,981; Gillies, S. O. et al., 1992; Fell, H. P. et al., 1991).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991); Zheng, X. X. et al. (1995); and Vil, H. et al. (1992).

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al. (1998) J.; Pitard, V. et al. (1997); Liautard, J. et al. (1997); Carlson, N. G. et al. (1997) J.; Taryman, R. E. et al. (1995); Muller, Y. A. et al. (1998); Bartunek, P. et al. (1996).

As discussed above, antibodies of the polypeptides of the invention can, in turn, be utilized to generate anti-idiotypic antibodies that "mimic" polypeptides of the invention using techniques well known to those skilled in the art (See, e.g. Greenspan and Bona (1989); and Nissinoff (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and therby block its biological activity, The invention also concerns a purified or isolated antibody capable of specifically binding to a mutated full length or mature polypeptide of the present invention or to a fragment or variant thereof comprising an epitope of the mutated polypeptide. In another preferred embodiment, the present invention concerns an antibody capable of binding to a polypeptide comprising at least 10 consecutive amino acids of a polypeptide of the present invention and including at least one of the amino acids which can be encoded by the trait causing mutations.

Non-human animals or mammals, whether wild-type or transgenic, which express a different species of a polypeptide of the present invention than the one to which antibody binding is desired, and animals which do not express a polypeptide of the present invention (i.e. a knock out animal) are particularly useful for preparing antibodies. Gene knock out animals will recognize all or most of the exposed regions of a polypeptide of the present invention as foreign antigens, and therefore produce antibodies with a wider array of epitopes. Moreover, smaller polypeptides with only 10 to 30 amino acids may be useful in obtaining specific binding to any one of the polypeptides of the present invention. In addition, the humoral immune system of animals which produce a species of a polypeptide of the present invention that resembles the antigenic sequence will preferentially recognize the differences between the animal's native polypeptide species and the antigen sequence, and produce antibodies to these unique sites in the antigen sequence. Such a technique will be particularly useful in obtaining antibodies that specifically bind to any one of the polypeptides of the present invention.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method for detecting specifically the presence of a polypeptide of the present invention according to the invention in a biological sample, said method comprising the following steps:

a) bringing into contact the biological sample with a polyclonal or monoclonal antibody that specifically binds a polypeptide of the present invention; and b) detecting the antigen-antibody complex formed.

The invention also concerns a diagnostic kit for detecting in vitro the presence of a polypeptide of the present invention in a biological sample, wherein said kit comprises:

a) a polyclonal or monoclonal antibody that specifically binds a polypeptide of the present invention, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

The antibodies of the invention may be labeled by any one of the radioactive, fluorescent or enzymatic labels known in the art.

EXAMPLES

The following Examples are provided for illustrative purposes and not as a means of limitation to support the finding that GSSP4 polypeptides have efficacy in reducing insulin resistance and improving glucose and lipid metabolism and may have an insulin sensitising action. One of ordinary skill in the art would be able to design equivalent assays and methods based on the disclosure herein all of which form part of the instant invention.

Example 1

Northern Analysis of GSSP4 RNA

Analysis of GSSP4 expression in different human tissues (adult and fetal) and cell lines, as well as mouse embryos in different stages of development, is accomplished by using poly A$^+$ RNA blots purchased from Clontech (e.g. #7780-1, 7757-1, 7756-1, 7768-1 and 7763-1). Labeling of RNA probes is performed using the RNA Strip-EZ kit from Ambion as per manufacture's instructions. Hybridization of RNA probes to RNA blots is performed Ultrahyb hybridization solution (Ambion). Briefly, blots are prehybridized for 30 min at 58° C. (low-strigency) or 65° C. (high stringency). After adding the labeled probe (2×10$^6$ cpm/ml), blots are hybridized overnight (14–24 hrs), and is washed 2×20 min at 50° C. with 2×SSC/0.1% SDS (low stringency), 2×20 min at 58° C. with 1×SSC/0.1% SDS (medium stringency) and 2×20 min at 65° C. with 1×SSC/0.1% SDS (high stringency). After washings are completed blots are exposed on the phosphoimager (Molecular Dynamics) for 1–3 days.

Example 2

In Vitro Tests of Metabolic-related Activity

The activity of various preparations of GSSP4 polypeptides are assessed using various in vitro assays including those provided below. These assays are also exemplary of those that can be used to develop GSSP4 polypeptide antagonists and agonists. To do that, the effect of GSSP4 polypeptides in the above assays, e.g. on glucose uptake and fatty acid oxidation and partitioning in the presence of the candidate molecules would be compared with the effect of GSSP4 polypeptides in the assays in the absence of the candidate molecules.

In Vitro Muscle Cells Glucose Uptake

L6 Muscle cells are obtained from the European Culture Collection (Porton Down) and are used at passages 7–11. Cells are maintained in standard tissue culture medium DMEM, and glucose uptake is assessed using [$^3$H]-2-deoxyglucose (2DG) with or without GSSP4 polypeptides in the presence or absence of insulin ($10^{-8}$ M) as has been previously described (Walker P S et al, Glucose transport activity in L6 muscle cells is regulated by the coordinate control of subcellular glucose transporter distribution, biosynthesis, and mRNA transcription, JBC, 1990;265(3), 1516–1523, and Kilp A et al, Stimulation of hexose transport by metformin in L6 muscle cells in culture, Endocrinology, 1992;130(5), 2535–2544). Uptake of 2DG is expressed as the percentage change compared with control (no added insulin or GSSP4). Values are presented as mean .+-.SEM of sets of 4 wells per experiment. Differences between sets of wells are evaluated by Student's t test, probability values $p<0.05$ are considered to be significant.

Effect on Muscle Cell Fatty Acid Oxidation

C2C12 cells are differentiated in the presence or absence of 2 μg/mL GSSP4 protein for 4 days. On day 4, oleate oxidation rates are determined by measuring conversion of 1-$^{14}$C-oleate (0.2 mM) to $^{14}CO_2$ for 90 min This experiment can be used to screen for active fragments and peptides as well as agonists and antagonists or activators and inhibitors of GSSP4 polypeptides.

The effect of polypeptides on the rate of oleate oxidation can be compared in differentiated C2C12 cells (murine skeletal muscle cells; ATCC, Manassas, Va. CRL-1772) and in a hepatocyte cell line (Hepa1–6; ATCC, Manassas, Va. CRL-1830). Cultured cells are maintained according to manufacturer's instructions. The oleate oxidation assay is performed as previously described (Muoio et al (1999) Biochem J 338;783–791). Briefly, nearly confluent myocytes are kept in low serum differentiation media (DMEM, 2.5% Horse serum) for 4 days, at which time formation of myotubes became maximal. Hepatocytes are kept in the same DMEM medium supplemented with 10% FCS for 2 days. One hour prior to the experiment the media is removed and 1 mL of preincubation media (MEM, 2.5% Horse serum, 3 mM glucose, 4 mM Glutamine, 25 mM Hepes, 1% FFA free BSA, 0.25 mM Oleate, 5 μg/mL gentamycin) is added. At the start of the oxidation experiment $^{14}$C-Oleic acid (1 μCi/mL, American Radiolabeled Chemical Inc., St. Louis, Mo.) is added and cells are incubated for 90 min at 37° C. in the absence/presence of 2.5 μg/mL GSSP4 polypeptides. After the incubation period 0.75 mL of the media is removed and assayed for $^{14}$C-oxidation products as described below for the muscle FFA oxidation experiment.

Triglyceride and Protein Partitioning Following Oleate Oxidaiton in Cultured Cells Following transfer of media for oleate oxidation assay, cells are placed on ice. To determine triglyceride and protein content, cells are washed with 1 mL of 1×PBS to remove residual media. To each well 300 μL of cell dissociation solution (Sigma) is added and incubated at 37° C. for 10 min. Plates are tapped to loosen cells, and 0.5 mL of 1×PBS is added. The cell suspension is transferred to an eppendorf tube, each well is rinsed with an additional 0.5 mL of 1×PBS, and is transferred to appropriate eppendorf tube. Samples are centrifuged at 1000 rpm for 10 minutes at room temperature. Supernatant is discarded and 750 μL of 1×PBS/2% chaps is added to cell pellet. Cell suspension is vortexed and placed on ice for 1 hour. Samples are then centrifuged at 13000 rpm for 20 min at 4° C. Supernatants are transferred to new tube and frozen at −20° C. until analyzed. Quantitative measure of triglyceride level in each sample is determined using Sigma Diagnostics GPO-TRINDER enzymatic kit. The procedure outlined in the manual is adhered to, with the following exceptions: assay is performed in 48 well plate, 350 μL of sample volume is assayed, control blank consisted of 350 μL PBS/2% chaps, and standard contained 10 μL standard provide in kit plus 690 μL PBS/2% chaps. Analysis of samples is carried out on a Packard Spectra Count at a wavelength of 550 nm. Protein analysis is carried out on 25 μL of each supernatant sample using the BCA protein assay (Pierce) following manufacturer's instructions. Analysis of samples is carried out on a Packard Spectra Count at a wavelength of 550 nm.

Cellular Binding and Uptake of GSSP4 Polypeptides as Detected by Fluorescence Microscopy Fluorecein isothiocyanate (FITC) conjugation of GSSP4 polypeptides: Purified GSSP4 proteins at 1 mg/mL concentration are labeled with FITC using Sigma's FluoroTag FITC conjugation kit (Stock No. FITC-1). Protocol outlined in the Sigma Handbook for small scale conjugation is followed for GSSP4 protein labeling.

Cell Culture: C2C12 mouse skeletal muscle cells (ATCC, Manassas, Va. CRL-1772) and Hepa-1–6 mouse hepatocytes (ATCC, Manassas, Va. CRL-1830) are seeded into 6 well plates at a cell density of $2 \times 10^5$ cells per well. C2C12 and Hepa-1–6 cells are cultured according to repository's instructions for 24–48 hours prior to analysis. Assay is performed when cells are 80% confluent.

FITC labeled GSSP4 proteincellular binding and uptake using microscopy: C2C12 and Hepa 1–6 cells are incubated in the presence/absence of antibody directed against human LSR (81B: N-terminal sequence of human LSR; does not cross react with mouse LSR and 93A: c-terminal sequence, cross reacts with mouse LSR) or an antiserum directed against gC1qr (953) for 1 hour at 37° C., 5% CO2. LSR antibodies are added to the media at a concentration of 2 μg/mL. The anti-gC1qr antiserum is added to the media at a volume of 2.5 μL undiluted serum (high concentration) or 1:100 dilution (low concentration). Following incubation with specified antibody, FITC-GSSP4 polypeptide (50 nM/mL) is added to each cell culture well. Cells are again incubated for 1 hour at 37° C., 5% CO2. Cells are washed 2× with PBS, cells are scraped from well into 1 mL of PBS. Cell suspension is transferred to an eppendorf tube and centrifuged at 1000 rpm for 2 minutes. Supernatant is removed and cells resuspended in 200 μL of PBS. Binding and uptake of FITC-GSSP4 polypeptide is analyzed by fluorescence microscopy under 40× magnification.

This assay may be useful for identifying agents that facilitate or prevent the uptake and/or binding of GSSP4 polypeptides to cells.

Example 3

In Vivo Tests for Metabolic-related Activity in Rodent Diabetes Models

As metabolic profiles differ among various animal models of obesity and diabetes, analysis of multiple models is undertaken to separate the effects GSSP4 polypeptides on hyperglycemia, hyperinsulinemia, hyperlipidemia and obesity. Mutation in colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31(1): 1–6) in mice and fa/fa in zucker rats have been developed by the various laboratories for understanding the pathophysiology of disease and testing the efficacy of new antidiabetic compounds (Diabetes, (1983) 32: 830–838; Annu. Rep. Sankyo Res. Lab. (1994). 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention are tested for blood sugar and triglycerides lowering activities. Zucker (fa/fa) rats are severely obese, hyperinsulinemic, and insulin resistant (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299–340), and the fa/fa mutation may be the rat equivalent of the murine db mutation (Friedman et al., Cell 69:217–220, 1992; Truett et al., Proc. Natl. Acad. Sci. USA 88:7806, 1991). Tubby (tub/tub) mice are characterized by obesity, moderate insulin resistance and hyperinsulinemia without significant hyperglycemia (Coleman et al., J. Heredity 81:424, 1990).

Previously, leptin was reported to reverse insulin resistance and diabetes mellitus in mice with congenital lipodystrophy (Shimomura et al. Nature 401: 73–76 (1999). Leptin is found to be less effective in a different lipodystrophic mouse model of lipoatrophic diabetes (Gavrilova et al Nature 403: 850 (2000); hereby incorporated herein in its entirety including any drawings, figures, or tables).

The streptozotocin (STZ) model for chemically-induced diabetes is tested to examine the effects of hyperglycemia in the absence of obesity. STZ-treated animals are deficient in insulin and severely hyperglycemic (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299–340). The monosodium glutamate (MSG) model for chemically-induced obesity (Olney, Science 164:719, 1969; Cameron et al., Cli. Exp. Pharmacol. Physiol. 5:41, 1978), in which obesity is less severe than in the genetic models and develops without hyperphagia, hyperinsulinemia and insulin resistance, is also examined. Finally, a non-chemical, non-genetic model for induction of obesity includes feeding rodents a high fat/high carbohydrate (cafeteria diet) diet ad libitum.

The instant invention encompasses the use of GSSP4 polypeptides for reducing the insulin resistance and hyperglycemia in any or all of the above rodent diabetes models or in humans with Type I or Type II diabetes or other preferred metabolic diseases described previously or models based on other mammals. In the compositions of the present invention the GSSP4 polypeptides may, if desired, be associated with other compatible pharmacologically-active antidiabetic agents such as insulin, leptin (U.S. provisional application No. 60/155,506), or troglitazone, either alone or in combination. Assays include that described previously in Gavrilova et al. ((2000) Diabetes November;49(11): 1910–6; (2000) Nature February 24;403(6772):850) using A-ZIP/F-1 mice, except that GSSP4 polypeptides are administered intraperotineally, subcutaneously, intramuscularly or intravenously. The glucose and insulin levels of the mice would be tested, and the food intake and liver weight monitored, as well as other factors, such as leptin, FFA, and TG levels, typically measured in our experiments.

In Vivo Assay for Anti-hyperglycemic Activity of GSSP4 Polypeptides

Genetically altered obese diabetic mice (db/db) (male, 7–9 weeks old) are housed (7–9 mice/cage) under standard laboratory conditions at 22.degree. C. and 50% relative humidity, and maintained on a diet of Purina rodent chow and water ad libitum. Prior to treatment, blood is collected from the tail vein of each animal and blood glucose concentrations are determined using One Touch BasicGlucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide GSSP4 polypeptides, saline, and an irrelevant peptide to the mice subcutaneously (s.c.). Blood is sampled from the tail vein hourly for 4 hours and at 24, 30 h post-dosing and analyzed for blood glucose concentrations. Food is withdrawn from 0–4 h post dosing and reintroduced thereafter. Individual body weights and mean food consumption (each cage) are also measured after 24 h. Significant differences between groups (comparing GSSP4 treated to saline-treated) are evaluated using Student t-test.

In Vivo Insulin Sensitivity Assay

In vivo insulin sensitivity is examined by utilizing two-step hyperinsulinemic-euglycemic clamps according to the following protocol. Rodents from any or all of the various models described in Example 2 are housed for at least a week prior to experimental procedures. Surgeries for the placement of jugular vein and carotid artery catheters are performed under sterile conditions using ketamine and xylazine (i.m.) anesthesia. After surgery, all rodents are allowed to regain consciousness and placed in individual cages. GSSP4 polypeptides or vehicle is administered through the jugular vein after complete recovery and for the following two days. Sixteen hours after the last treatment, hyperinsulinemic-euglycemic clamps are performed. Rodents are placed in restrainers and a bolus of 4 .mu Ci [3-.sup.3 H] glucose (NEN) is administered, followed by a continuous infusion of the tracer at a dose of 0.2 mu.Ci/min (20 mu.1/min). Two hours after the start of the tracer infusion, 3 blood samples (0.3 ml each) are collected at 10 minute intervals (−20–0 min) for basal measurements. An insulin infusion is then started (5 mU/kg/min), and 100 .mu.1 blood samples are taken every 10 min. to monitor plasma glucose.

A 30% glucose solution is infused using a second pump based on the plasma glucose levels in order to reach and maintain euglycemia. Once a steady state is established at 5 mU/kg/min insulin (stable glucose infusion rate and plasma glucose), 3 additional blood samples (0.3 ml each) are obtained for measurements of glucose, [3-$^3$H] glucose and insulin (100–120 min.). A higher dose of insulin (25 mU/kg/min.) is then administered and glucose infusion rates are adjusted for the second euglycemic clamp and blood samples are taken at min. 220–240. Glucose specific activity is determined in deproteinized plasma and the calculations of Rd and hepatic glucose output (HGO) are made, as described (Lang et al., Endocrinology 130:43, 1992). Plasma insulin levels at basal period and after 5 and 25 mU/kg/min. infusions are then determined and compared between GSSP4 treated and vehicle treated rodents.

Insulin regulation of glucose homeostasis has two major components; stimulation of peripheral glucose uptake and suppression of hepatic glucose output. Using tracer studies in the glucose clamps, it is possible to determine which portion of the insulin response is affected by the GSSP4 polypeptides.

Example 4

Effect of GSSP4 Polypeptides on Mice Fed a High-Fat Diet

Experiments are performed using approximately 6 week old C57B1/6 mice (8 per group). All mice are housed individually. The mice are maintained on a high fat diet throughout each experiment. The high fat diet (cafeteria diet; D12331 from Research Diets, Inc.) has the following composition: protein kcal % 16, carbohydrate kcal % 26, and fat kcal % 58. The fat is primarily composed of coconut oil, hydrogenated.

After the mice are fed a high fat diet for 6 days, microosmotic pumps are inserted using isoflurane anesthesia, and are used to provide full-length GSSP4 polypeptides, GSSP4 polypeptide fragments, saline, and an irrelevant peptide to the mice subcutaneously (s.c.) for 18 days. GSSP4 polypeptides are provided at doses of 100, 50, 25, and 2.5 µg/day and the irrelevant peptide is provided at 10 µg/day. Body weight is measured on the first, third and fifth day of the high fat diet, and then daily after the start of treatment. Final body weight and final blood samples are taken by cardiac puncture and are used to determine triglyceride (TG), total cholesterol (TC), glucose, leptin, and insulin levels. The amount of food consumed per day is also determined for each group. Plasma glucose is determined by a glucose oxidase procedure (Analox GM7) and plasma insulin determined by radioimmunoassay (Amerlex, Amersham).

Example 5

Effect of GSSP4 Polypeptides on Plasma Free Fatty Acid in C57 BL/6 Mice

The effect of GSSP4 polypeptides on postprandial lipemia (PPL) in normal C57BL6/J mice is tested.

The mice used in this experiment are fasted for 2 hours prior to the experiment after which a baseline blood sample is taken. All blood samples are taken from the tail using EDTA coated capillary tubes (50 µL each time point). At time 0 (8:30 AM), a standard high fat meal (6 g butter, 6 g sunflower oil, 10 g nonfat dry milk, 10 g sucrose, 12 mL distilled water prepared fresh following Nb#6, JF, pg.1) is given by gavage (vol.=1% of body weight) to all animals.

Immediately following the high fat meal, 25 µg a GSSP4 polypeptide is injected i.p. in 100 µL saline. The same dose (25 µg/mL in 100 µL) is again injected at 45 min and at 1 hr 45 min. Control animals are injected with saline (3×100 µL). Untreated and treated animals are handled in an alternating mode.

Blood samples are taken in hourly intervals, and are immediately put on ice. Plasma is prepared by centrifugation following each time point. Plasma is kept at −20° C. and free fatty acids (FFA), triglycerides (TG) and glucose are determined within 24 hours using standard test kits (Sigma and Wako). Due to the limited amount of plasma available, glucose is determined in duplicate using pooled samples. For each time point, equal volumes of plasma from all 8 animals per treatment group are pooled.

Example 6

Effect of GSSP4 Polypeptides on Plasma Leptin and Insulin in C57 BL/6 Mice

The effect of GSSP4 polypeptides on plasma leptin and insulin levels during postprandial lipemia (PPL) in normal C57BL6/J mice is tested. The experimental procedure is the same as previously described, except that blood is drawn only at 0, 2 and 4 hours to allow for greater blood samples needed for the determination of leptin and insulin by RIA.

Briefly, 16 mice are fasted for 2 hours prior to the experiment after which a baseline blood sample is taken. All blood samples are taken from the tail using EDTA coated capillary tubes (100 µL each time point). At time 0 (9:00AM), a standard high fat meal is given by gavage (vol.=1% of body weight) to all animals. Immediately following the high fat meal, 25 µg of a GSSP4 polypeptide is injected i.p. in 100 µL saline. The same dose (25 µg in 100 µL) is again injected at 45 min and at 1 hr 45 min (treated group). Control animals are injected with saline (3×100 µL). Untreated and treated animals are handled in an alternating mode.

Blood samples are immediately put on ice and plasma is prepared by centrifugation following each time point. Plasma is kept at −20° C. and free fatty acids (FFA) are determined within 24 hours using a standard test kit (Wako). Leptin and Insulin are determined by RIA (ML-82K and SRI-13K, LINCO Research, Inc., St. Charles, Mo.) following the manufacturer's protocol. However, only 20 µL plasma is used. Each determination is done in duplicate. Due to the limited amount of plasma available, leptin and insulin are determined in 4 pools of 2 animals each in both treatment groups.

Example 7

Effect of GSSP4 Polypeptides on Plasma FFA, TG and Glucose in C57 BL/6 Mice

The effect of GSSP4 polypeptides on plasma FFA, TG, glucose, leptin and insulin levels during postprandial lipemia (PPL) in normal C57BL6/J mice has been described. Weight loss resulting from GSSP4 polypeptides (2.5 µg/day) given to normal C57BL6/J mice on a high fat diet is shown.

The experimental procedure is similar to described previously. Briefly, 14 mice are fasted for 2 hours prior to the experiment after which a baseline blood sample is taken. All blood samples are taken from the tail using EDTA coated capillary tubes (50 µL each time point). At time 0 (9:00AM), a standard high fat meal is given by gavage (vol.=1% of body weight) to all animals. Immediately following the high fat meal, 4 mice are injected 25 µg of a GSSP4 polypeptide i.p. in 100 µL saline. The same dose (25 µg in 100 µL) is again injected at 45 min and at 1 hr 45 min. A second treatment group receives 3 times 50 µg GSSP4 polypeptide at the same intervals. Control animals are injected with saline (3×100 µL). Untreated and treated animals are handled in an alternating mode.

Blood samples are immediately put on ice. Plasma is prepared by centrifugation following each time point. Plasma is kept at −20° C. and free fatty acids (FFA), triglycerides (TG) and glucose are determined within 24 hours using standard test kits (Sigma and Wako).

Example 8

Effect of GSSP4 Polypeptides on FFA Following Epinephrine Injection

In mice, plasma free fatty acids increase after intragastric administration of a high fat/carbohydrate test meal. These free fatty acids are mostly produced by the activity of lipolytic enzymes i.e. lipoprotein lipase (LPL) and hepatic lipase (HL). In this species, these enzymes are found in significant amounts both bound to endothelium and freely circulating in plasma. Another source of plasma free fatty acids is hormone sensitive lipase (HSL) that releases free fatty acids from adipose tissue after β-adrenergic stimulation. To test whether GSSP4 polypeptides also regulate the metabolism of free fatty acid released by HSL, mice are injected with epinephrine.

Two groups of mice are given epinephrine (5 µg) by intraperitoneal injection. A treated group is injected with a GSSP4 polypeptide (25 µg) one hour before and again together with epinephrine, while control animals receive saline. Plasma is isolated and free fatty acids and glucose are measured as described above.

Example 9

Effect of GSSP4 Polypeptides on Muscle FFA Oxidation

To investigate the effect of GSSP4 polypeptides on muscle free fatty acid oxidation, intact hind limb muscles from C57BL/6J mice are isolated and FFA oxidation is measured using oleate as substrate (Clee et al (2000) J Lipid Res 41:521–531; Muoio et al (1999) Am J Physiol 276: E913–921). Oleate oxidation in isolated muscle is measured as previously described (Cuendet et al (1976) J Clin Invest 58:1078–1088; Le Marchand-Brustel (1978) Am J Physiol 234:E348–E358). Briefly, mice are sacrificed by cervical dislocation and soleus and EDL muscles are rapidly isolated from the hind limbs. The distal tendon of each muscle is tied to a piece of suture to facilitate transfer among different media. All incubations are carried out at 30° C. in 1.5 mL of Krebs-Henseleit bicarbonate buffer (118.6 mM NaCl, 4.76 mM KCl, 1.19 mM $KH_2PO_4$, 1.19 mM $MgSO_4$, 2.54 mM $CaCl_2$, 25 mM $NaHCO_3$, 10 mM Hepes, pH 7.4) supplemented with 4% FFA free bovine serum albumin (fraction V, RIA grade, Sigma) and 5 mM glucose (Sigma). The total concentration of oleate (Sigma) throughout the experiment is 0.25 mM. All media are oxygenated (95% $O_2$; 5% $CO_2$) prior to incubation. The gas mixture is hydrated throughout the experiment by bubbling through a gas washer (Kontes Inc., Vineland, N.J.).

Muscles are rinsed for 30 min in incubation media with oxygenation. The muscles are then transferred to fresh media (1.5 mL) and incubated at 30° C. in the presence of 1 µCi/mL $[1-^{14}C]$ oleic acid (American Radiolabeled Chemicals). The incubation vials containing this media are sealed with a rubber septum from which a center well carrying a piece of Whatman paper (1.5 cm×11.5 cm) is suspended.

After an initial incubation period of 10 min with constant oxygenation, gas circulation is removed to close the system to the outside environment and the muscles are incubated for 90 min at 30° C. At the end of this period, 0.45 mL of Solvable (Packard Instruments, Meriden, Conn.) is injected onto the Whatman paper in the center well and oleate oxidation by the muscle is stopped by transferring the vial onto ice.

After 5 min, the muscle is removed from the medium, and an aliquot of 0.5 mL medium is also removed. The vials are closed again and 1 mL of 35% perchloric acid is injected with a syringe into the media by piercing through the rubber septum. The $CO_2$ released from the acidified media is collected by the Solvable in the center well. After a 90 min collection period at 30° C., the Whatman paper is removed from the center well and placed in scintillation vials containing 15 mL of scintillation fluid (HionicFlour, Packard Instruments, Meriden, Conn.). The amount of $^{14}C$ radioactivity is quantitated by liquid scintillation counting. The rate of oleate oxidation is expressed as nmol oleate produced in 90 min/g muscle.

To test the effect of gACRP30 or ACRP30 on oleate oxidation, these proteins are added to the media at a final concentration of 2.5 µg/mL and maintained in the media throughout the procedure.

Example 10

Effect of GSSP4 Polypeptides on Triglyceride in Muscle & Liver Isolated from Mice To determine whether the increased FFA oxidation induced by GSSP4 polypeptides is also accompanied by increased FFA delivery into muscle or liver, the hindlimb muscle and liver triglyceride content is measured after the GSSP4 polypeptide treatment of mice. Hind limb muscles as well as liver samples are removed from treated and untreated animals and the triglyceride and free fatty acid concentration is determined following a standard lipid extraction method (Shimabukuro et al (1997) Proc Natl Acad Sci USA 94:4637–4641) followed by TG and FFA analysis using standard test kits.

Example 11

Effect of GSSP4 Polypeptides on FFA following Intralipid Injection

Two groups of mice are intravenously (tail vein) injected with 30 µL bolus of Intralipid-20% (Clintec) to generate a sudden rise in plasma FFAs, thus by-passing intestinal absorption. (Intralipid is an intravenous fat emulsion used in nutritional therapy). A treated group (GSSP4 polypeptide-treated) is injected with a GSSP4 polypeptide (25 µg) at 30 and 60 minutes before Intralipid is given, while control animals (▲ control) received saline. Plasma is isolated and FFAs are measured as described previously. The effect of GSSP4 polypeptides on the decay in plasma FFAs following the peak induced by Intralipid injection is then monitored.

Example 12

Tests of Obesity-related Activity in Humans

Tests of the efficacy of in humans are performed in accordance with a physician's recommendations and with established guidelines. The parameters tested in mice are also tested in humans (e.g. food intake, weight, TG, TC, glucose, insulin, leptin, FFA). It is expected that the physiological factors would show changes over the short term. Changes in weight gain might require a longer period of time. In addition, the diet is carefully monitored. GSSP4 is given in daily doses of about 6 mg protein per 70 kg person or about 10 mg per day. Other doses are tested, for instance 1 mg or 5 mg per day up to 20 mg, 50 mg, or 100 mg per day.

Example 13

Tests of Obesity-related Activity in a Murine Lipoatrophic Diabetes Model

Leptin was reported to reverse insulin resistance and diabetes mellitus in mice with congenital lipodystrophy (Shimomura et al. Nature 401: 73–76 (1999). Leptin is found to be less effective in a different lipodystrophic mouse model of lipoatrophic diabetes (Gavrilova et al Nature 403: 850 (2000); hereby incorporated herein in its entirety including any drawings, figures, or tables). The instant invention encompasses the use of GSSP4 or polypeptide fragments for reducing the insulin resistance and hyperglycaemia in this model either alone or in combination with leptin, the leptin peptide (U.S. provisional application No. 60/155,506), or other compounds. Assays include that described previously in Gavrilova et al. ((2000) Diabetes November;49(11): 1910–6; (2000) Nature February 24;403(6772):850) using A-ZIP/F-1 mice, except that would be administered using the methods previously described in Example 5 (or Examples 8–10). The glucose and insulin levels of the mice would be tested, and the food intake and liver weight monitored, as well as other factors, such as leptin, FFA, and TG levels, typically measured in our experiments (see Example 5, above, or Examples 8–10).

What is claimed is:

1. A method of reducing circulating free fatty acid levels in an individual comprising administering to said individual a physiologically acceptable composition comprising a carrier and a polypeptide comprising SEQ ID NO:3, wherein said method reduces body mass.

2. A method of reducing circulating glucose levels in an individual comprising administering to said individual a physiologically acceptable composition comprising a carrier and a polypeptide comprising SEQ ID NO:3, wherein said method reduces body mass.

3. A method of reducing circulating triglyceride levels in an individual comprising administering to said individual a physiologically acceptable composition comprising a carrier and a polypeptide comprising SEQ ID NO:3, wherein said method reduces body mass.

4. A method of reducing circulating cholesterol levels in an individual comprising administering to said individual a physiologically acceptable composition comprising a carrier and a polypeptide comprising of SEQ ID NO:3, wherein said method reduces body mass.

5. A method of treating obesity comprising the administration of a therapeutically effective amount of a composition comprising SEQ ID NO: 3 and a pharmaceutically acceptable diluent.

6. A method of reducing body weight comprising providing to an individual a composition comprising SEQ ID NO: 3 and a pharmaceutically acceptable diluent.

* * * * *

UNITED STATES PATENT AND TRADEMARK OFFICE
CERTIFICATE OF CORRECTION

PATENT NO. : 7,223,727 B2
APPLICATION NO. : 10/467554
DATED : May 29, 2007
INVENTOR(S) : Barbara Chicca et al.

It is certified that error appears in the above-identified patent and that said Letters Patent is hereby corrected as shown below:

Column 3,
Line 56, "regulating activies" should read --regulating activities--.
Line 58, "regulating activies" should read --regulating activities--.
Line 60, "regulating activies" should read --regulating activities--.
Line 62, "regulating activies" should read --regulating activities--.
Line 64, "regulating activies" should read --regulating activities--.

Column 9,
Line 47, "m=A or G" should read --m=A or C--.
Line 58, "y=T or G" should read --y=T or C--.

Column 13,
Line 1, "involve the the control" should read --involve the control--.

Column 17,
Lines 11-12, "do not have an metabolic-related" should read --do not have a metabolic-related--.

Column 18,
Line 4, "effecting" should read --affecting--.

Column 20,
Line 8, "an decrease" should read --a decrease--.

Column 27,
Line 51, "ie." should read --i.e.,--.

Column 28,
Line 4, "Preferably polpeptides" should read --Preferably polypeptides--.

Column 36,
Line 16, "decrease" should read --decreased--.

Column 47,
Line 29, "as the the mouse" should read --as the mouse--.

UNITED STATES PATENT AND TRADEMARK OFFICE
CERTIFICATE OF CORRECTION

PATENT NO. : 7,233,727 B2
APPLICATION NO. : 10/467554
DATED : May 29, 2007
INVENTOR(S) : Barbara Chicca et al.

It is certified that error appears in the above-identified patent and that said Letters Patent is hereby corrected as shown below:

Column 50,
Line 5, "physiologically acceptable acceptable" should read --physiologically acceptable--.

Column 63,
Line 67, "artefactual cross-hybridization" should read --artifactual cross-hybridization--.

Column 68,
Line 36, "an decrease" should read --a decrease--.

Column 69,
Line 60, "preferably comprises" should read --preferably comprise--.

Column 71,
Line 20, "are hereby incorporated" should read --is hereby incorporated--.

Column 76,
Line 57, "manufacture's" should read --manufacturer's--.

Column 78,
Lines 1-2, "Oleate Oxidaiton" should read --Oleate Oxidation--.

Column 104,
Line 4, "comprising of SEQ ID NO: 3" should read --comprising SEQ ID NO: 3--.

Signed and Sealed this

Seventeenth Day of June, 2008

JON W. DUDAS
*Director of the United States Patent and Trademark Office*